US010671706B2

(12) United States Patent
Kasprisin et al.

(10) Patent No.: US 10,671,706 B2
(45) **Date of Patent: *Jun. 2, 2020**

(54) TISSUE MANAGEMENT SYSTEM

(75) Inventors: Duke O Kasprisin, South Burlington, VT (US); Paul E. Kozloski, Wayzata, MN (US); Susan A. Kozloski, Wayzata, MN (US); Agnes Vercillo, Cicero, NY (US); Jeffrey K. Winstead, Fishers, IN (US)

(73) Assignee: Biomedical Synergies, Inc., Wayzata, MN (US)

( * ) Notice: Subject to any disclaimer, the term of this patent is extended or adjusted under 35 U.S.C. 154(b) by 1242 days.

This patent is subject to a terminal disclaimer.

(21) Appl. No.: 11/975,525

(22) Filed: Oct. 19, 2007

(65) Prior Publication Data

US 2008/0215363 A1 Sep. 4, 2008

Related U.S. Application Data

(63) Continuation-in-part of application No. 11/584,357, filed on Oct. 20, 2006, now Pat. No. 8,666,762, which
(Continued)

(51) Int. Cl.
*G16H 40/20* (2018.01)
*G06F 19/00* (2018.01)
(Continued)

(52) U.S. Cl.
CPC ......... *G06F 19/3481* (2013.01); *G06Q 10/08* (2013.01); *G06Q 50/22* (2013.01); *G16H 40/20* (2018.01)

(58) Field of Classification Search
USPC ........................................................... 702/19
See application file for complete search history.

(56) References Cited

U.S. PATENT DOCUMENTS 4,745,759 A * 5/1988 Bauer ..................... A01N 1/02 435/284.1
5,416,029 A 5/1995 Miller et al.
(Continued)

OTHER PUBLICATIONS

American Association of Tissue Banks, Guidance Document, Current Good Tissue Practice, Jun. 27, 2006, pp. 30 and 38.*

*Primary Examiner* — Lena Najarian
(74) *Attorney, Agent, or Firm* — DeWitt LLP

(57) ABSTRACT

The present invention provides a comprehensive tissue management system for transplantable materials like tissues and organs. The tracking portion of the system prompts and verifies that staff members of a medical establishment like a hospital have handled, stored, transported, reconstituted, and used the tissue or organ materials in a safe and regulatory-compliant manner from the point of receipt to the point of issuance or surgical use throughout the hospital's organization. The tracing portion of the system creates an integral record that documents which hospital staff members have provided which processing steps to the tissue or organ, any associated materials used in conjunction with such tissue or organ, and an identification of the tissue or organ that was transplanted or implanted inside a patient. Such a system will enable adverse reaction investigations for transplant patients, and recalls of transplantable materials.

24 Claims, 42 Drawing Sheets

Related U.S. Application Data is a continuation-in-part of application No. 11/540,844, filed on Sep. 29, 2006, now abandoned.

(60) Provisional application No. 60/826,492, filed on Sep. 21, 2006.

(51) Int. Cl.

| | |
|---|---|
| ***G06Q 10/08*** | (2012.01) |
| ***G06Q 50/22*** | (2018.01) |

(56) References Cited

U.S. PATENT DOCUMENTS

| | | | | |
|---|---|---|---|---|
| 5,842,179 | A * | 11/1998 | Beavers et al. | 705/28 |
| 5,855,617 | A * | 1/1999 | Orton | 128/898 |
| 6,385,593 | B2 * | 5/2002 | Linberg | 705/28 |
| 6,512,459 | B2 | 1/2003 | Benezech et al. | |
| 6,539,360 | B1 | 3/2003 | Kadaba | |
| 6,786,405 | B2 * | 9/2004 | Wiedenhoefer | 235/385 |
| 6,861,954 | B2 * | 3/2005 | Levin | 340/572.1 |
| 7,363,167 | B2 * | 4/2008 | Csore et al. | 702/19 |
| 7,383,284 | B2 * | 6/2008 | Heinrichs et al. | |
| 8,666,762 | B2 * | 3/2014 | Kasprisin et al. | 705/2 |
| 2001/0034614 | A1 * | 10/2001 | Fletcher-Haynes et al. | 705/2 |
| 2001/0037220 | A1 * | 11/2001 | Merry et al. | 705/3 |
| 2002/0049650 | A1 | 4/2002 | Reff | |
| 2002/0082957 | A1 | 6/2002 | Krassi | |
| 2002/0143580 | A1 * | 10/2002 | Bristol et al. | 705/2 |
| 2002/0194029 | A1 | 12/2002 | Guan et al. | |
| 2003/0120633 | A1 | 6/2003 | Torre-Bueno | |
| 2003/0175242 | A1 * | 9/2003 | Gruenberg | 424/93.2 |
| 2004/0088189 | A1 * | 5/2004 | Veome | A61M 1/3681 705/2 |
| 2004/0117207 | A1 | 6/2004 | Brown | |
| 2004/0122735 | A1 * | 6/2004 | Meshkin | G06Q 30/02 705/14.27 |
| 2004/0186746 | A1 | 9/2004 | Angst | |
| 2004/0249666 | A1 | 12/2004 | Napolitano et al. | |
| 2005/0010437 | A1 | 1/2005 | Abukwedar | |
| 2005/0010449 | A1 | 1/2005 | Abukwedar | |
| 2005/0027567 | A1 | 2/2005 | Taha | |
| 2005/0055242 | A1 | 3/2005 | Bello et al. | |
| 2005/0055244 | A1 | 3/2005 | Mullan et al. | |
| 2005/0065817 | A1 | 3/2005 | Mihai et al. | |
| 2005/0262088 | A1 * | 11/2005 | Solis et al. | 707/10 |
| 2005/0285715 | A1 | 12/2005 | Comunale | |
| 2006/0031098 | A1 * | 2/2006 | Kalthoff et al. | 705/2 |
| 2006/0036286 | A1 * | 2/2006 | Whitehurst et al. | 607/3 |
| 2006/0062771 | A1 * | 3/2006 | Sasaki et al. | 424/93.7 |
| 2007/0142745 | A1 * | 6/2007 | Brahm | 600/562 |

* cited by examiner

Suppliers

Home | SOP | Facilities | Staff | Storage | Inventory | Adverse Reaction | Suppliers | Recall | Reports | Search | Documentation Home > Suppliers

Suppliers

Actions

| Title | Types | Tissue Types | Catalogs | Recalls | Actions | Title | Status |
|---|---|---|---|---|---|---|---|
| AGS | Pharmaceutical | 0 | 0 | 0 | | Musculoskeletal / Bone | Approved |
| AcmeS | Surgical Supplies | 0 | 0 | 0 | | | |
| ASurS | Surgical Supplies | 0 | 0 | 0 | | Musculoskeletal / Fascia | Unapproved |
| AIlS | Tissue Bank | 5 | 1 | 3 | | | |
| BI | Tissue Bank | 1 | 1 | 0 | | Musculoskeletal / Ligament | Other |
| BI | Distributor | 0 | 0 | 0 | | | |
| Central | Tissue Bank | 0 | 0 | 0 | | Organ / Heart | Approved |
| Comm | Tissue Bank | 0 | 0 | 0 | | | |
| Cry | Tissue Bank | 1 | 1 | 7 | | Organ / Other Organ | Other |
| LifeC | Tissue Bank | 5 | 1 | 7 | | | |
| LifeN | Tissue Bank | 4 | 1 | 3 | | | |
| MTF | Tissue Bank | 4 | 0 | 0 | | | |
| Ost | Tissue Bank | 0 | 0 | 0 | | | |
| RETech | Tissue Bank | 2 | 0 | 0 | | | |
| TisBankInt | Tissue Bank | | | | | | |

View All Site Content
Announcements
Documents
Internet Links
- Suppliers
- Tissue Recall Links
Discussions
People and Groups
Recycle Bin

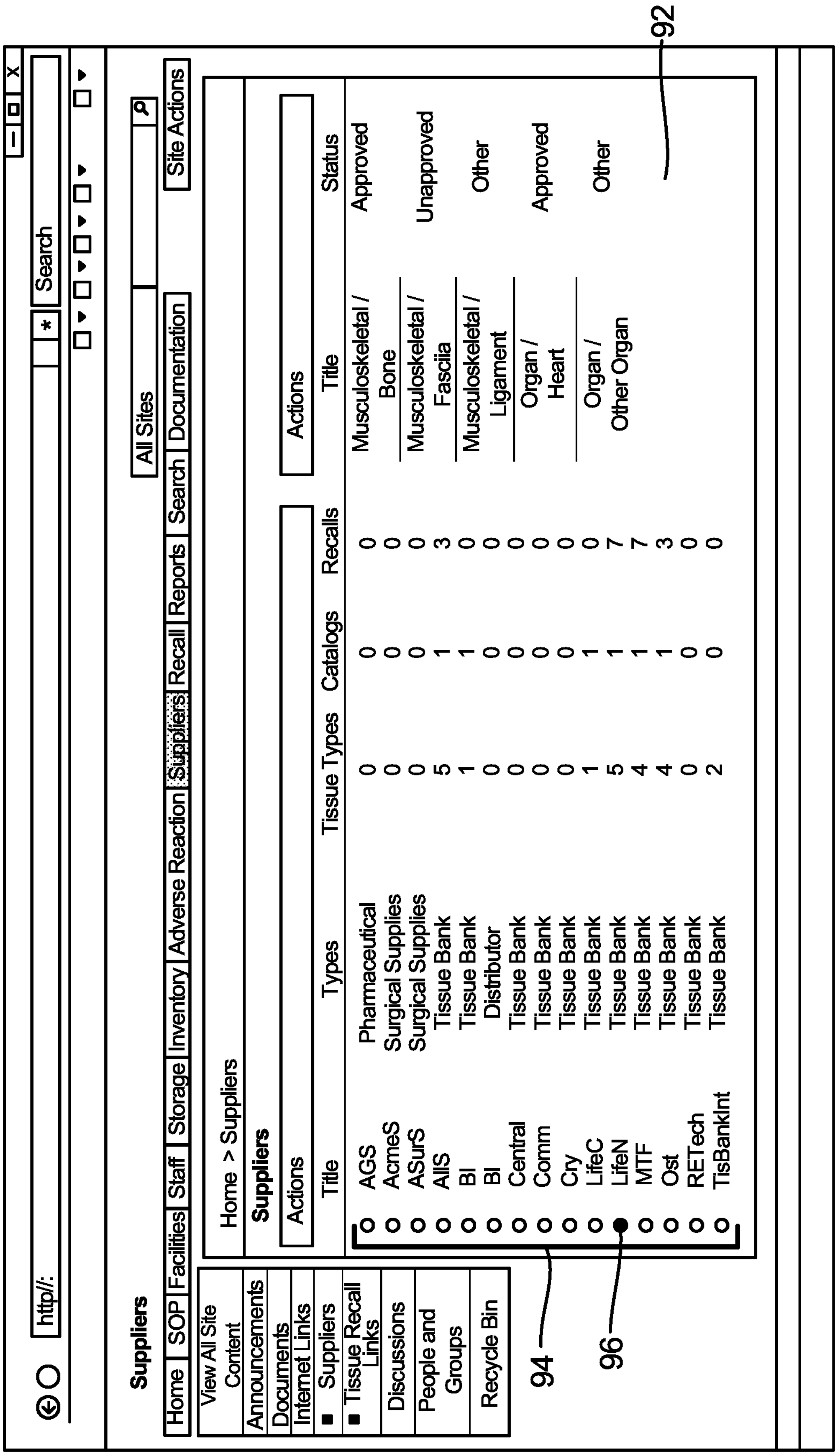

Fig. 5

Edit Supplier Tissue Status

Supplier: Allosource — 100
Type: Tissue Bank — 102
Tissue Classification:

| | Class | Tissue | Status | FDA Registration | Expire Date | Alerting? | Notes |
|---|---|---|---|---|---|---|---|
| ▼ Autologous — 104 | | ▼ Type: Other Autologous Tissue — 106 | | | | Add Tissue — 108 | |
| ☒ ▼ | Musculoskeletal | Bone — 114 | Approved | AL-23948 — 116 | 01-Jan-2008 | ☑ | Confirm with Monte |
| ☒ ▼ | Musculoskeletal | Fascia | Approved | AL-23948 | 15-Jun-2009 | ☐ | Need this ASAP! |
| ☒ ▼ | Musculoskeletal | Ligament | Approved | | | ☐ | |
| ☒ ▼ | Musculoskeletal | Tendon | Unapproved | | | ☐ | |
| ☒ ▼ | Musculoskeletal | Alloderm | Unapproved | | | | |

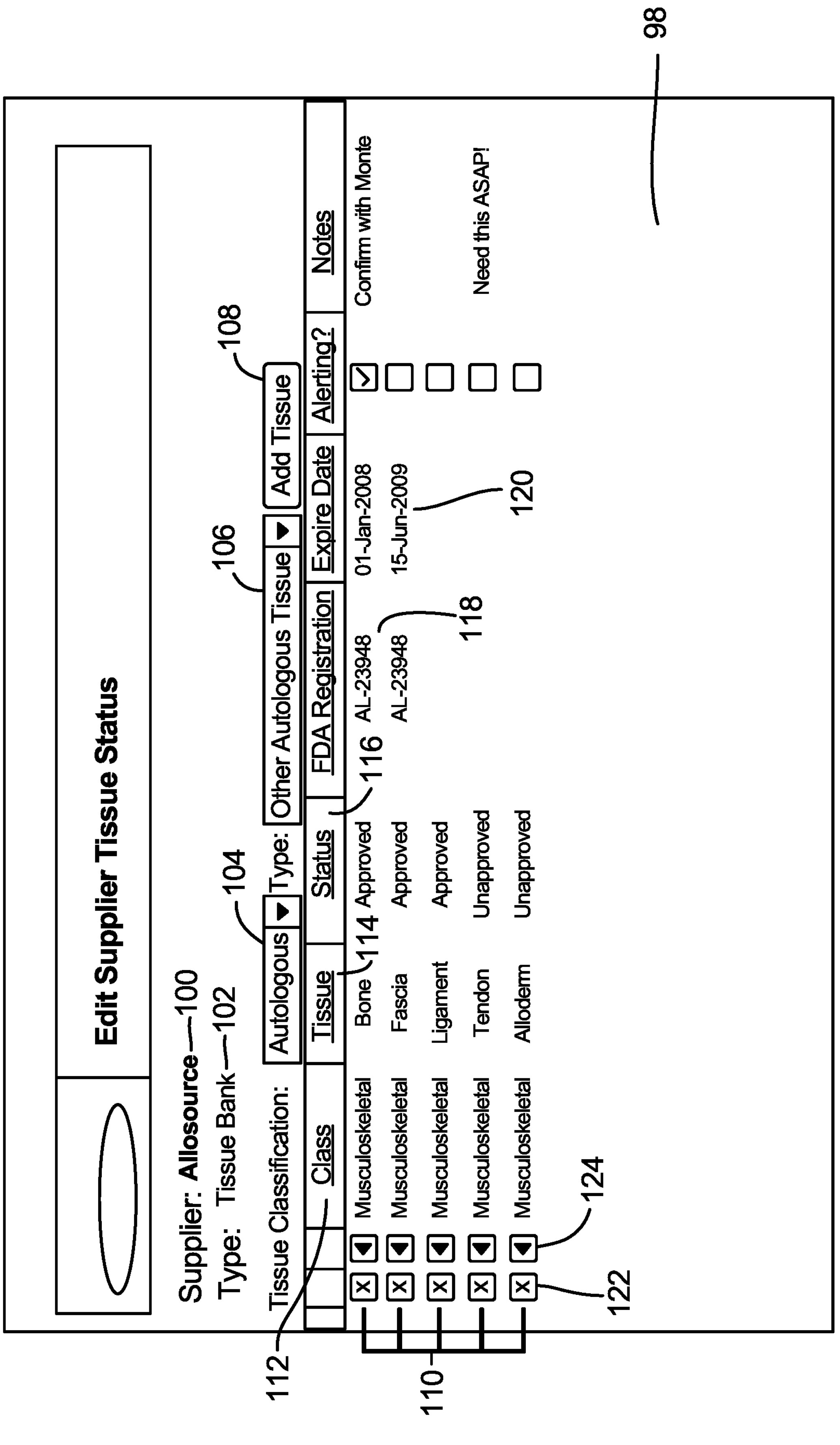

Fig. 6

SOP

Home | SOP | Facilities | Staff | Storage | Inventory | Adverse Reaction | Suppliers | Recall | Reports | Search | Documentation All Sites | Site Actions

Order Tissue

Filter: Suppliers
Allosource ▼

Supplier Actions — 140
- Create New Order
- View Profile

Open Purchase Orders

Actions

| Title | Status | Items | Type | Dated | Total Fee |
|---|---|---|---|---|---|
| AE-55543 | Partially Received | 2 | Standard Order | 01-May-2007 | $750.00 |
| AE-7549 | On Order | 1 | Standard Order | 04-Jun-2007 | $1,500.00 |
| AE-9873 | On Order | 1 | Standard Order | 22-Jun-2007 | $1,100.00 |
| CY-0815-1 | On Order | 1 | Standard Order | 15-Aug-2007 | $0.00 |
| LS-1-1 | On Order | 1 | Standard Order | 14-May-2007 | $111.00 |
| LS-1-7 | Partially Received | 2 | Standard Order | 29-Mar-2007 | $4900.00 |
| NA-1 | On Order | 1 | Standard Order | 19-Jun-2007 | $14,000.00 |

134 — Status
135 — Items
136 — Type
137 — (Type grouping)
138 — Dated
139 — Total Fee
132 — (header region)
130 — (window)

Open Line Items

Actions

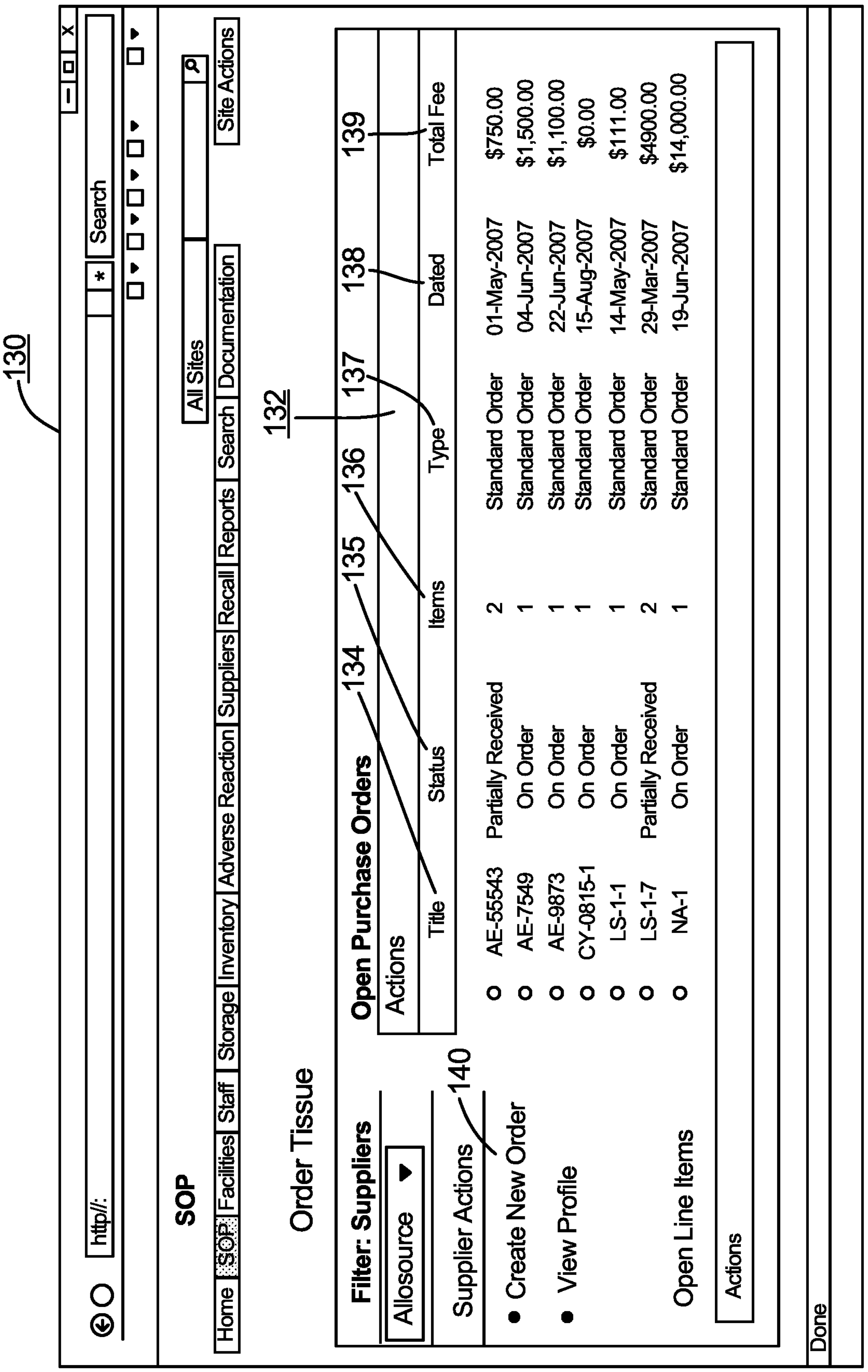

Fig. 7

Order Tissue

Step 1: Enter Purchase Order Header

You are creating a NEW purchase order.

From Supplier: Allosource (Tissue Bank) — 144
To Facility: Methodist Hospital (Hospital) — 145
Order Type: Standard Order — 146
PO Number: — 147
Order Date: Monday, October 08, 2007
Confirmation Number: — 151

Notes — 150

*Shipping Information*

Courier: UPS - (Ground Carrier) — 148
Tracking Number: — 149

Next | Cancel — 152

142

Order Tissue

Step 2: Specify Tissue

PO Number: in, Monday, 08-Oct-2007, Standard Order.

Catalog: [2007] — 156

● Product Code    Allosource (Tissue Bank) — 154

[Lookup] — 165

○ Select — 166    164

Classification: ?
Tissue Type: ?
Product: ?
Size: ?

Size Details (if needed): — 168

Quantity: [1] — 169    Fee, each: [ ] — 170

Adjustment, each: [ ]    Reason: [ ]

Inventory Type: [Stock ▼]   Required by: [ ]
                  171

☐ Reserved

[Add Tissue] — 172

Tissues presently on this order: 0
Review and change tissues in the next step.

[Previous]   [Next] [Cancel] — 174

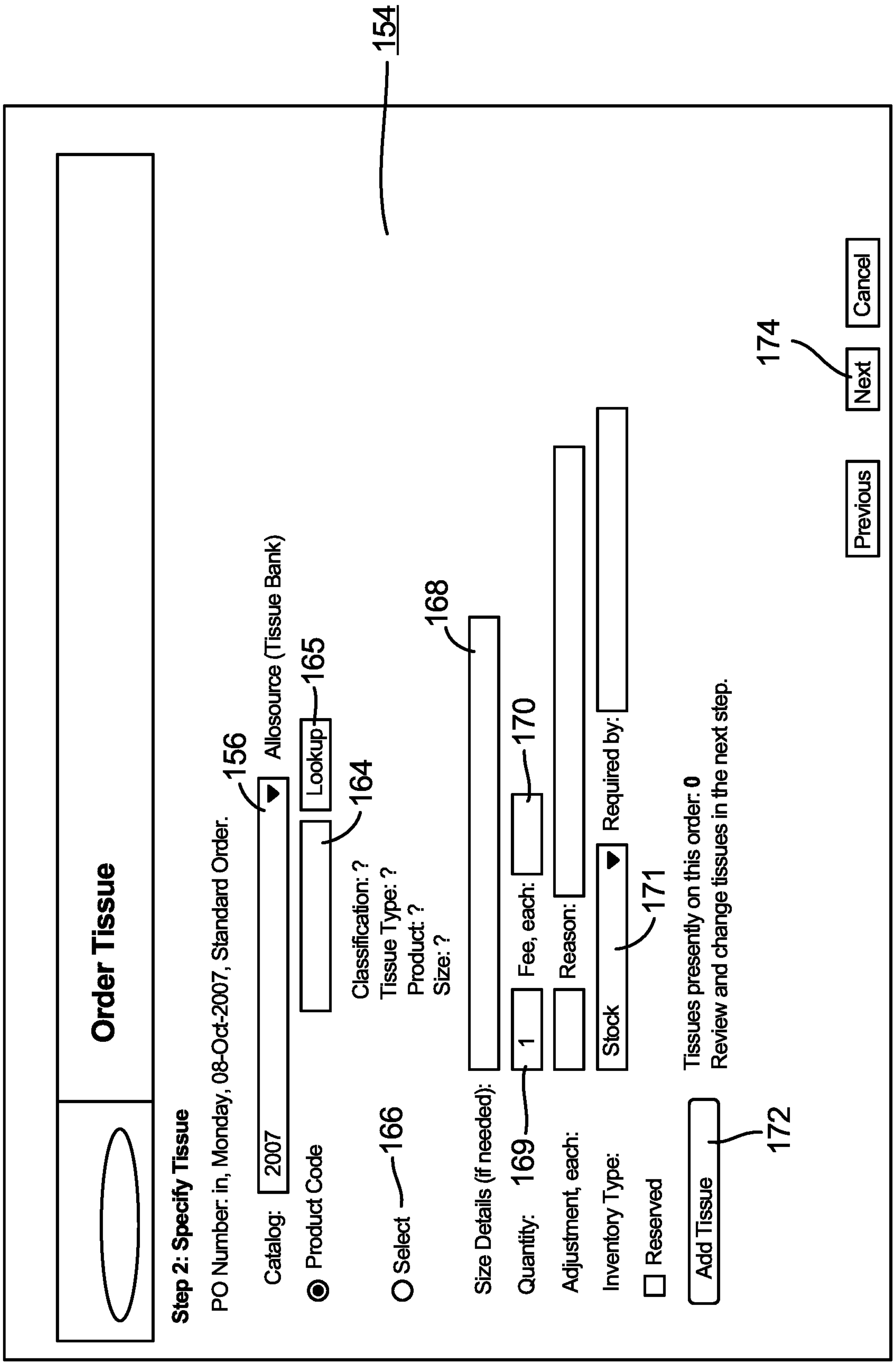

Fig. 9

Edit Tissue Definition

Supplier: Allosource  
Tissue Type: (All Types)  
Catalog: 2007

| | Tissue | Description | Measurement | Temperature | Target Temp | Packaging | Storage | Alert? |
|---|---|---|---|---|---|---|---|---|
| Edit Select | Alloderm | Cancellous Cubes, Freeze Dried | Volume | Room Temperature | 72.0 °F | Other | General Dry Storage | ☐ |
| Edit Select | Bone | Demineralized Cancellous Cubes | Block | Room Temperature | 72.0 °F | Other | General Dry Storage | ☐ |
| Edit Select | Bone | Cervical Spacers | Hollow Cylinder | Room Temperature | 72.0 °F | Peel Pack | General Dry Storage | |
| Edit Select | Bone | Cortical Strut | Area | Room Temperature | 72.0 °F | Peel Back | General Dry Storage | ☐ |
| Edit Select | Bone | Dowel w/o Cartigae | Length | Room Temperature | 72.0 °F | Other | General Dry Storage | ☐ |
| Edit Select | Bone | Femoreal Ring | Length | Room Temperature | 65.0 °F | Other | General Dry Storage | ☐ |

1 2 3 4 5 6 7 8

| | Code | Size | Description | Fee | Stocked? | Consigned? | Reorder | Par | In Lots? | Lot Size | Unique ID? |
|---|---|---|---|---|---|---|---|---|---|---|---|
| Edit | 12115010 | n/a | 1 x 10cm | $355 | ☐ | | | | | | ☐ |
| Edit | 12115024 | n/a | 2 x 15cm | $355 | | ☐ | | | ☐ | | ☐ |
| Edit | 12115025 | n/a | 2 x 25m Frozen | $150 | | | | | | | ☐ |
| Edit | 12117010 | n/a | 1 x 10cm Frozen | | ☐ | | | | ☐ | | ☐ |
| Edit | 12117024 | n/a | 2 x 15cm Frozen | | | | | | | | ☐ |
| Edit | 12117025 | n/a | 2 x 25cm Frozen | $450 | | ☐ | | | ☐ | | ☐ |

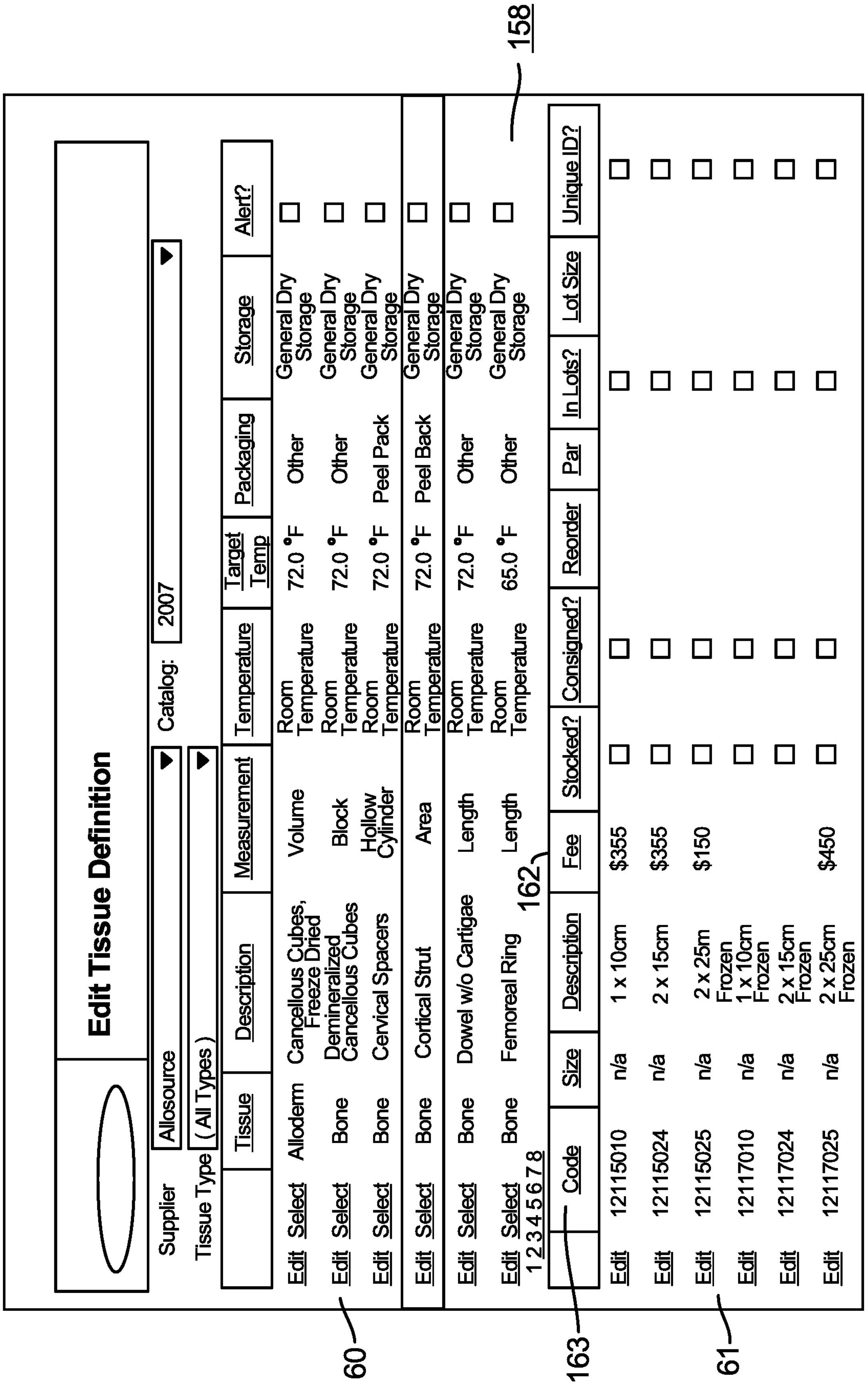

Fig. 10

Order Tissue

Step 3: Review Tissue

Supplier: Allosource

PO Number: in, Monday, 08-Oct-2007, Standard Order.

| | Description | Fee | Qty | Adj | Total | Type | Status |
|---|---|---|---|---|---|---|---|
| ▼ ☒ | 12420060 - Costal Cartilage, >= 6.1cm | $111.00 | 1 | | $111.00 | Stock | On Order |

178 — ▼ 180
179 — ☒

[Previous] [Next] [Cancel]   — 181

— 176

Order Tissue

Finished: Confirm and Submit

Supplier: Allosource
PO Number: in
Order Date: Monday, 08-Oct-2007
Order Type: Standard Order.

Line Item Count: 1
Line Item Total: $111.00
Line Item Adjustments: $0.00
Subtotal: $111.00
Overall Order Adjustments:: _____ — 185  Reason: _____
Total: $111.00

Previous  Next  Cancel

184

186

Receive Tissue

Home | SOP | Facilities | Staff | Storage | Inventory | Adverse Reaction | Suppliers | Recall | Reports | Search | Documentation

Open Purchase Orders

Actions

| Title | Dated | Supplier Name | Items | Total |
|---|---|---|---|---|
| Ae-1254 | 26-Jun-2007 | Osteo | 2 | $100.00 |
| Ae-55543 | 01-May-2007 | Allosource | 2 | $750.00 |
| Ae-7549 | 04-Jun-2007 | Allosource | 1 | $1500.00 |
| Ae-9873 | 22-Jun-2007 | Allosource | 1 | $1100.00 |
| CY-0814-4 | 14-Aug-2007 | Lifenet | 1 | $1980.00 |
| CY-0815-1 | 15-Aug-2007 | Allosource | 1 | ($75.00) |
| cyTest1 | 02-Jul-2007 | Osteo | 2 | $100.00 |
| cyTest2 | 02-Jul-2007 | Lifenet | 0 | |
| LS-1-1 | 14-May-2007 | Allosource | 1 | $111.00 |
| LS-1-11 | 03-Apr-2007 | Bacterin | 2 | $655.00 |
| LS-1-12 | 03-Apr-2007 | Osteo | 2 | $0.00 |
| LS-1-6 | 02-Apr-2007 | Osteo | 2 | $0.00 |
| LS-1-7 | 29-Mar-2007 | Allosource | 2 | $4900.00 |
| LS-1-8 | 03-Apr-2007 | Bacterin | 2 | $0.00 |
| LS-2-3 | 05-Apr-2007 | Lifenet | 2 | $21,558.00 |

Open Line Items

Actions

| Title | Ordered | Received | Fee |
|---|---|---|---|

To display data in this web part, select an item in:

Open Purchase Orders

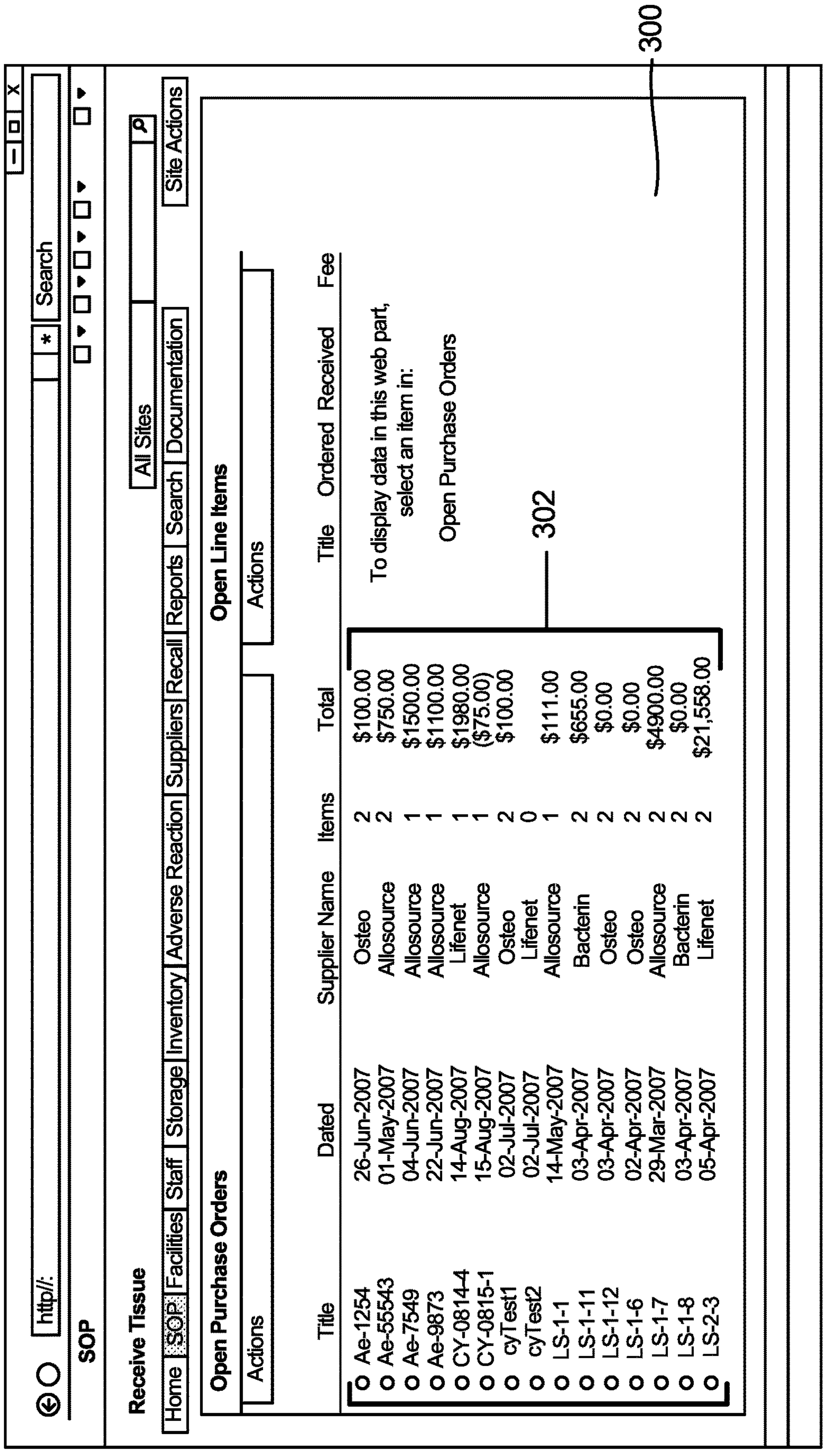

Fig. 13

Receive Tissue

Finished: Record Information Unique to each Item

PO Number: — 340
Ordered: In / Allosource — 342
 1, Received: 1 All items received — 341
Product: Other / Other Type of Tissue / Costal Cartilage
 12420060 - >=6.1cm — 343

Bar Code: _____ — 344   [Save] — 345   — 346
Expires: Sunday, October 31, 2010
Lot Number: 3876 — 347    UniqueID  058 — 348
Donor: _____
Size Details: — 350

| Bar Code | Size | Lot | Expiration | Storage Location |
|---|---|---|---|---|
| [X] 058-3876 | | 3876 | Oct-2010 | Methodist - Storage Cab #1 |

— 360

(No Action - Close Window) ▼ — 362
 — 352

Product Quality Checks, Notes:
☑ Temperature maintained during shipping — 353
☑ Entire product label is legible — 353
☑ Product packaging is intact — 354
☑ Other quality checks are OK — 355
▼▲
☐ Reject/Return to supplier — 356

— 338

[Previous]   [Next]  [Cancel]
 — 358

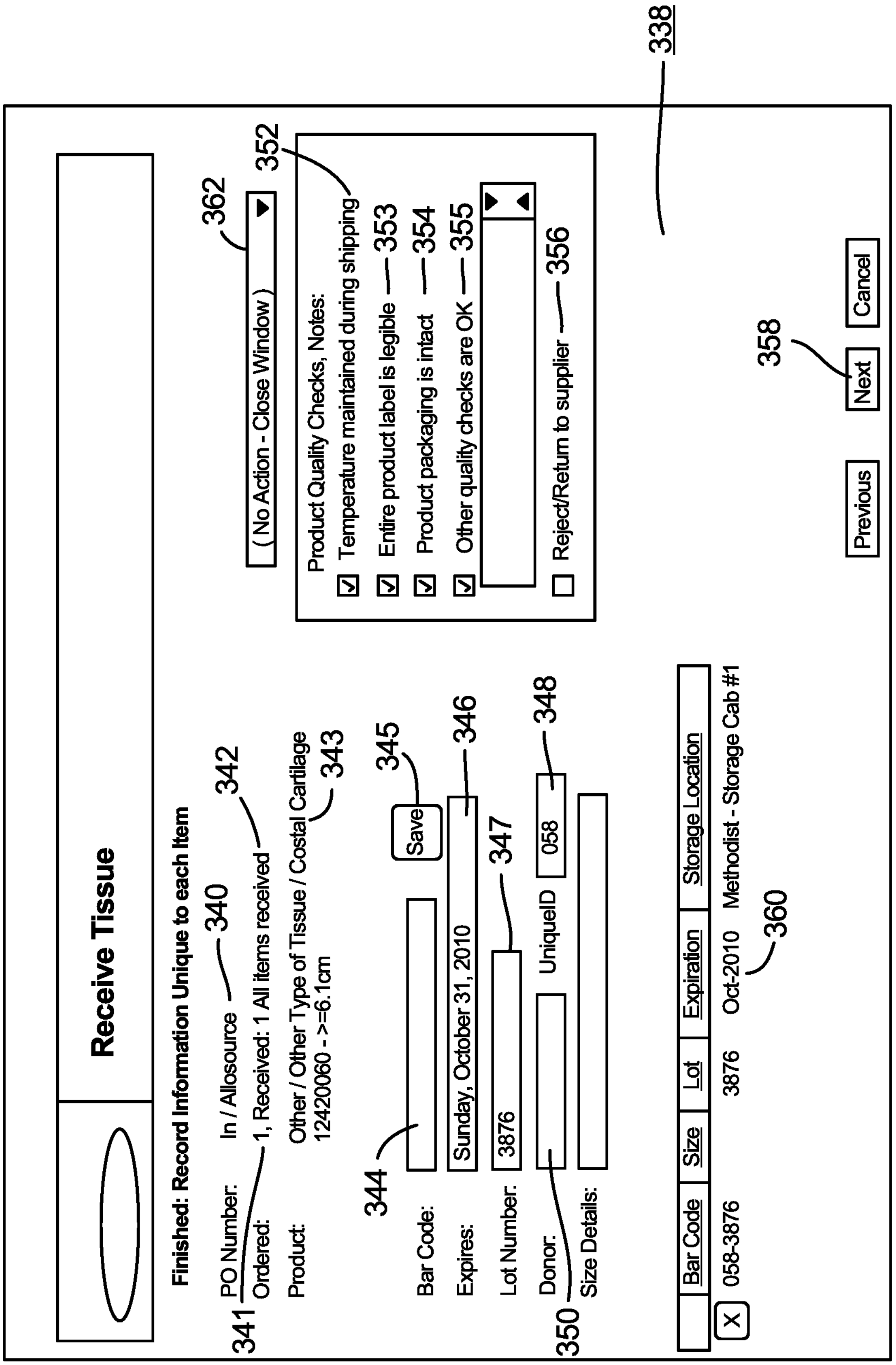

Fig. 16

Record Storage Temperature

Facility Name: Methodist Hospital  } 702
Storage Location: Storage Cab #1 / General Dry Storage Date Recorded: —704
Monday, October 8, 2007 19:57   □ ○  [71.5] °F —706   Notes [         ] —708

[Save] [Cancel] —710

Last 10 Records:

| Date/Time | Recorded By | Temperature () | Notes |
|---|---|---|---|
| ☒ 04-Oct-07 12:51 | Winstead, Jeff | 72.60 | |
| ☒ 28-Sep-07 09:54 | Winstead, Jeff | 72.60 | |
| ☒ 06-Aug-07 14:36 | Yellick, Craig | 77.10 | |
| ☒ 14-Jun-07 15:00 | Winstead, Jeff | 72.00 | |
| ☒ 11-Jun-07 09:31 | Winstead, Jeff | 65.00 | |

1.2

Move Tissue

Step 2: Record Tissue Movement

- Product: Other / Other Type of Tissue / Costal Cartilage — 392
  12420060 - >=6.1cm
- Bar Code: 058-3876, Expiration: 31-Oct-2010 — 394
- Date & Time of Transfer: Monday, October 8, 2007 19:55 — 395
- Staff Releasing Tissue: Winstead, Jeff — 396
- Staff Receiving Tissue: Yellick, Craig — 397
- Reason for Movement: Transfer to Surgery — 398
- Temperature: Room Temperaure at ___ °F — 402, 403
- Tissue Status: Available — 404
- Destination Facility: Methodist Hospital (Hospital)
- Storage Location: Storage Cab #1 (General Dry Storage-Room Temperature)
- Handling Notes:

☑ Reserved — 406
- Surgery Date: Tuesday, October 09, 2007 — 407
- Patient: 2-001922 — 408
- Physician Order #: 190467 — 409
- Notes: Dr. Kelly — 410

Product Quality Checks, Notes: — 412
☑ Temperature maintained during storage — 413
☑ Entire product label is legible — 414
☑ Product packaging is intact — 415
☑ Other quality checks are OK

[Previous] [Submit] [Cancel] — 417

390
393

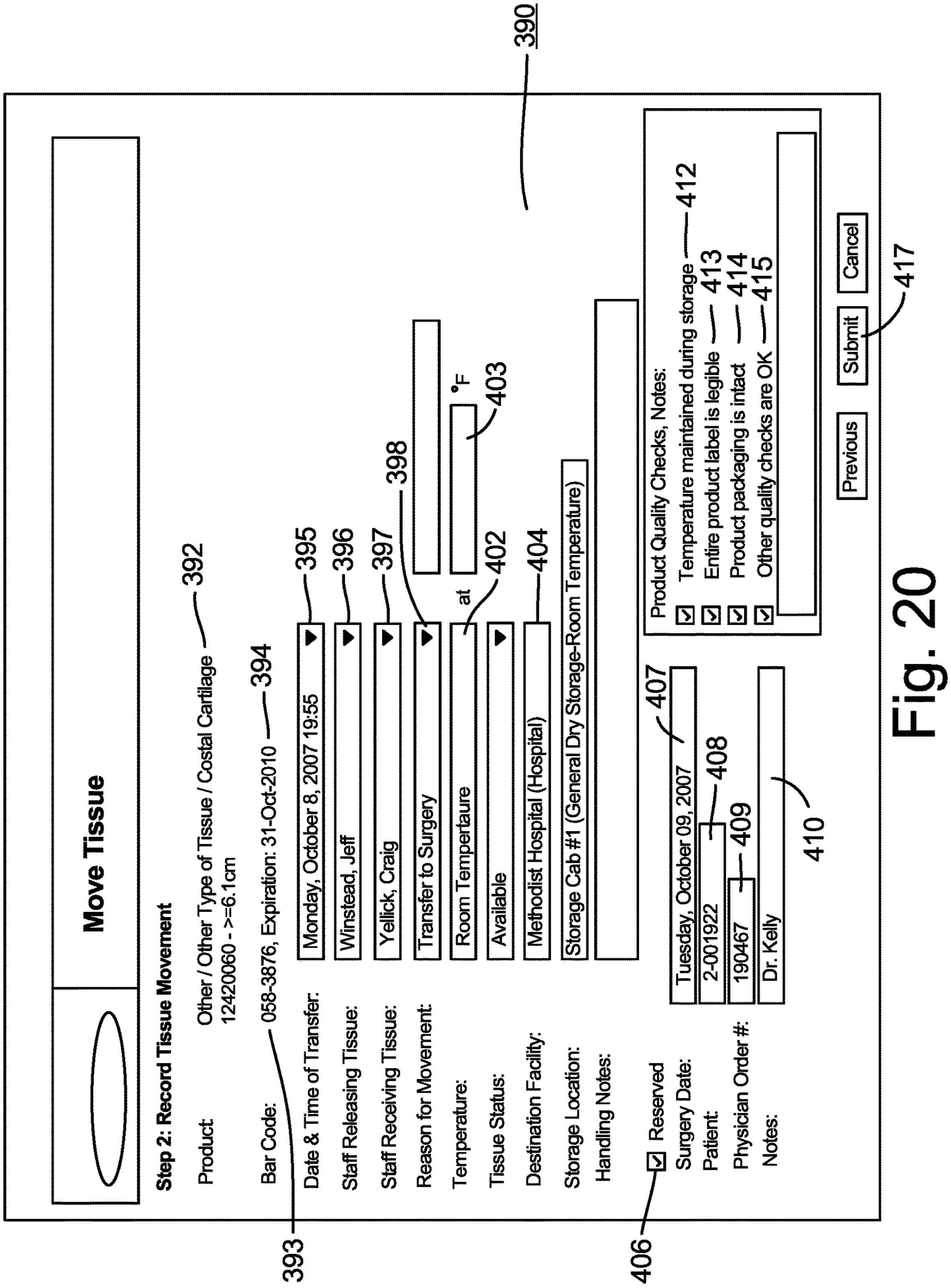

Fig. 20

| Filter | | Inventory Items | | | | | | | | |
|---|---|---|---|---|---|---|---|---|---|---|
| Apply Filter \| Reset | | Actions | | | | | | | | 1-20 ▲ |
| | | Supplier | Description | PO Number | Bar Code | Expires | Inventory Type | Status | Facility | Stor. Loc. | Temp. Type |
| Supplier | --Show All-- ▶ | MTF | 038 100A - DBX DBM | JW-061807 | 783-0983*1 | 2010-07 | Stock | Avail. | MH | Cab 1 | Room |
| Classification | --Show All-- ▶ | MTF | 038 100A - DBX DBM | JW-061807 | 783-0983*2 | 2010-07 | Stock | Avail. | MH | Cab 1 | Room |
| Tissue Type | --Show All-- ▶ | MTF | 038 100A - DBX DBM | JW-061807 | 783-0983*3 | 2010-07 | Stock | Avail. | MH | Cab 1 | Room |
| Inventory Type | --Show All-- ▶ | MTF | 038 100A - DBX DBM | JW-061807 | 783-0983*5 | 2010-07 | Stock | Avail. | MH | Cab 1 | Room |
| Temperature | --Show All-- ▶ | MTF | 038 100A - DBX DBM | CY-0607-1 | 783-0983*6 | 2010-07 | Stock | Avail. | MH | Cab 1 | Room |
| Surgery | --Show All-- ▶ | MTF | 038 100A - DBX DBM | CY-0607-1 | CY-0607-1 | 2009-09 | Stock | Avail. | MH | Cab 1 | Room |
| | | MTF | 038 100A - DBX DBM | CY-0607-1 | CY-0607-2 | 2009-09 | Stock | Avail. | MH | Cab 1 | Room |
| | | MTF | 038 100A - DBX DBM | CY-0607-1 | CY-0607-4 | 2009-09 | Stock | Avail. | MH | Cab 1 | Room |
| | | MTF | 038 100A - DBX DBM | CY-0607-1 | Cy-0607-5 | 2009-09 | Stock | Avail. | MH | Cab 1 | Room |
| | | Allosource | 10017000 Achilles Tendon | AE-51244 | CY-0607-2 | 2007-07 | Consign. | Reserved | MH | Freez. | Frozen |
| | | Allosource | 10017000 Achilles Tendon | AE-1991 | 135468735 | 2010-10 | Consign. | Avail. | MH | Storage | Frozen |
| | | Allosource | 12420060 Cartilage | AE-3541 | CX-1 | 2007-01 | Stock | Avail. | MH | Storage | Room |
| | | Allosource | 12420060 Cartilage | AE-09876 | 123798 | 2009-10 | Consign. | Avail. | MH | Cab 1 | Room |
| | | Allosource | 12420060 Cartilage | in | 058-3876 | 2010-10 | Consign. | Avail. | MH | Cab 1 | Room |
| | | Allosource | 12814015 Demin. Cortical | AE-3541 | AE-1 | 2009-02 | Consign. | Reserved | MH | Cab | Room |
| | | Allosource | 14417150 Fascia Lata | NA-47119 | 812 | 2008-07 | Consign. | Avail. | MH | Cab 1 | Room |

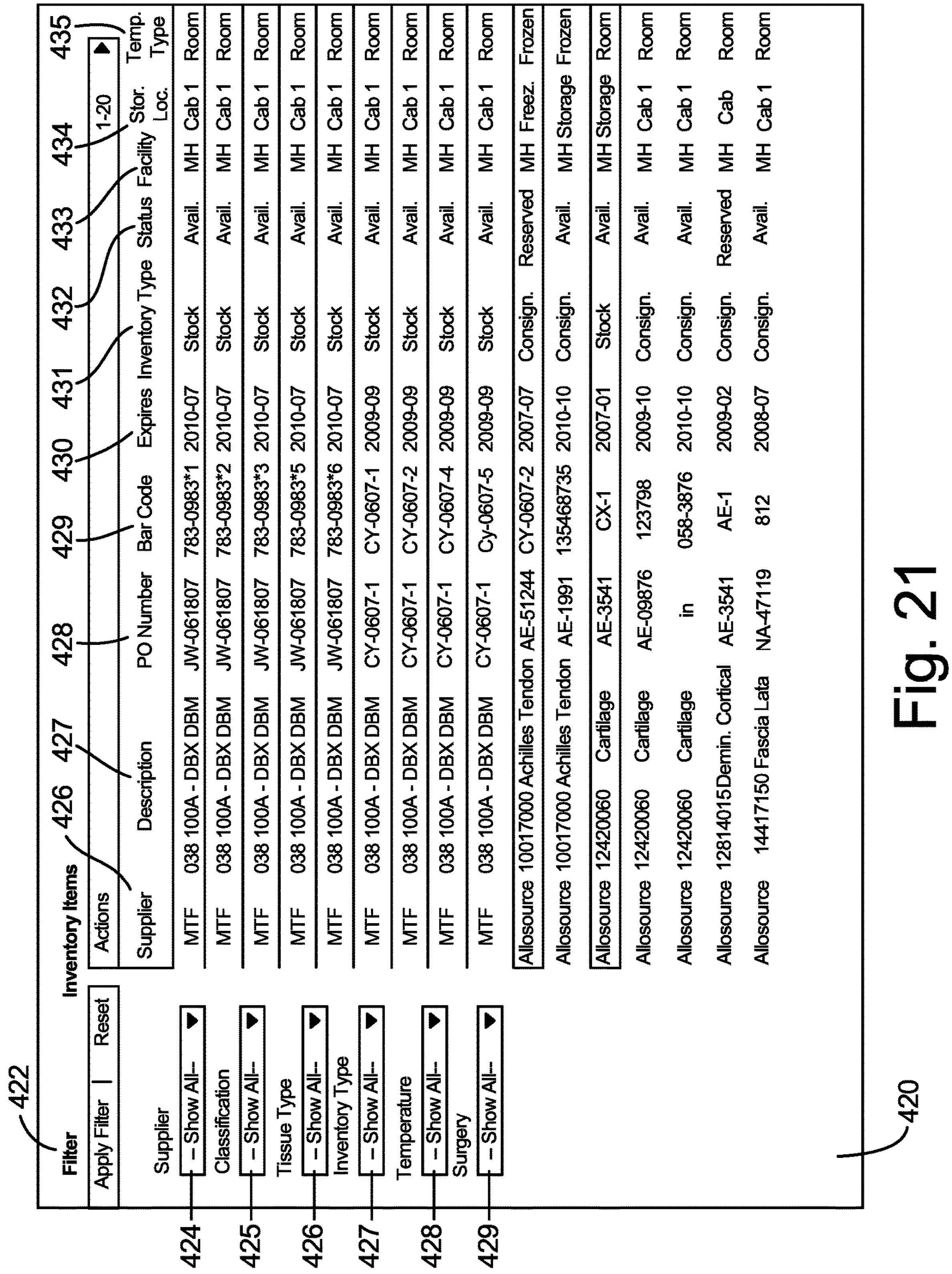

Fig. 21

Home > SOP > List > Implant

↑ Implant Tissue — 442

Filter: Patient Finder

Last Name: [    ]
First Name: [    ]
MRN: [    ]
Gender:  ○ Unknown  ○ Male  ● Female

[Search]

Search Results
- ○ Johnson, Patty (Female, 55 years)  MRN: 4-383812
- ● Vowhall, Sherry (Female, 51 years)  MRN: 2-001922 — 452
- ○ Hoffmeyer, Mary (Female, 50 years)  MRN: 1-800843
- ○ Smith, Elizabeth (Female, 30 years)  MRN: 3-554679

Patient Actions — 460
- Create New Patient
- Create New Surgery — 464
- Create New Adverse Reaction — 462
- View Profile

Surgeries

| Actions | Title | Facility Full Descript. | Start Date |
|---|---|---|---|
| ○ | Bone Cerv. Spine | MH / OR #2 | 27-Apr-2007 |
| ○ | Bone Hand | MH / OR #1 | 08-May-2007 |
| ○ | Bone Leg | MH / OR #2 | 23-May-2007 |

457 ↗   456 ↗

| Actions | Title | Bar Code Number | Tissue Status |
|---|---|---|---|

To display data in this web part, select an item in: Surgeries

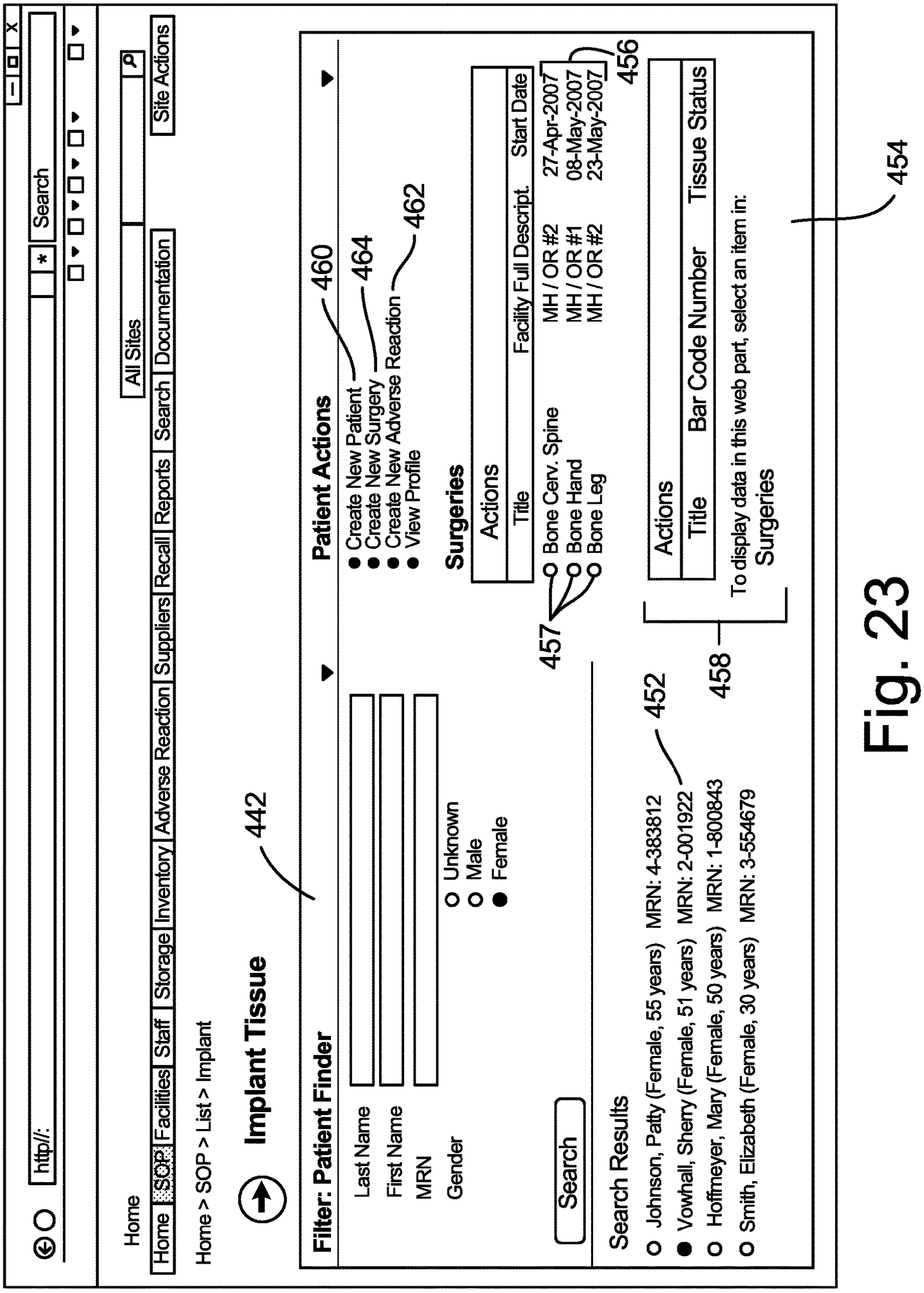

Fig. 23

Implant Tissue

Step 3: Record Implantation of Tissue(s)

Product: Allosource / Other / Other Type of Tissue /
12420060 - Costal Cartilage, >= 6.1cm Bar Code Number: 058-3876,   Lot Number: 3876, Donor/ Other ID n/a   Expiration: 31-Oct-2010

- ● Tissue was implanted successfully
- ○ Tissue was opened but not used
- ○ Tissue was explanted
- ☐ Tissue was commingled
- ☒ Tissue was used
- ☒ Remainder was discarded
  Why/ How Discarded ☒ Reconstituted per instructions — 517

Add Reconstitution Product

| Product | Procedure | Lot | Expires |
|---|---|---|---|
| ☒ Saline 0.9% | 25 min soak | 57023 | Oct-2007 |

520

Why/ How Deviated: _____ 522

☐ Tissue modified: _____ 524

Surgical Notes

[ Save Changes ]  [ Cancel ]

[ Previous ]  [ Next ]  [ Cancel ]

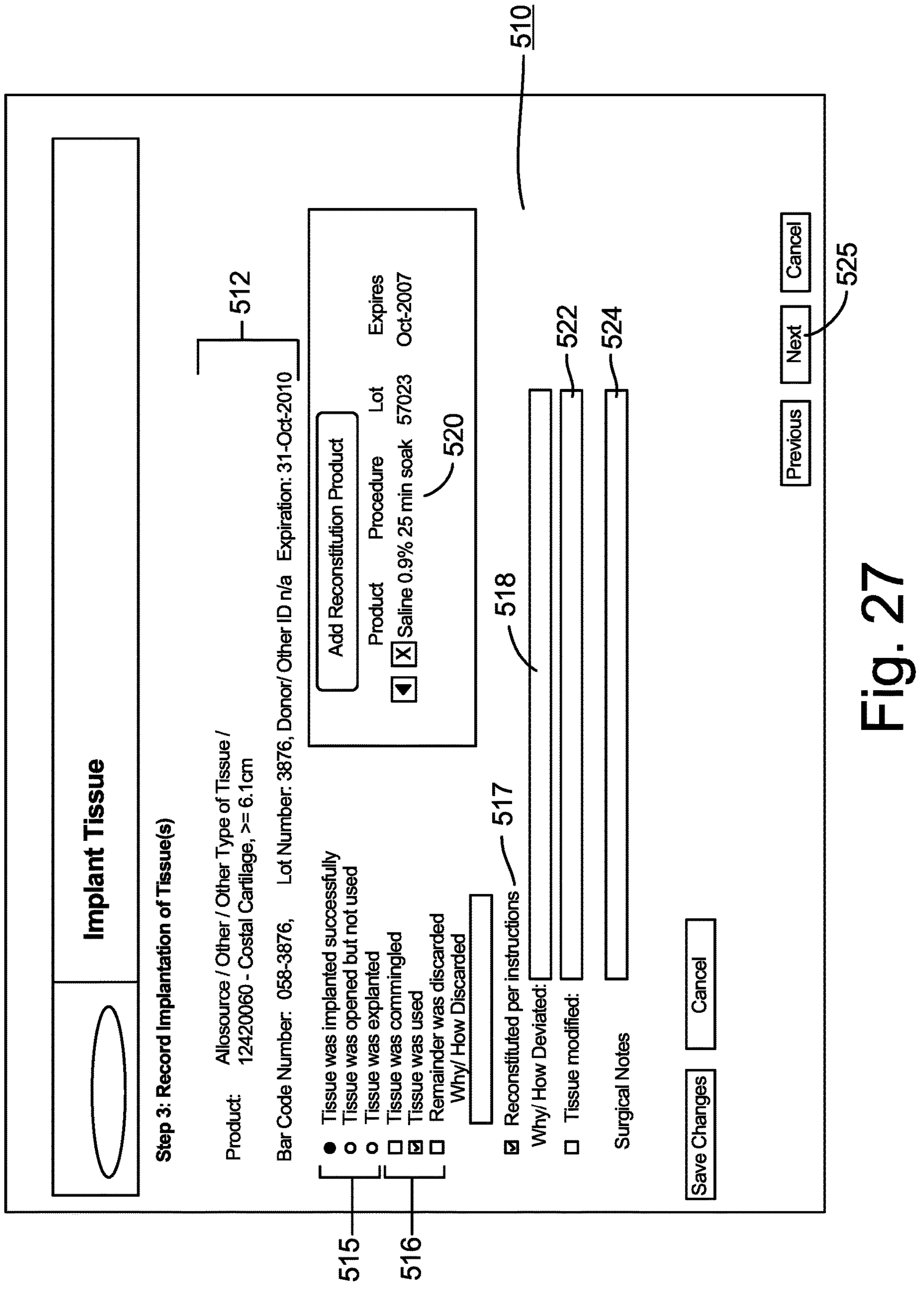

Fig. 27

Implant Tissue

Step 4: Confirm and Submit

Facility: Methodist Hospital / OR #2, Surgery Number: 984015
Procedure: Bone - Leg and Ankle / Fracture fixation - upper leg
Patient: Vowhall, Sherry (Female, 51 years) MRN: 2-001922 — 532

Start Date/Time: Monday, 08-Oct-2007 20:01
End Date/Time: Monday, 08-Oct-2007 20:01

Tissues Involved: 1    ☑ Process TUI cards after submitting — 534
Reconstitution: 1

530

[Previous] [Next] [Cancel] — 536

Adverse Reaction

Step 3: Record Initial Impressions

Patient: Vowhall, Sherry (Female, 51 years) MRN: 2-001922 — 552
Incident Date: Saturday, March 03, 2007

Bacterial - Inflammation at surgical site ▼ — 564

Notes: — 566

Add

| Type | Description | Notes |
|---|---|---|
| ☒ | Bacterial Inflammation at surgical site | |

568

560

Previous | Next | Cancel — 569

Adverse Reaction

Step 4: Record Symptoms

Patient: Vowhall, Sherry (Female, 51 years) MRN: 2-001922 — 552

Incident Date: Saturday, March 03, 2007

▶ Anaphylaxis — 572

Notes:

[ 574 ] Add

| Type |
|------|
| Notes |

☒ Fever
☒ Inflammation at surgical site — 576

Previous  Next  Cancel — 578

570

Adverse Reaction

Step 5: Review and Submit

Patient: Vowhall, Sherry (Female, 51 years) MRN: 2-001922 — 552
Incident Date: Saturday, March 03, 2007

Disposition: Open — 582

General Notes: 584

☑ Process TUI card update(s) when this form is submitted — 586

[Previous] [Next] [Cancel] — 588

580

| 2007-04-03 / Johnson | | | | | | | | All Sites | | | 🔍 |
|---|---|---|---|---|---|---|---|---|---|---|---|
| Home | SOP | Facilities | Staff | Storage | Inventory | Adverse Reaction | Suppliers | Recall | Reports | Search | Documentation | * | Search | | Site Actions |

Home > Adverse Reaction > 2007-04-03 / Johnson

| View All Site Content | **Incident Detail ▼** | | **Diagnostic Tests** — 594 | | | | | | |
|---|---|---|---|---|---|---|---|---|---|
| **Documents** | Update Incident | | New | Actions | Settings | | | | |
| ▪ Documents | Patient: | Johnson, Patty | Diagnostic Test | Ordered By | Results | Status | Date Scheduled | Date Completed | Created By | Modified By |
| **Lists** | Disposition: | Open | Lab Work-Blood Culture | | (no title) | Completed | 6/14/2007 | | Sys. Acc. | Sys. Acc. |
| ▪ Diag. Tests | Tissues: | 5 | Lab Work-Blood Culture | | (no title) | Completed | 6/14/2007 | 6/14/2007 | Sys. Acc. | Sys. Acc. |
| ▪ Compl. Actions | Notes: | | Lab Work-WBC | | (no title) | Completed | 6/18/2007 | 6/19/2007 | Sys. Acc. | Sys. Acc. |
| ▪ Contacts | MRN: | 4-383812 | Lab Work-Wound Culture | | (no title) | In Progress | 7/05/2007 | | Sys. Acc. | Sys. Acc. |
| ▪ Calendar | Gender: | F | Lab Work-WBC | | (no title) | Completed | 9/16/2007 | | spadmin. | spadmin. |
| ▪ Tasks | DOB: | Mar, 7 1952 | **Compliance Actions** | | | | | | | |
| **Discussions** | Ages: | 55 | New | Actions | Settings | | | | | |
| ▪ Team Discussion | List Procedure: | 2007, Oct-4 | Edit | Compl. Act. | Compl. To | Act. Response | Priority | Status | Assigned to | Task Group | Start Date | Resp. Req. |
| **Sites** | 592 | | Report | FDA | | | (1) High | Not Started | | | 6/14/07 | |
| **People & Groups** | | | Notify | Patient | n/a | | (2) Normal | In Progress | | | 6/14/07 | |
| Recycle Bin | | | Notify | Supplier | Potential Adv Rxn | | (1) High | In Progress | | | 6/18/07 | 6/15/07 |
| | | | Notify | Supplier | scared | | (2) Normal | In Progress | | | 6/19/07 | 6/19/07 |

596

590

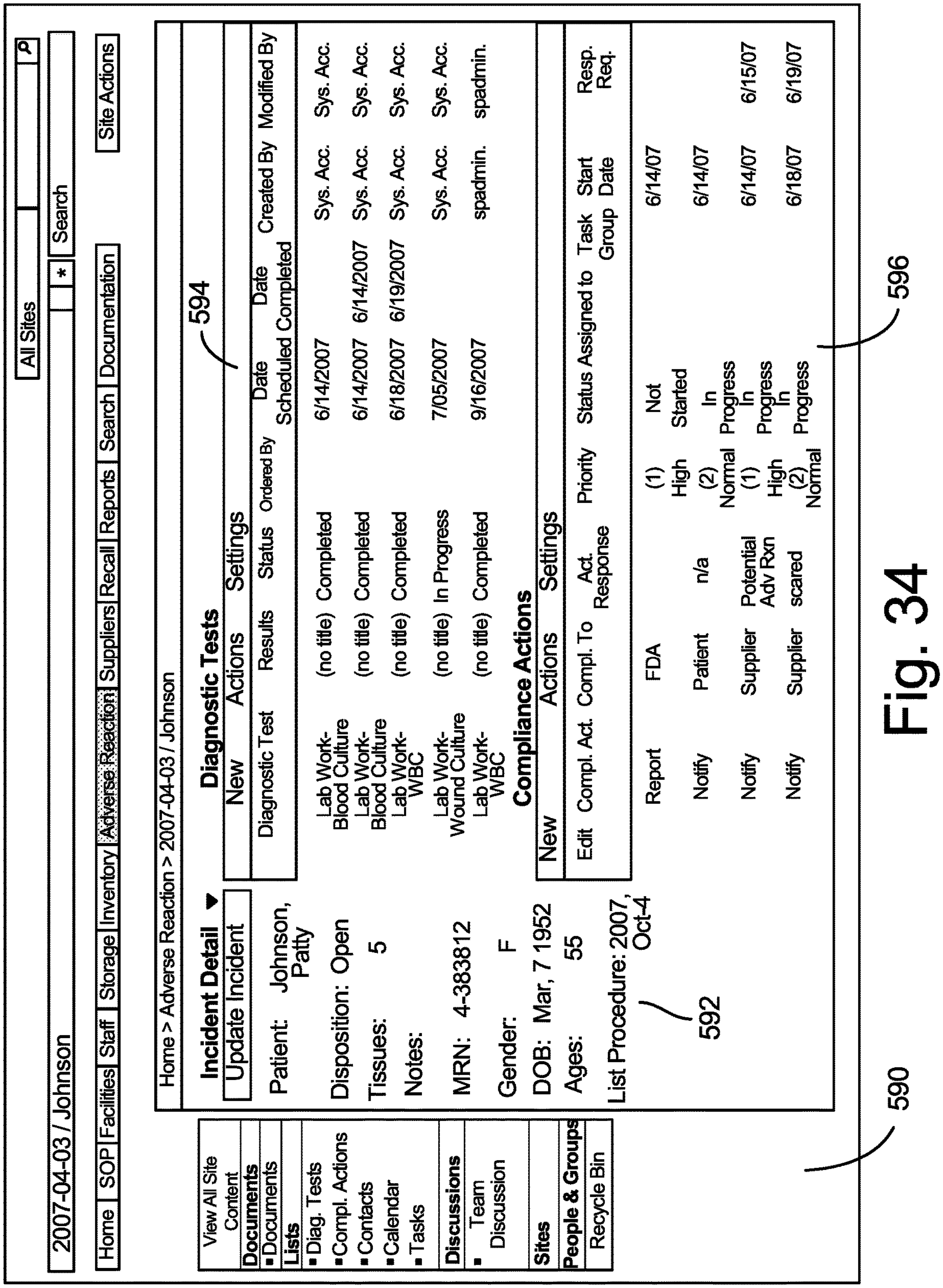

Fig. 34

Supplier Recall

Step 2: Record Identifiers

Supplier: MTF    Dated: 09-Oct-2007 — 622
Reason: Potential infection risk

☐ Use batch mode for identifiers
— 625

Identifier:  ● Bar Code Numbers (1)    ○ Lot Numbers        ○ Donor Numbers
             ○ Unique ID Numbers       ○ Serial Numbers     ○ Product Codes
— 624

Bar Code Number(s)
— 626

[ Add ]  [ Delete All ]
— 627

☒ 058-3876
— 628

[ Next ] [ Cancel ]
— 629

— 620

TISSUE MANAGEMENT SYSTEM

CROSS-REFERENCE TO RELATED APPLICATIONS

This application is a continuation-in-part of U.S. Ser. No. 11/584,357 filed on Oct. 20, 2006, which is a continuation-in-part of U.S. Ser. No. 11/540,844 filed on Sep. 29, 2006, which claims the benefit of the U.S. provisional application No. 60/826,492 filed on Sep. 21, 2006, all of which are hereby incorporated by reference in their entirety.

FIELD OF THE INVENTION

This invention relates generally to transplantable materials including cells, tissues and organ transplants ("TM"), and non-biologic implant materials, such as titanium screws and silicone breast implants ("NBI"), used within the medical field, and more specifically to a computer software-based system for ensuring the safe and appropriate handling of such TM and NBI from receipt to their use in surgical procedures and tracing such TM and NBI later in response to an adverse reaction investigation or recall. The computer software-based system provides for tracking the movement of NBI from receipt into a medical establishment facility to their use in a surgical procedure.

BACKGROUND OF THE INVENTION

The human body is made up of trillions of cells that allow it to function, grow, heal and defend itself against hundreds of diseases. Cells of the same type combine to form tissues. Examples of tissues include: connective tissue which helps to support and join together various parts of the body; epithelial tissue which acts as a covering for external and internal body surfaces; muscle tissue which consists of threadlike fibers that can contract to make movement of the body possible; and nervous tissue which carries signals to permit various parts of the body to communicate with each other.

An organ consists of multiple tissues working to perform a particular function. For example, connective, epithelial, muscle and nervous tissues all combine to make up the heart which pumps blood throughout the body. The body's skin, skeletal, muscular, digestive, respiratory, circulatory, urinary, lymphatic, endocrine and nervous systems are all formed from multiple organs that in turn are made up of several different kinds of tissues.

When tissues or organs are damaged or diseased, healthy cells, tissues, or organs from one person may be transplanted to replace the diseased, damaged, or destroyed tissue or organ in another person. Blood transfusion is the most common type of tissue transplanted. After blood products, the most common transplant from person to person (allogeneic) is cadaveric tissue: e.g., bone, tendons, skin, cornea, heart valves and blood vessels. There are more than a million tissue transplants a year; most of these are bone and other musculoskeletal tissues, and in many cases involve some form of a NBI. For instance, bone transplants are commonly used in spinal surgery and the transplanted bone attracts new bone formation and eventually becomes an indistinguishable part of the recipient's bone (osteoinductive). There are various devices that can be used as structural grafts: cages to hold bone grafts or bone substitutes, such as bone graft extenders, demineralized bone matrix ("DBM"), and autogenous bone. NBI, such as titanium or carbon-fiber cages, or resorbable cages or screws, may help to anchor and support the implanted bone, and provide osteoconduction. Cornea transplants improve the vision of the patients whose corneas have become scarred by injury or clouded by age or infection. Skin transplants can be used to temporarily cover areas of the body of burn victims to reduce the risk of infection, prevent the loss of fluids and decrease pain until skin from another part of the patients own body can be utilized for a more permanent transplant. Bone marrow transplants replace the blood-forming tissue within a patient's bones to treat certain kinds of cancer and serious blood disorders.

Tissues are usually isolated and processed for easier use in surgical procedures. For example, whole bones can be used in transplant, or bones can be cut into various shapes or powdered for use in filling voids. Bones from different areas of the body can be combined and processed by proprietary methods into new products designed for unique uses in surgical procedures.

Some tissues can be treated more harshly than others, and the processing methods will determine the likelihood that a tissue product carries an infectious risk. Tissues such as bone that are treated with alcohol, oxidative agent or irradiation have very low or non-existent risks, but some surgeons are reluctant to use these for fear that the functionality of the product has been compromised. Use of antibiotics does not guarantee that bacteria have been totally removed from the graft and have no effect on viruses.

The heart, lungs, kidney and liver are commonly transplanted organs. Such transplant procedures can enhance the quality of life for some patients and restore the health of people who may otherwise die. Some organs like the heart and lungs cannot survive outside the body for more than a couple of hours. Thus, they usually are transplanted quickly from a patient who has been declared brain dead and surviving only by mechanical means in order to perfuse the organs until they can be transplanted to the matched recipient patient in need. Organ registries have been established in many states and countries to identify and prioritize transplant patients in need of an organ. Their position on the registry list will typically determine, when, if ever, they can qualify for a transplant. Many tissues like bone, corneas and skin, however, can be held for longer periods outside the human body. Such tissues can be stored for future transplantation or implantation in refrigerators or freezers at independent tissue banks or tissue processors, and subsequently distributed to storage units within hospitals.

Infection from contaminated grafts is the greatest risk from transplantation. Tissue and organ transplantations have been associated with risk from HIV, hepatitis, bacterial infections, prion associated diseases such as Creutzfeldt-Jakob Disease ("CJD"), rabies, fungus infections, West Nile virus, leucocytic choriomeningitis, as well as many others. Any transplant operation carries the risk of rejection by the body's immune system or infection. Surgeons try to prevent rejection by choosing a donor with the same blood type as the recipient patient. Matching HLA antigens between the donor and recipient may also be important for kidney and bone marrow transplants. Immuno-suppressive drugs like azathioprine, prednisone and cyclosporine are also commonly given to the transplant patient to help prevent tissue or organ rejection. Because such immuno-suppressive drugs act to reduce immune activity within the patient, they may also hinder the body's ability to defend itself against infections.

Improper handling of the cells, tissues or organs prior to their use in the transplant operation can adversely impact their functionality once implanted in the patient, or greatly increase the likelihood of an infection or other adverse reaction by the patient. For example, the TM may be stored at the incorrect temperature or outside a sterile environment. The packaging surrounding the TM may become perforated. Prior to surgery, TM may be improperly reconstituted. Blood and tissue banks are typically better than surgical units in hospitals at establishing some procedures for storing cells, tissues; however, once these materials leave their facilities, the safety system can deteriorate rapidly. Hospitals rarely have established policies and procedures for receiving, handling, storing and reconstituting tissues before their use in surgery. Instead, they allow a great deal of individual discretion to the hospital physicians and nurses for these critical activities. Consequently, standards and procedures can differ greatly across the hospital staff to the potential detriment of the patient.

Many hospitals perform no qualification of the donor sources of tissue that they use in surgical procedures. To the extent that the hospitals institute any certification process for their tissue suppliers, the process tends to be directed to issues of price and delivery schedule, instead of whether the supplier is properly registered, licensed, and compliant with prevailing industry safety standards. It is as if tissue is just another form of paper clips that need to be stocked in the hospital's inventory. Suppliers of tissue have even been known on occasion to bring these critical tissues in their car trunks to the hospital operating room without monitoring storage conditions.

While hospital surgical departments may possess refrigeration units for storing tissue, their staffs frequently do not know how to monitor and control the equipment. Moreover, few surgical units possess the necessary training to reconstitute tissue. The blood bank and surgical units within the hospital may possess individual staff members with knowledge but they are outside of each other's control.

All of these problems can lead to adverse reactions, including serious infections, illnesses and even death for the transplant patient. For example, a healthy, 23-year-old Minnesota student underwent a routine, elective knee surgery in 2004 in which cartilage sourced from a cadaver via a reputable tissue bank was used by the surgeon to repair the knee. Unbeknownst to the surgeon, the corpse sat unrefrigerated for 19 hours, and had been rejected by two other tissue banks. The cartilage also had not been adequately treated to kill bacteria. The student died four days after the surgery from a raging infection.

In another reported case, a California man died in 2006 from the effects of a fungus-infested heart valve that had been recently implanted. Indeed, the United States Food and Drug Administration reports that 207 deaths occur each year from fungus-contaminated heart valves alone.

When such an incident occurs, good medical practice and public health policy requires an immediate investigation of the patient's condition to determine whether the infection, illness or death was caused by the tissue, organ, NBI, or surgical procedure, as opposed to an independent condition in the patient. If the surgical procedure was faulty, then the transplant procedure needs to be traced back to the surgeons and nurses involved, the operating room environment, and the equipment involved to reduce the likelihood of a repeat event. If it was traced back to a NBI malfunction or manufacturing defect, then it needs to be traced back to the supplier. If the TM was the cause, then it needs to be traced back to the donor or supplier so that other TM from the same source is immediately removed from inventory and other patients who are transplant recipients of similar TM from the same supplier or donor can be warned and provided appropriate medical care and counseling. Yet, such a tracing process is frequently impossible because many hospitals fail to log in the TM and NBI that they receive from suppliers and track their use in surgical procedures. Quality problems in hospitals culminated in 2005 when there was a major recall of tissue products inappropriately released by several tissue banks. Yet, repeated attempts to locate tissue products at hospitals that had not been transplanted failed miserably, thereby resulting in other patients receiving potentially contaminated tissue products. During the same recall, hospital protocols for tracing recipients of the potentially contaminated products were found to be substantially inadequate or entirely absent. Close to one year later, there are recipients yet to be identified who have not received appropriate diagnostic treatments and modalities.

In one incident reported within the industry, organs provided by a donor institution resulted in several cases of hepatitis C in the transplanted patients. Because the hospital failed to notify the tissue bank for 16 months, other infected patients were deprived of treatment while this disease could be treated, resulting in additional deaths. A $32 million damage award resulted from a subsequently filed litigation.

In addition, there have been reported cases of physicians taking diseased tissue from in-hospital patients and transplanting it into unsuspecting, healthy patients. These tissues have not been able to be tracked back to the original source, resulting in the recipient's death.

The transplant industry relies upon "tissue usage information cards" that a hospital is supposed to return to the issuing tissue bank after a surgical procedure is completed. Such cards allow the tissue bank to monitor usage of their tissue and notify everyone who has received similar tissue for recall purposes. However, hospitals only return 50-85% of these cards to the tissue banks.

In the case of adverse reaction investigations, hospitals do not usually define what constitutes an adverse reaction and therefore what should be reported. Instead, the reporting responsibility is left to the physician's discretion. Physicians often resort to a gram stain test or cultures on the tissue prior to surgery. But, such test results can be misleading and grossly inadequate to detect diseased tissues.

There are associated risks with tissue transplantation. There are numerous reports of transplant-transmitted infections, including some that resulted in death. For example, there was a recent article (Morbidity and Mortality Weekly Report 2002 ("MMWR"); 51 (March $15^{th}$): 207-210) that reported that on Nov. 7, 2001, a 23-year-old male from St. Cloud, Minnesota had knee surgery using a refrigerated "fresh" femoral condyle. On Nov. 10, 2001, the patient developed knee pain and severe hypotension. On Nov. 11, 2001, the patient died from clostridium sordelli sepsis that came from the tissue transplant. On Nov. 13, 2002, a 17-year-old male in Illinois also received a "fresh" femoral condyle and meniscus from the same donor. On Nov. 14, 2002, the patient developed a fever and septic arthritis. The presumed cause was a clostridia infection. Likewise, usage of antibiotics in patients prior to surgery can mask problems contained in tissues.

Because of these abuses and other safety problems within hospital and tissue bank environments, regulatory and standard setting agents like the Joint Commission for the Accreditation of Health Care Organization ("JCAHO"), American Association of Blood Banking ("AABB"), Food & Drug Administration ("FDA"), and the College of American Pathologists ("CAP") are currently implementing mandates for the safe handling, storage, use, and tracing of TM. However, these mandates provide no instructions or guidelines to the hospital or tissue bank for how to comply.

Therefore, such hospitals and tissue banks are left with regulatory and legal liability for their failure to comply, but no tools to use to comply.

Some instances of tissue tracking are reported in the prior art. Thus, U.S. Published Application No. 2005/0262088 filed by Solis et al. discloses a system for organ procurement and transfer. While this system maintains the security of patient information, it does not address the safety of the organ or organ match for the patient.

U.S. Published Application Nos. 2005/0010437 and 2005/0010449 filed by Abukwedar teaches an organ donation system that permits a person to donate or agree to donate one type of organ in order to be accorded preferential receipt of another organ. This exchange program, however, does nothing for tracking the safe receipt, handling, or use of the organ, or tracing its use after surgery.

U.S. Published Application No. 2005/0285715 filed by Comunale discloses a container with an electronic lock controlled by a computer system for carrying blood samples or organs to a hospital in a secure manner. While this transportation container can prevent theft or contamination of the organ by strangers, it does nothing to prevent unsafe handling, storage, or treatment by the hospital of the organ.

Other prior art systems exist within a diagnostic laboratory, for tracking biological samples. Thus, U.S. Published Application No. 2003/0120633 filed by Torre-Bueno assigns unique bar codes to samples that can be scanned and read during processing of the sample within the lab. U.S. Pat. No. 5,416,029 issued to Miller et al. employs color-coded embedding media and corresponding color-coded slides accompanied by words, numbers, or symbols to identify the biological samples. U.S. Pat. No. 5,842,179 issued to Beavers et al. discloses a cryogenic freezer with a security key pad for receiving and tracking information to identify the location of blood and tissue samples stored within the freezer, and when a capsule has been removed from the freezer. While these types of systems may be useful for keeping track of thousands of biological samples stored within a diagnostic laboratory, they do nothing to ensure the safe handling, storage, and treatment of the sample within the lab.

Other prior art references disclose systems for keeping track of the whereabouts of surgical supplies used during surgery to detect if they have been accidentally left inside the patient after surgery. See, e.g., U.S. Published Application No. 2002/0049650 filed by Reff, and U.S. Pat. No. 6,861,954 issued to Levin. U.S. Published Application No. 2002/0082957 filed by Krassi specifies an inventory control system for chemical reagents used within a clinical or diagnostic lab. Such inventory control tracking systems can detect the location or number of products, but once again, they do not address the proper handling and storage of those products.

A comprehensive system for tracking the appropriate handling, storage and use of tissues throughout the tissue bank's or hospital's chain of custody of the materials would be beneficial. Also advantageous would be a system that reliably enables the tracing back of tissues from patient to supplier after an adverse reaction is detected. For tissue and blood banks and larger healthcare providers, this system would ideally be computerized due to the comparatively large number of TM that need to be processed and handled.

Indeed, computer systems are used within the healthcare industry to store, monitor, and track patient information. The hard drives of such computer systems can store large volumes of data which can be password-protected. National home health agencies, hospitals and medical clinics can afford to employ large computer systems run on "point of care" software that permit the clinician to call upon a file containing the medical chart for a patient from the computer's hard drive, review the patient's initial physical assessment, clinical procedures and medicines administered in the past, and update the file for any new clinical procedures or medicines prescribed. Such computer software systems provided by companies like 3M Corporation, Care Package, and St. Louis Software are readily accessible by different doctors or nurses at the hospital or clinic. However, such point-of-care software systems are necessarily complex because of the large number of patients and clinical staff required to access the information It is not uncommon for such programs to require expensive database platform servers and cost upwards of $100,000.

Other computer software systems are known within the industry for assisting the administration of medical care. For instance, U.S. Application 2004/0186746 filed by Angst on Sep. 23, 2004 discloses a USB flash memory device that permits a user to carry his personal medical records with him and launch it on the hard drive of any computer. The information contained within the flash memory device can be protected via a password or encryption. In this manner, the user has accurate medical records for himself when he visits the doctor, or in case of a medical emergency.

Computerized information devices can also be used to monitor a patient in the field. U.S. Application 2004/0117207 published by Brown on Jun. 17, 2004 teaches a handheld microprocessor device used by a patient to monitor and store, e.g., blood glucose level data. This information can then be transmitted to a doctor at a remote location and downloaded by the doctor onto a computer for storage or to produce medical reports.

Many patients do not actually visit a hospital, medical clinic, or doctor's office for medical care due, e.g., to a loss of mobility or frequency of required care. Thus, the doctor or nurse may visit the patient at her home. In such cases, the medical practitioner is away from his office where the medical records, medical treatises and studies, etc. reside. Therefore, U.S. Patent Application 2004/0249666 published by Napolitano et al. provides a healthcare computerized system that provides medical practitioners with best practice patient disease diagnosis and treatment information. In essence, it enables the medical practitioner to carry a bookcase of medical treatises and published studies with her. The practitioner can use this portable information to diagnose and treat the patient in the field.

U.S. Patent Application 2005/0027567 published by Taha on Feb. 3, 2005 on the other hand discloses a data management system containing a field module used by the medical practitioner to collect data for the patient and communicate it back to a server at the home office for use by a doctor or nurse to tell the field practitioner what steps to take to treat the patient. The patient can also use this field module to communicate with his caregiver back at the medical office. See also U.S. Application 2002/0194029 published by Guan et al. on Dec. 19, 2002, which discloses a medical information management system that permits a medical practitioner to carry a patient's medical records with him in image form in the field, consult medical on-line databases, and communicate remotely with other members of the medical staff.

Computer systems are also widely used for dispensing medicines in hospitals via, e.g., an infusion pump. See U.S. Application 2005/0065817 published by Mihai et al. on Mar. 24, 2005; 2005/0055244 published by Mullan et al. on Mar. 10, 2005; and 2005/0055242 published by Bello et al. on Mar. 10, 2005. Such systems typically track and monitor the patient's symptoms to indicate how the administered drug is affecting the patient.

These information management systems available within the healthcare industry typically focus upon "point of care" for the patient, keeping track of all the clinical data for treatment of that patient. At least one computer system is also available from Owens & Minor within the healthcare industry for tracking TM. However, this system provides essentially the same functionality as conventional paper records systems. It does not permit queries directed to TM data, does not track the healthcare institution's processing and handling of the TM, and provides no mechanism for prompting or enabling the healthcare institution to investigate an adverse reaction occurring in the patient. Likewise, large national blood banks use computerized systems to track their massive inventories of blood samples. Such systems keep track of the blood type of each sample, so that a blood sample is not supplied to a patient with an incompatible blood type. Such systems will also provide advice regarding which blood types are compatible and which ones are not from a safety stand point. However, these blood bank computerized systems represent little more than inventory systems without any functionality for tracking the processing and handling of the blood samples.

Thus, a comprehensive computerized system that permits the tracking of the appropriate handling, processing, storage, and use of tissues throughout the tissue bank's or hospital's chain of custody of the materials would be beneficial, particularly if its built-in functionality prompts staff members of the tissue bank or hospital to record necessary data and properly handle, process, store, and use the tissue or organ product. Such a computerized system would also be advantageous if it provides a search or query functionality that reliably enables the tracing back of tissues from patient to supplier after an adverse reaction is detected, or the tracing forward of the TM or NBI material from supplier to patient or hospital in the event of a product recall that is issued by the supplier or the Food and Drug Administration.

SUMMARY OF THE INVENTION

The present invention provides a comprehensive tissue management system for transplant materials like tissues, organs, and non-biologic implants. The tracking portion of the system verifies that staff members of a medical establishment like a hospital have handled, stored, transported, reconstituted, and used the tissue, non-biologic implant, or organ materials in a safe and regulatory-compliant manner from the point of receipt to the point of issuance or surgical use throughout the hospital's organization. Such a system is preferably computer-based, and it should preferably be structured to provide appropriate prompts to the staff members to take the necessary actions to handle, store, transport, reconstitute and use the tissue or organ materials in a safe or appropriate manner. Even more preferably, such system will not permit such staff members to carry out a critical step for handling, storing, transporting, reconstituting or using such tissue, non-biologic implant, or organ material unless data has already been entered into the system to verify that a prior critical step has been taken.

The tracking portion of the system creates an integral record that documents which hospital staff members have provided which processing steps to the tissue, any associated materials used in conjunction with such tissue, and an identification of the tissue that was transplanted or implanted inside a patient, so that the tissue can be reliably traced back to its donor or tissue bank source in the event of an adverse reaction by the patient after the surgery, or the tissue or organ can be traced in response to a warning received from the donor or tissue bank. Such adverse reaction investigation is preferably conducted utilizing medical cladistics to identify risk clades. Again, such system, preferably computer-based, should be structured to provide prompts to the medical establishment's staff members to record and enter the data at the same time that the processing activity is carried out in order to create accurate, comprehensive and contemporaneous record-keeping. Such system preferably will refuse to permit the staff members to enter data into the system for a critical processing step unless data from a previous critical processing step has already been entered.

BRIEF DESCRIPTION OF THE DRAWINGS

In the accompanying drawings:

FIG. 5 is an interactive graphic user interface illustrating a certified suppliers list screen.

FIG. 6 is an interactive graphic user interface illustrating a supplier information subscreen.

FIGS. 7-9 are interactive graphic user interfaces illustrating tissue order screens.

FIG. 10 is an interactive graphic user interface illustrating a catalog page accessible within the comprehensive tissue management system for defining available supplier products.

FIGS. 13-16 are interactive graphic user interfaces illustrating tissue receiving screens.

FIGS. 18-20 are interactive graphic user interfaces illustrating tissue transfer screens.

FIG. 21 is an interactive graphic user interface illustrating a tissue inventory screen.

FIGS. 22-28 are interactive graphic user interfaces illustrating tissue implant screens.

FIGS. 29-34 are interactive graphic user interfaces illustrating tissue adverse reaction investigation screens.

DETAILED DESCRIPTION OF THE PREFERRED EMBODIMENT

Figure 1:
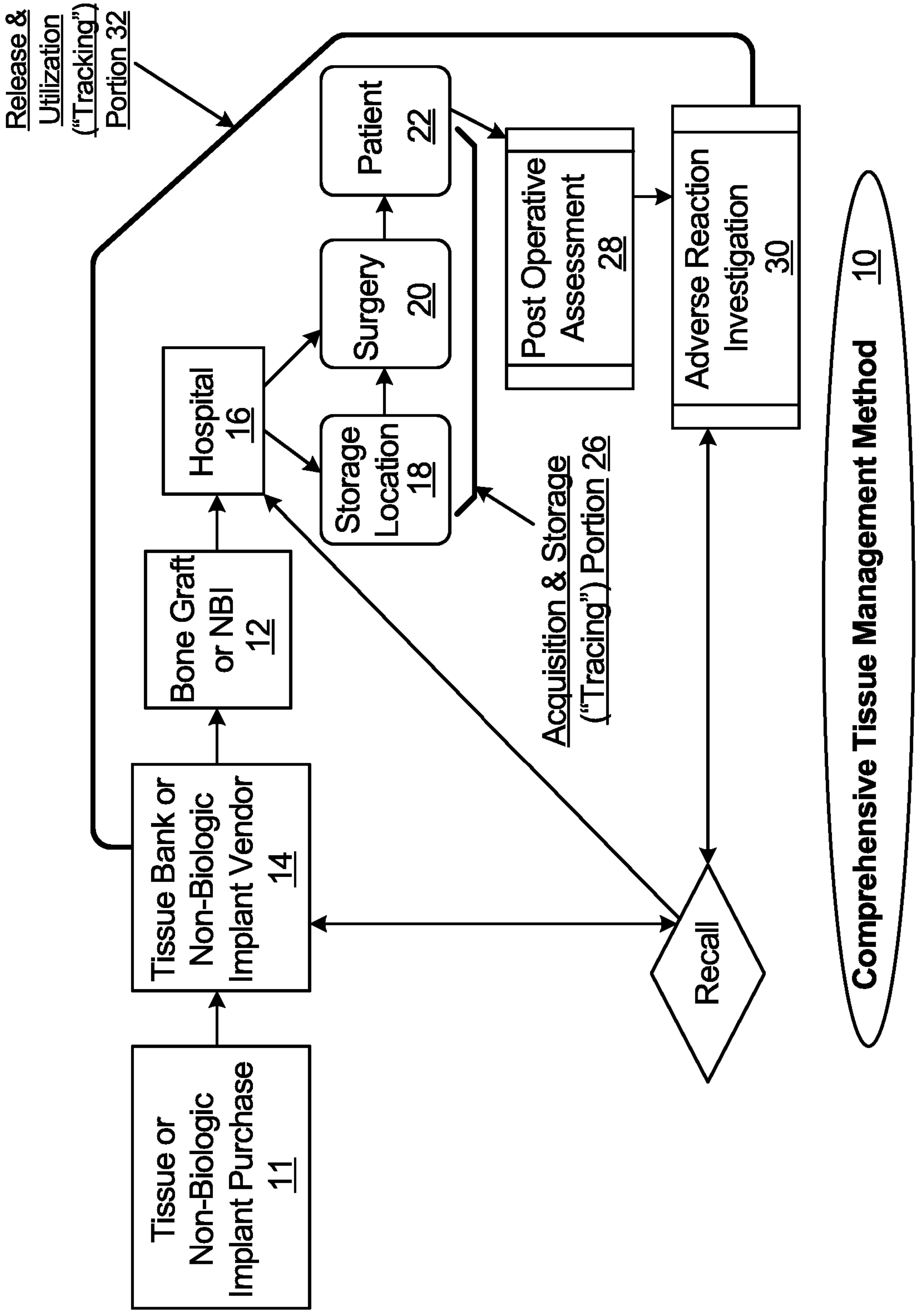
FIG. 1 is a schematic illustration of a process flow for the transfer and use of transplantable material within a clinical environment.

A comprehensive system for safe management of transplantable material is provided by the invention. In its preferred embodiment, the system is computer-based. Such invention enables the proper qualification of suppliers; logging and inspection of incoming transplantable material; product maintenance; integrated tracking and verification of the handling, storage, and use of transplantable materials in a safe and regulatory-compliant manner from the point of receipt to the point of issuance/final disposition throughout the medical establishment. The system also provides for prompt investigation of any adverse reaction suffered by a patient who receives the transplantable material through a surgical procedure. Additionally, it ensures a complete documented history of the transplantable material within the medical establishment so that the transplantable material can be traced back to its supplier in the event that a product recall of transplantable material is warranted either by a supplier or a regulatory agency. This allows a timely identification, notification and treatment of other patients receiving similar transplants.

The system of this invention is tailored to the specific medical establishment and its handling and use of transplant materials, so as to enhance the integrity of the system. Moreover, the system prompts staff members of the medical establishment to carry out the necessary steps for the safe and appropriate processing of the transplantable material and to record the associated data at the time that the activity is conducted. More preferably, the system will not allow data entry for a critical processing step unless the data from a prior critical processing step has already been entered. In this manner, the system provides a self-auditing function to enhance the integrity of its tracking and tracing functionalities.

For purposes of the present invention, "transplantable material ("TM")" means human cells, tissue, or organs intended for implantation, transplantation, infusion, or transfer to a patient, including, but not limited to: musculoskeletal tissues like bone, tendons, fascia, ligaments, cartilage, and bioengineered bone products; skin; cardiovascular tissues like heart valves, arteries, veins, and pericardium; reproductive cells like sperm, semen, oocytes, fertilized eggs, and embryos; cellular therapies like stem cells, progenitor cells, cord blood, placental blood, chondrocytes, bone marrow, and neural cells; dura mater; breast milk; eyes; corneas; organs; islet cells; parathyroids; autologous tissue; and synthetic and xenographic tissue used as replacements for human tissue. For purposes of this application, transplantable materials also include non-biologic implants ("NBI"), including but not limited to: titanium screws, titanium or carbon-fiber cages or resorbable cages, fixation systems, saline or silicone breast implants, synthetic polymers, prosthetic hips, knees and other joint combinations thereof. Transplantable material also includes surgical instruments, equipment, reagents, supplies, and other materials associated with the transplanting or implanting of any transplant material into a patient.

In the context of the present invention, "medical establishment" means any organization directed to the storage, research, transplantation, or implantation of transplantable materials, including but not limited to hospitals, medical clinics, surgical centers, fertility clinics, blood banks, tissue banks, organ donor banks, university and research facilities, diagnostic laboratories, and willed body programs.

As used within this application, "supplier" means any person or entity that provides a transplantable material to a medical establishment on a profit or non-profit basis, including but not limited to live or deceased organ donors, tissue banks, blood banks, fertility clinics, laboratories, and manufacturers of synthetic or bioengineered tissue, NBI, or organ products.

For purposes of the present invention, "patient" means any recipient by transplantation or implantation of a transplantable material, including without limitation humans, domesticated animals like dogs, cats, and horses, and working animals like bulls and horses.

As used within this application, "adverse reaction" means any undesirable effect or untoward outcome consequent to or reasonably related to the transplantation or implantation of transplantable material into a patient, including but not limited to disease transmission, other infectious complications like fever or wound infection attributed to the graft or positive culture of the graft at the time of use, immune rejection, and unexplained synovitis following tendon implant.

A freeze-dried bone graft implanted into a human patient will be used as an exemplary transplantable material for purposes of describing the comprehensive tissue management system of the present invention in this application. It is important to appreciate, however, that any other type of transplantable material (tissues, cells, NBI, or organs) or patient is covered by this application, as well.

FIG. 1 shows the history of a transplantable material from purchase order to entrance into the hospital to the final implantation in a patient, and investigation of adverse reactions. When a surgeon is in need of a bone graft 12, the hospital 16 will acquire it from a tissue bank 14 by placing a purchase order 11. The bone graft 12 will be acquired by hospital 16 in accordance with the terms of its supply agreement with the tissue bank 14. Once the bone graft 12 is delivered to hospital 16 by tissue bank 14, it will typically be stored by the hospital. The location of storage 18 varies by hospital. It can include the blood bank, surgical department, central supply, etc. until the bone graft is needed by the hospital's surgical department 20 for implantation into patient 22. The comprehensive tissue management tracking portion 26 of the present system prompts the hospital staff to undertake all of the activities necessary for the safe handling, storage, reconstitution, and implantation of the bone graft 12 in accordance with regulatory requirements and industry standards from the point of receipt by the hospital 16 until the bone graft is implanted into patient 22, and collects the necessary information to document the staff's compliance therewith.

Once the bone graft 12 has been implanted into the patient 22, the medical establishment's responsibility to the patient is not complete. Instead, the surgeon or other staff member of the hospital 16 needs to perform a post-operative assessment 28 of the patient's condition to determine whether any adverse effect like infection caused by the bone graft or surgical procedure has occurred. The hospital then notifies the tissue bank by usage of the tissue utilization information card ("TUIC") to whom the tissue was implanted. If an adverse reaction occurs, then an investigation 30 needs to be promptly commenced to determine whether the adverse reaction was caused by the bone graft, the surgical procedure, the reagents used to reconstitute the bone graft, or some independent condition of the patient 22. The comprehensive tissue management tracing portion 32 of the present system enables the reliable tracing of the bone graft back to the tissue bank 14 in the event of an adverse reaction investigation 30, or the tracing forward of the bone graft 12 to the patient 22 or the storage inventory location 18 in the event that tissue bank 14 or a regulatory agency like the FDA issues a recall or other warning.

The comprehensive tissue management system tracing 26 and tracking 32 portions of the present invention must have compiled a sufficient documentary history of the bone graft throughout its life in the hospital to enable the investigation to identify each aspect of the handling, storage, reconstitution, and surgical implantation of the bone graft 12 back to tissue bank 14 as the supplier in the event that a recall of other transplantable material from the same donor is necessary. Determination of medical treatment of other patients receiving such similar tissue products must be conducted.

Figure 2:
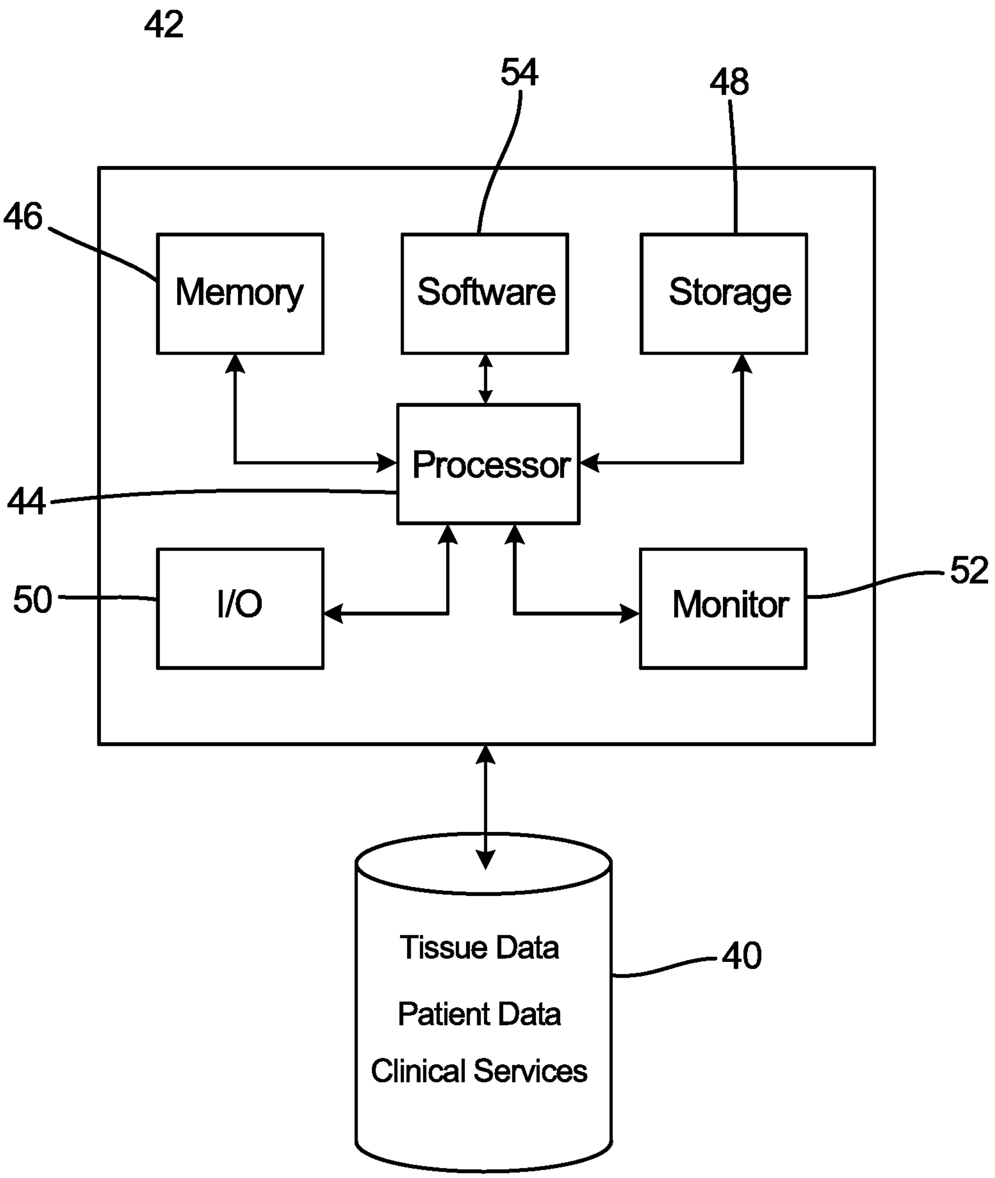
FIG. 2 is a flow diagram illustrating an example embodiment of a system for managing a comprehensive tissue management method and recording information related thereto.

Referring to the example embodiment of FIG. 2, the comprehensive tissue management system 10 comprises a general programmable computer 42 having a central processing unit ("CPU") 44 controlling a memory unit 46, a storage unit 48, an input/output ("I/O") control unit 50, and at least one monitor 52. Computer 42 operatively connects to database 40, containing, e.g., tissue data, patient data, and clinical services data. It may also include clock circuitry, a data interface, a network controller, and an internal bus. One skilled in the art will recognize that other peripheral components such as printers, drives, keyboards, mice, barcode scanners, and the like can also be used in conjunction with the programmable computer 42. Additionally, one skilled in the art will recognize that the programmable computer 42 can utilize known hardware, software, and the like configurations of varying computer components to optimize the storage and manipulation of the data and other information contained within the comprehensive tissue management system 10. This computer system can be located on premise at a facility, or in a hosted environment through, e.g., the Internet.

Referring to FIG. 2, comprehensive tissue management system 10 includes a software program 54 having a plurality of graphic user interfaces ("GUIs") that permit the input of data concerning the patient 22, the purchase order 11 placed for the bone graft 12, and the receipt, storage, handling, transport, reconstitution, and surgical use of the bone graft with respect to patient 22. Data may also be inputted with respect to the post-operative assessment 28 of the transplant or implant, and any adverse reaction investigation 30 resulting therefrom. Outputs produced by such software program 54 include search results directed to the bone graft 12, its current location in storage location 18 or the patient 22 into which it was transplanted or implanted, and all processing steps carried out with respect to the bone graft and which staff members conducted those processing steps. The software program 54 can also produce and print a series of reports documenting this information.

The GUI can also be used to display the status of the transplantable material to any or selected staff members participating in monitoring the transplantable material. Additionally, the comprehensive tissue management system, computer system, and GUI can be connected to external devices such as refrigeration units to send a current temperature reading or to notify those monitoring the tissue that the temperature of the refrigeration unit has decreased or increased beyond a predetermined range. The comprehensive tissue management system, computer system, and GUI can be connected to any type of device that needs to be monitored.

Data may also be inputted with respect to the post-operative assessment 28 of the transplant or implant, and any adverse reaction investigation 30 resulting therefrom. Outputs produced by such software program 54 include search results directed to the bone graft 12, its current location in storage location 18 or the patient 22 into which it was transplanted or implanted, and all processing steps carried out with respect to the bone graft and which staff members conducted those processing steps. The software program 54 can also produce and print a series of reports documenting this information.

The software program 54 may be designed to be an expression of an organized set of instructions in a coded language. These instructions are programmed to facilitate the monitoring of the transplantable material from at least the point of sourcing, handling, transportation, storage, reconstitution and/or surgical implantation. The instructions may include the entry, reporting and/or reading of data relating to time, date, location, temperature, condition of the tissue, and/or any other information needed for monitoring the transplantable material.

The computer system on which the system resides may be a standard PC, laptop, server, handheld wireless device, or any automated data processing equipment capable of running software for monitoring the progress of the transplantable material. The CPU controls the computer system and is capable of running the system stored in memory. The memory may include, for example, internal memory such RAM and/or ROM, external memory such as CD-ROMs, DVDs, flash drives, or any currently existing or future data storage means. The clock circuit may include any type of circuitry capable of generating information indicating the present time and/or date. The clock circuitry may also be capable of being programmed to count down a predetermined or set amount of time. This may be particularly important if a particular type of tissue needs to be refrigerated or implanted in a predetermined amount of time.

The data interface allows for communication between one or more networks which may be a LAN (local area network), WAN (wide area network), or any type of network that links each party handling the tissue. Different computer systems such as, for example, a laptop and a wireless device typically use different protocols (i.e., different ways to coordinate communication). To allow the disparate devices to communicate, the data interface may include or interact with a data conversion program or device to exchange the data. The data interface may also allow disparate devices to communicate through a Public Switched Telephone Network (PSTN), the Internet, and private or semi-private networks.

Figure 3:
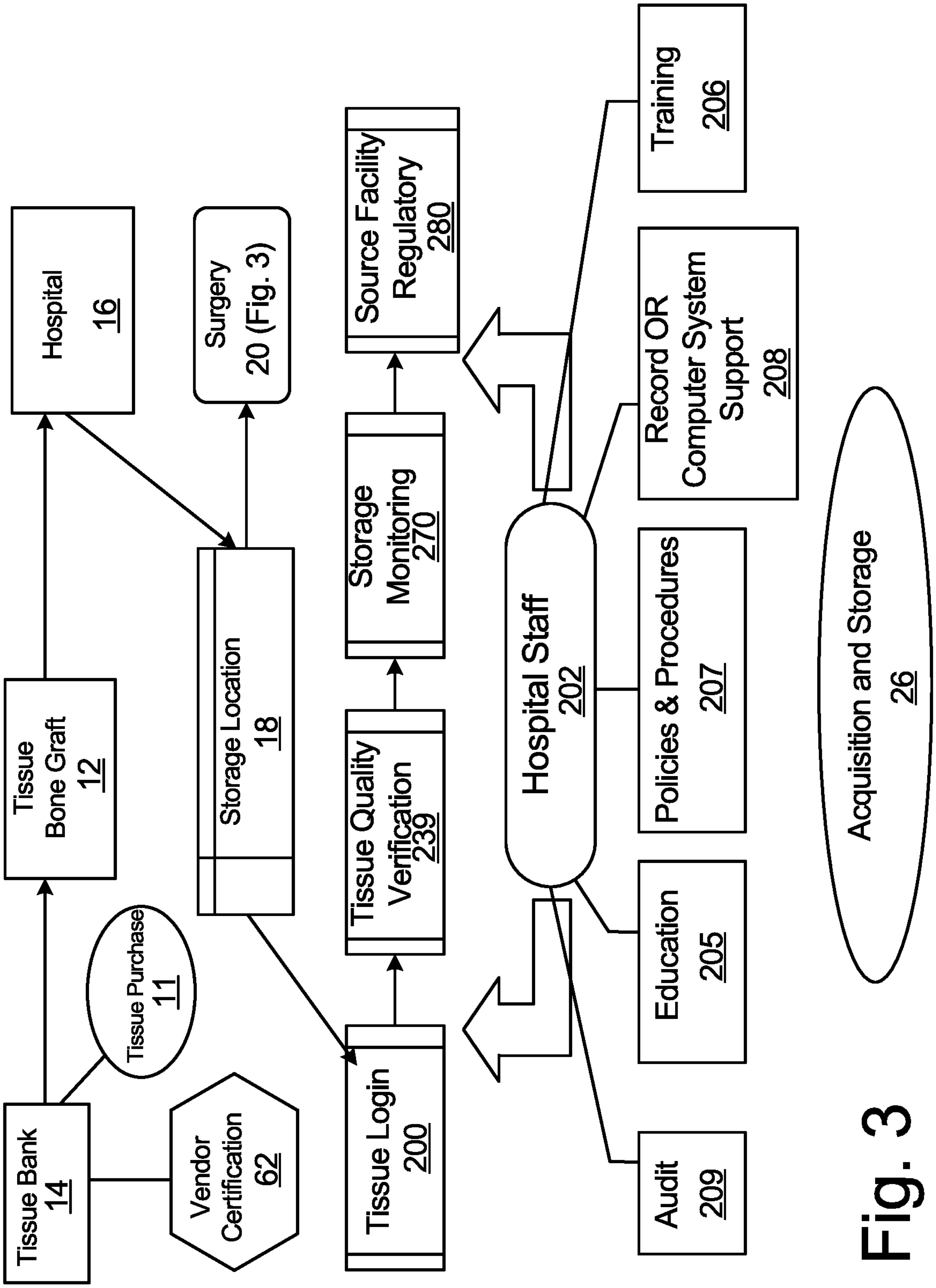
FIG. 3 is a schematic diagram showing the storage and acquisition portion of a comprehensive tissue management system.

The acquisition and storage portion 26 of the comprehensive tissue management system 10 is shown in detail in FIG. 3. The first aspect of the system is supplier certification 62 of the tissue bank 14. The present invention prompts the medical establishment to create criteria to determine the guidelines for selecting a supplier.

Rather than merely rely upon the name and reputation for quality and safety of the supplier as many hospitals do, this process step of the system requires affirmative verification that the tissue bank complies with all of the regulatory requirements and industry standards applicable to the sourcing, storage, and handling of transplant materials. At the most basic level, this can consist of documenting that the tissue bank 14 is currently registered with the FDA to supply that kind of tissue—in this case bone graft 12. Such FDA registration documentation may be obtained directly from the tissue bank 14, or from the FDA, including the FDA's Website: https://www.accessdata.fda.gov/scripts/cber/CFAppsPub/tiss/index.cfm.

Some states like New York, California, Georgia, Maryland, and Florida require that tissue source facilities (processors, tissue banks, and distributors) be specially licensed for this purpose. Again, documentation of this state license may be obtained directly from tissue bank 14, or else from the applicable state licensing agency. One must ensure that the FDA registration and applicable state licensure pertain to each type of transplant material to be sourced from tissue bank 14. Supplier certification step 62 more preferably may include directly auditing the tissue bank concerning their policies and procedures for sourcing, storing, handling, and transporting the transplantable materials, and personally inspecting their facilities. Much relevant information can be obtained from such direct efforts to certify the performance of the tissue bank 14.

This supplier certification step 62 can also preferably be supported by the hospital 16 entering into a memorandum of understanding or other contract with the tissue bank to comply with all regulatory requirements and industry standards for safely sourcing, storing, handling and transporting the transplantable materials. The tissue bank may take its responsibilities more seriously if it risks contractual breach and damages in addition to potential loss of its FDA registration and state license.

Figure 4:
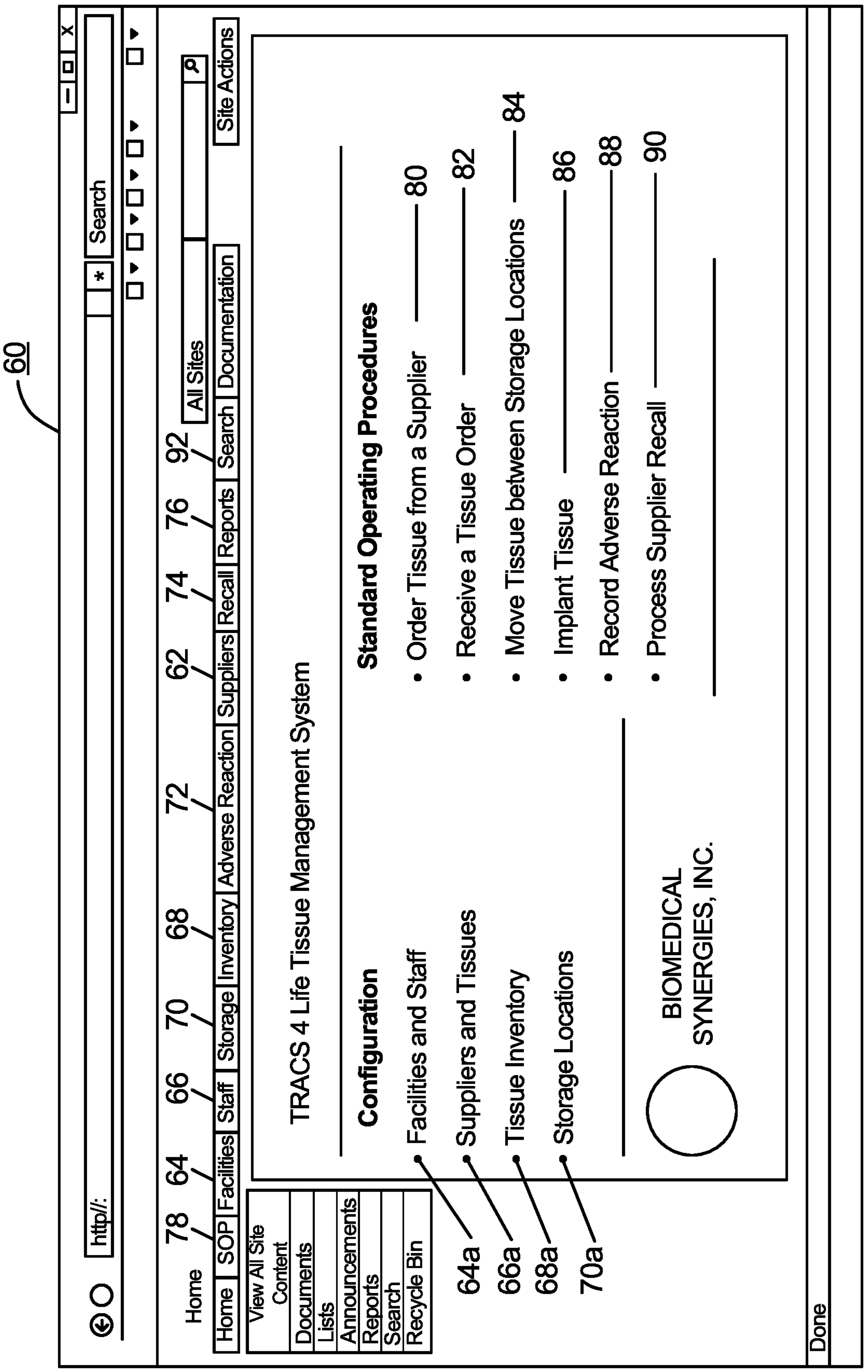
FIG. 4 is an interactive graphic user interface illustrating a main (home) menu of functions for the comprehensive tissue management system.

The home screen 60 of the software program 54 is shown in FIG. 4. By marking or clicking a button or similar marking indicator, a user can activate myriad functionalities of the software program, such as entering certification information for suppliers 62, calling up a list of facilities 64 in the medical establishment, obtaining a list of staff members 66 of the medical establishment, securing an inventory listing of transplantable materials located within the facility or medical establishment 68, obtaining a listing of available storage locations 70 for transplantable materials at the facility or medical establishment, creating documentary records pertaining to adverse reactions 72 for transplantable materials implanted into a patient, conducting or facilitating a recall 74 of transplantable material, and generating a variety of reports 76 related to such activities. Hyperlinks 64*a*, 66*a*, 68*a*, and 70*a* provide another convenient means for selecting these functionalities related to facilities and staff, suppliers of transplantable materials, existing inventories of transplantable materials, and storage locations for such transplantable materials.

Icon 78 on the home GUI screen 60 also enables the user to access and record data pertaining to a number of standard operating procedures conducted by the medical establishment. These standard operating procedures can include ordering transplantable materials 80 like tissue bone graft 12 from a supplier such as tissue bank 14, receiving ordered transplantable materials 82, moving transplantable materials between storage locations 84 at the medical establishment, implanting one or more transplantable materials in a patient 86, recording adverse reactions by such patient to the transplantable materials 88 (72), and processing supplier recalls of transplantable materials 90 (74). Icon 92 enables a search to be performed upon any of this data.

By clicking on icon 62 of the home screen GUI 60, the user calls up the certified suppliers GUI 92 shown in FIG. 5. This list contains all of the certified tissue suppliers 94 that have been entered into the software program. By clicking on a radio button 96 for one of the supplier entries 94, or double clicking a name, the supplier information GUI 98 for a specific supplier is called up, as shown in FIG. 6. This is the principal GUI screen contained within the comprehensive tissue management system 10 for providing background information concerning the supplier.

As shown in FIG. 6, field 100 permits the name of the supplier, such as Allosource ("tissue source") to be recorded. A specific address, contact name, phone number, and fax number for the supplier may also be entered. The field 102 contains identifying types of the supplier, such as "tissue bank" or "distributor." The tissue classification 104 (e.g., autologous) and tissue type 106 (e.g., other autologous tissues) may be conveniently selected from drop down boxes provided within the GUI.

The user is then prompted via "add tissue" button 108 to create entries 110 for each transplantable material type that the supplier supplies. This information includes the class 112 and tissue type 114, as well as whether the supplier is specifically approved by the medical establishment or regulatory authorities as a supplier of that tissue type. Very importantly for purposes of the comprehensive tissue management system 10 of the present invention, the user is prompted and required to enter within field 118 the FDA Registration Number for the supplier, as well as the expiration date 120 for that FDA registration. This information represents proof that the specific supplier is in good standing by the FDA to supply transplantable materials. More preferably, the comprehensive tissue management system 10 could require this FDA registration information to be entered and confirmed for a particular type of transplantable material, since a supplier will usually not be certified by the FDA to supply all types of transplantable materials.

The Supplier Information GUI 98 shown in FIG. 6 can also prompt the user to select the appropriate "yes/no" choices for AATB accreditation, EBAA accreditation, state licensure, and other accreditation as required by the hospital 16 for the supplier. In the case of a "yes" answer, the specific number is entered for the AATB accreditation, EBAA accreditation, state license, or accreditation.

For purposes of quality control, the supplier information GUI 98 shown in FIG. 6 can also prompt the user to identify the frequency with which the registration and accreditation credentials of the supplier should be reconfirmed, as well as the type of documentation that should be checked. This information is important, since a supplier may lose its FDA registration or state license status to supply a type of transplantable material, and the medical establishment will want to know this fact before it orders transplantable materials of that type from that supplier. The frequency of this registration or accreditation reconfirmation will be a time period that corresponds to the risk profile that is acceptable to the medical establishment, such as six months, one year, or two years. The supplier information GUI 98 can also prompt the user to confirm whether or not documentation used to reconfirm the registration/accreditation credentials for the supplier have been received and reviewed.

Finally, a medical establishment may choose to audit the supplier on a periodic basis in order to provide additional information for confirming that the supplier is a safe source for providing transplantable materials of a particular type. The medical establishment's internal requirement that the supplier facility be audited should be noted. Once an audit is actually performed upon the supplier facility, the performance date, individual performing the audit, and pending documents should be recorded. The existence of any conformance issues resulting from the audit is noted, and further defined within an information box. The individual who performed the review of the audit documentation and defined the conformance issues should be entered, along with the review date. Once all of this information is entered into GUI 98, a "submit" button should be selected in order to enable the comprehensive tissue management system 10 to process the information and populate screens within other associated GUI's of the system.

Icon 122 allows the user to delete a particular tissue entry for the supplier. Icon 124 enables the user to edit the particular line entry for the specific supplier.

Transplantable materials like the tissue bone graft 12 may be ordered in step 11 of the acquisition and storage portion 26 shown in FIG. 3 of the comprehensive tissue management system 10 of the present invention. By clicking on the "order tissue from a supplier" icon 80 of the home GUI 60 depicted in FIG. 4, tissue order GUI 130 shown in FIG. 7 will be called up to enable placement of a purchase order with a supplier for the bone graft.

Figure 8:
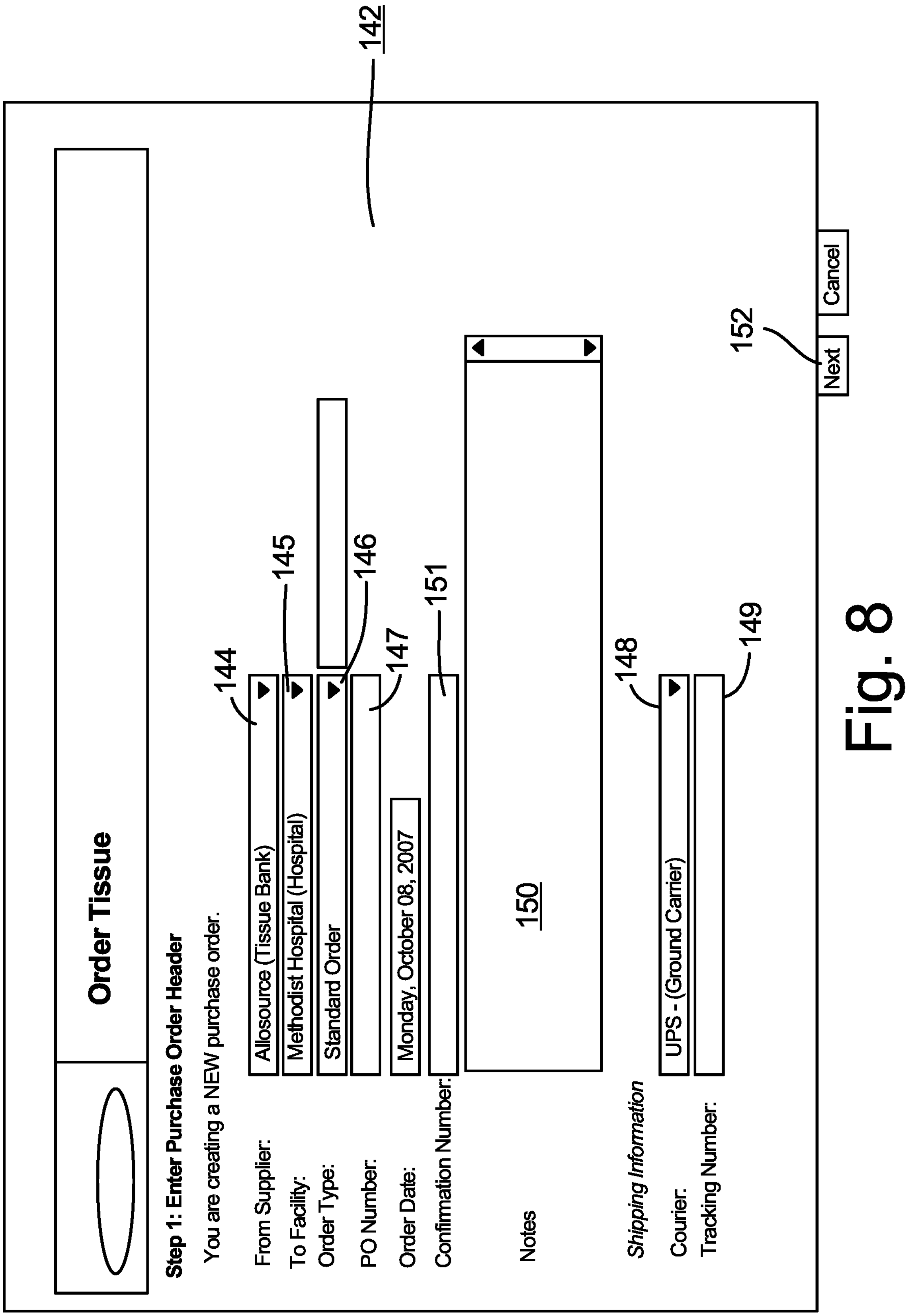

As further depicted in FIG. 7 for tissue order GUI 130, a listing of open purchase orders 132 placed by the medical establishment or individual facility is provided. This data includes the title 134, status 135, number of items 136, order type 137, order date 138, and total fee 139 for each purchase order. Hyperlink 140 allows the user to create a new purchase order for transplantable material, calling up GUI 142 shown in FIG. 8.

GUI 142 initiates the process for placing a purchase order. Drop down box 144 provides the user a convenient list of supplier suppliers authorized by the medical establishment from which to choose. Field 145 lists the facility of the medical establishment, and may include a drop down box if the medical establishment contains multiple facilities. The order type is identified in field 146, which may include, e.g., standard orders or open purchase orders. The purchase order number will typically be assigned by the medical establishment, and should be entered in field 147. Identification of a courier for shipment of the ordered transplantable material should be entered into field 148, which may also include a tracking number 149 assigned by the delivery courier service. Special notes pertaining to the order may be recorded in field 150. Finally, a confirmation number assigned by the supplier should be inserted into field 151. Clicking on "next" icon 152 calls forth GUI 154 shown in FIG. 9.

GUI 154 continues the purchase order process, enabling specific identifying information for the order to be entered. Field 156 allows a product catalog for a particular supplier to be selected. This preloaded catalog is shown more fully in GUI 158 of FIG. 10, and identifies all of the transplantable material products available from that supplier. Selection of a particular type of transplantable material (e.g., cortical strut) 160 shows in the lower portion of the GUI a series of different sizes of the product (frozen vs. non-frozen) 161 with corresponding prices 162. Also of great importance, a product code 163 for that specific product is included. Clicking on this product code 163 automatically populates field 164 of GUI 154 shown in FIG. 9. Clicking on "look up" icon 165 prompts the software system 54 to verify this product number for accuracy. Alternatively, "select" radio button 166 may be chosen, which will provide a drop down box for purposes of choosing the transplantable material product for the purchase order from the pre-loaded supplier catalog.

The size of the product may be inserted into field 168, or this information may be automatically provided by selection of the entry 161 in GUI 158. The desired quantity of the product should be entered into field 169, along with the price for each unit 170. Finally, the type of inventory (e.g., stock, special order for a particular patient, consignment by the supplier, or a facility transfer) may be entered into field 171. Clicking on "add tissue" button 172 allows additional transplantable material products to be added to the purchase order.

Figure 11:
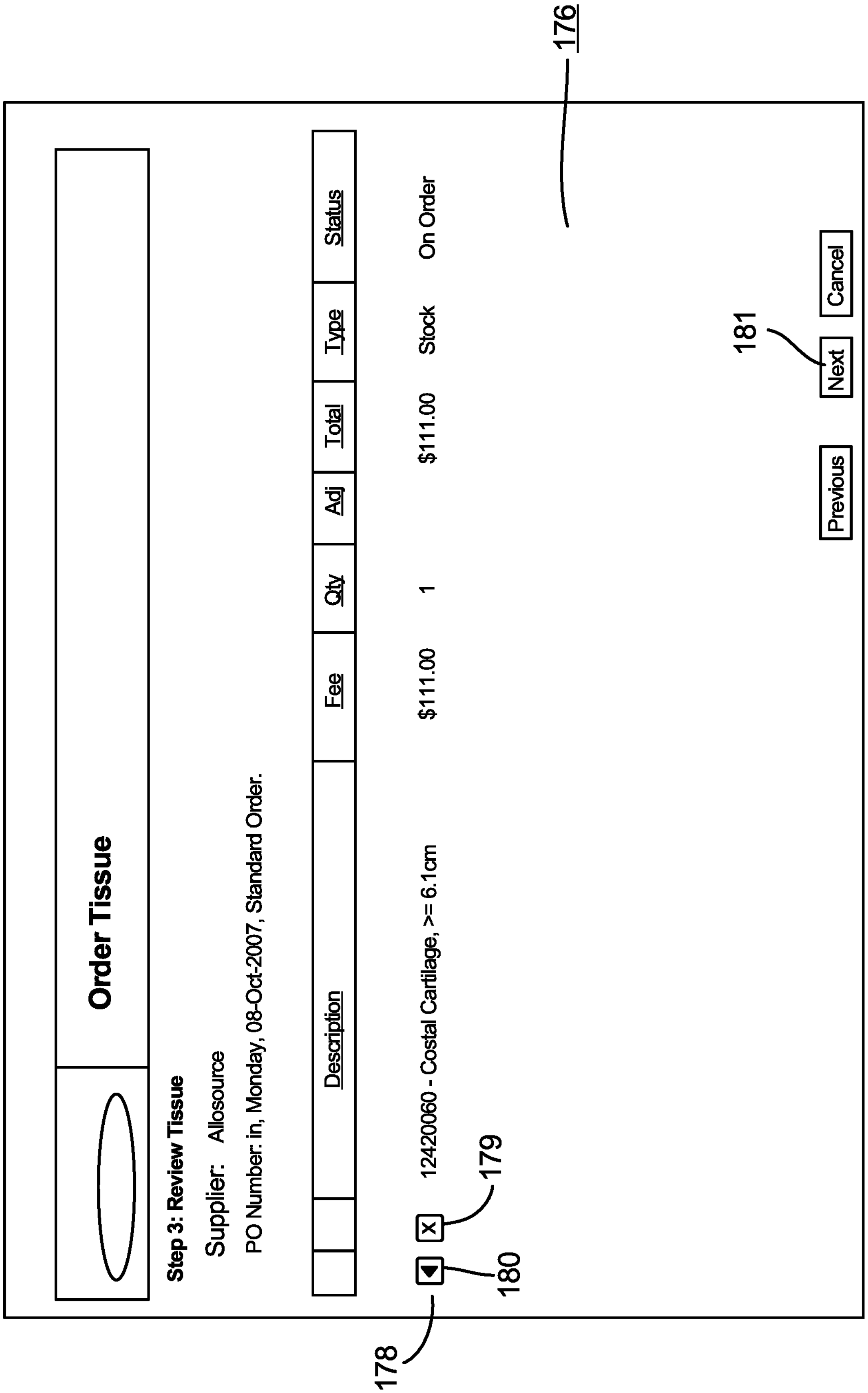
FIGS. 11-12 are interactive graphic user interfaces illustrating additional tissue order screens.

Clicking the "next" icon 174 calls forth GUI 176 of FIG. 11. This GUI enables the user to review a summary of the items 178 in the purchase order. Icon 179 allows a particular entry to be deleted from the purchase order. Icon 180 takes the user back to the order GUI 154 of FIG. 9.

Figure 12:
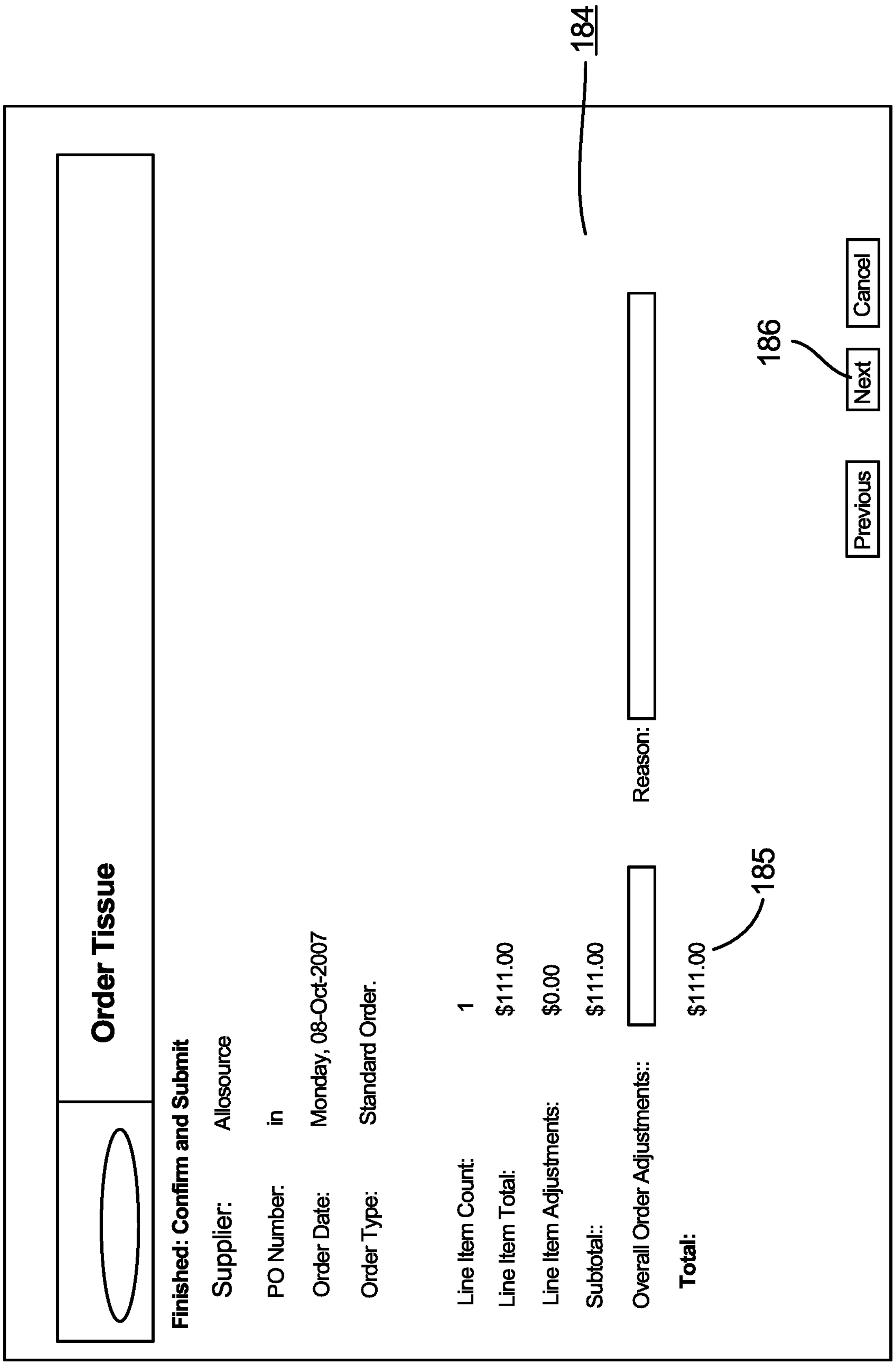

Clicking the "next" icon 181 of GUI 176 will provide a purchase order confirmation GUI 184 shown in FIG. 12. This GUI supplies a total purchase price 185 for the total items ordered. Selection of the "submit" icon 186 completes the purchase order process for the transplantable materials.

If the tissue product is being ordered for a particular patient at the hospital, as opposed to generally restocking the hospital's inventory for such tissue product, then this fact must be recorded so that when the tissue product is received by the hospital it is reserved for that patient. This important identifying information will include the patient's name, date of birth, gender, and ID/Medical Record Number ("MRN"), as well as the scheduled date for the patient's surgery.

The order status will be noted in field 135 of GUI 130 shown in FIG. 7. This system will also automatically check the supplier information supplied under GUI 84 to make sure that that supplier possesses the necessary current FDA registration, state license, and other accreditation credentials to supply the tissue product. If the supplier for the tissue purchase order does not possess these necessary credentials, or this information has not been entered into the system, then the user will be notified. A message will be sent by the comprehensive tissue management system to a predetermined official within the hospital who must authorize the purchase of the tissue product from the unapproved supplier before the purchase transaction can be placed. Such special authorization might be justified in case of an emergency where a surgical patient is in the operating room waiting for the tissue product. Such a purchase from an unauthorized supplier should be abnormal. In this manner, the system helps to ensure as a general matter that the hospital purchases transplantable materials only from properly credentialed supplier institutions.

Next, all bone grafts 12 supplied by tissue bank 14 to hospital 16 in accordance with FIG. 3 should be logged in accordance with step 200. Part of this invention's system is to help the hospital determine where this should be done—i.e., the blood bank, central supply, or surgical department. This is determined by the skill of the staff 202, the availability of staff 24 hours a day, and the ability to monitor and maintain storage equipment and alarms. The invention promotes the development of a specific policy and procedure regarding how the tissue pieces will be accepted from tissue bank 14, and which specific staff 202 will be responsible for logging in the tissue. The logging process includes a unique identification number for each piece of tissue (specially assigned where necessary), coupled with the expiration date and acceptable temperature range for each tissue product.

The tissue login procedure 200 conducted by the hospital staff 202 is assisted by the tissue receipt GUI 300 shown in FIG. 13. This screen of the software program 54 is accessed by means of clicking on the "receive a tissue order" icon 82 of the home page GUI 60 shown in FIG. 4. The selection of this icon 82 will cause the software program to retrieve the tissue receive GUI 300 shown in FIG. 13, which lists a number of open purchase orders 302 of transplantable materials.

Figure 14:
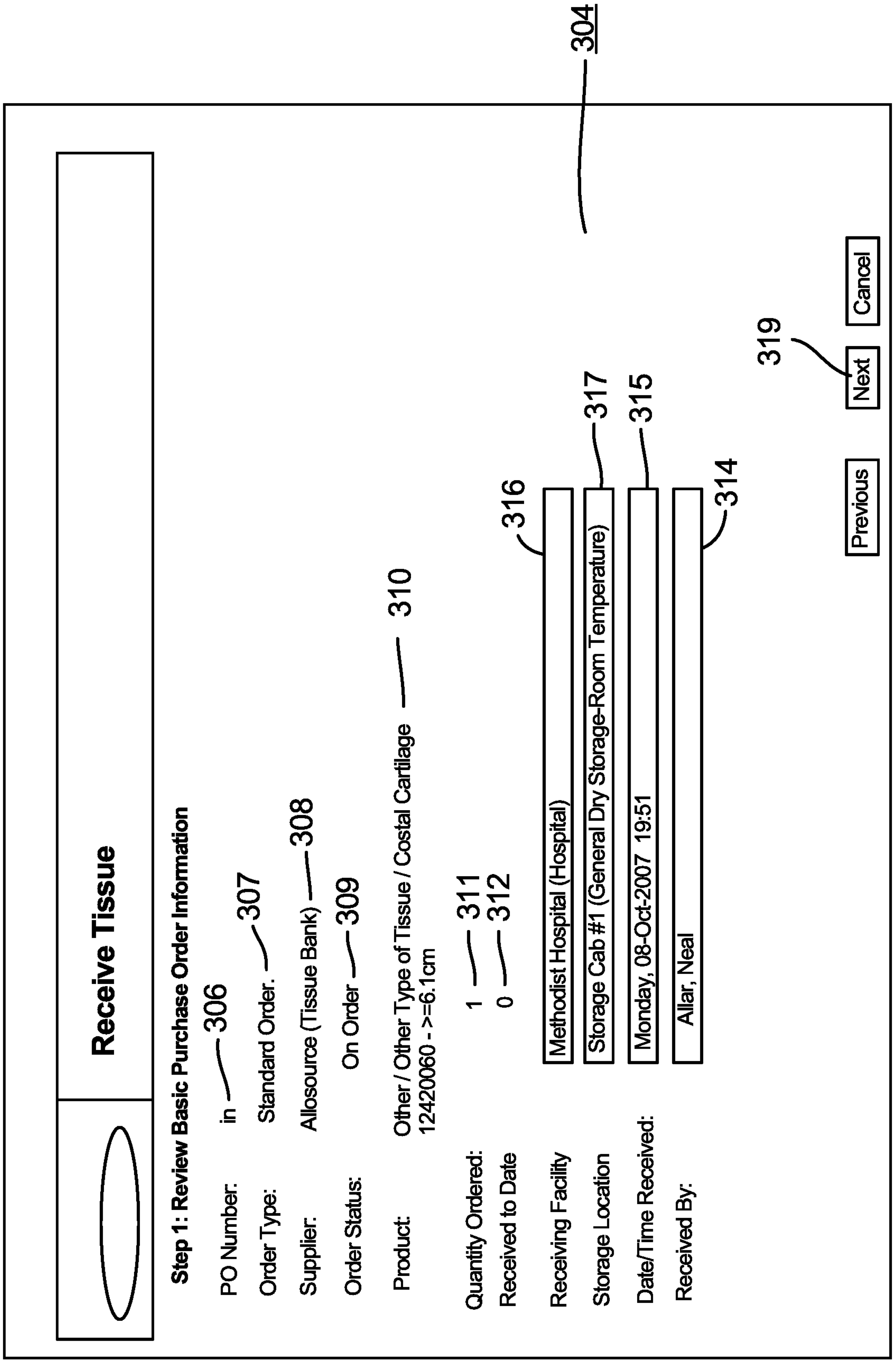

By selecting the particular purchase order 302 on GUI 300 to match the delivered transplantable material, GUI 304 shown in FIG. 14 appears within the software program 54. The purchase order number 306, order type 307, supplier 308, order status 309, product description 310, and ordered quantity 311 will automatically be populated by the system, using data inputted into tissue order GUIs 142 and 154 shown in FIGS. 8-9.

The hospital staff member who received delivery of the transplantable material product should input his or her name into field 314, along with the date and time 315. This information may be provided by means of a drop down box or other graphical input means. The medical establishment facility receiving the transplantable material should be entered into a field 316, and a specific storage location 317 assigned, including by means of drop down boxes.

Figure 15:
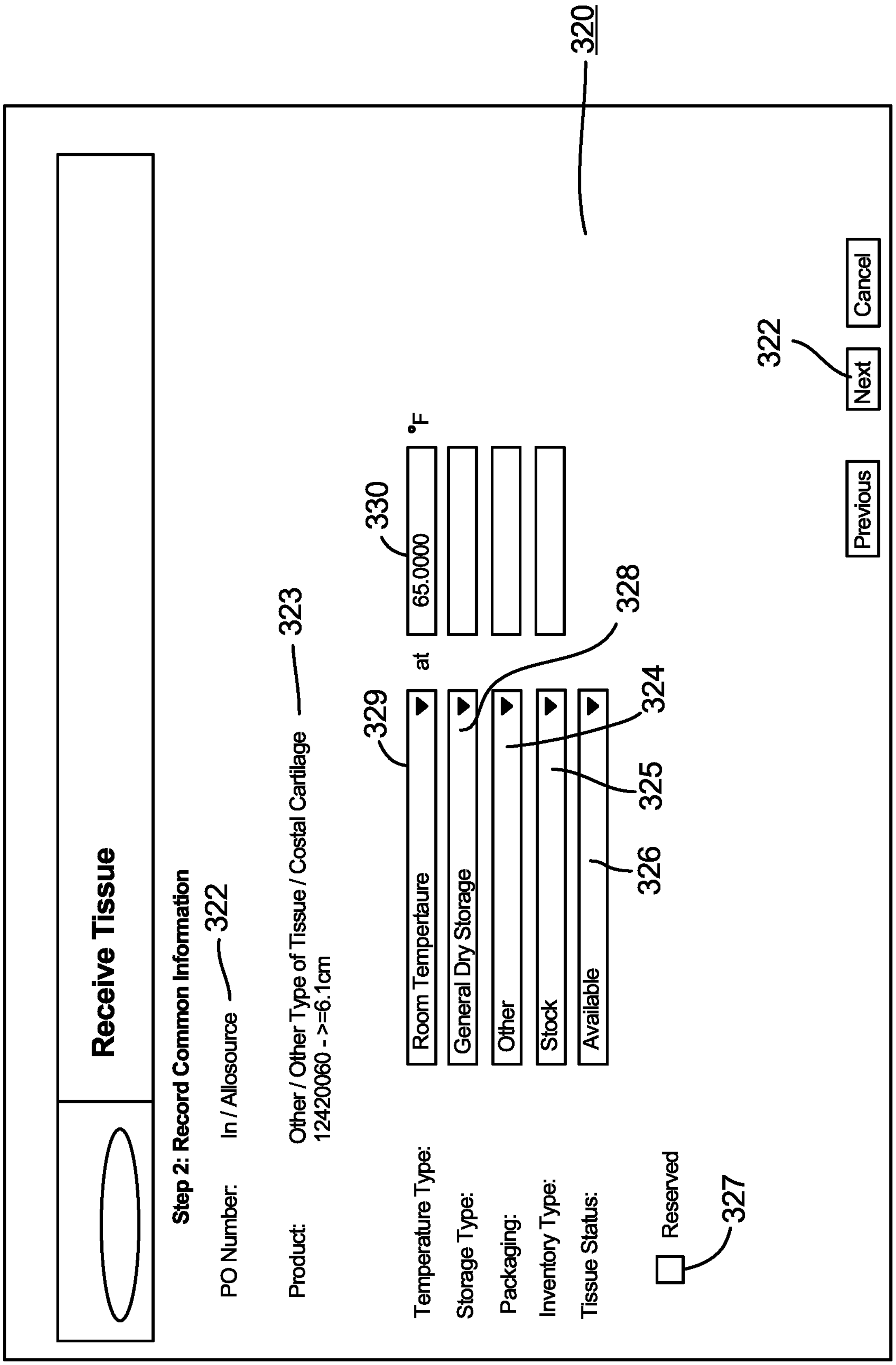

After clicking onto the "next" icon 319, GUI 320 shown in FIG. 15 will appear. Again, the purchase order number source 322 and product description 323 data for the piece of transplantable materials will be automatically populated. The user should enter information for the packaging type 324 and inventory type 325 for the transplantable material. This includes whether the material is immediately available for use in a surgical procedure 326. If the transplantable material is reserved for a particular patient or surgery, radio button 327 should be checked. Finally, the user should designate the specific type of storage facility 328, temperature type (e.g., room temperature, refrigerator, freezer) 329, and temperature 330 under which the transplantable material should be stored.

Clicking the "next" button 332 calls forth GUI 338 shown in FIG. 16. This GUI prompts the user to record information unique to the particular piece or pieces of transplantable material that have been received. Again, the purchase order (source, quantity ordered, quantity received, and product description fields 340, 341, 342, and 343, will be automatically populated to confirm that the transplantable material was received 220. The bar code assigned by the supplier on the packaging for the transplantable material will be scanned by the user to conveniently and accurately enter this information into field 344 and saved 345. In addition, the user must manually enter the information in field 346 for the expiration date for the transplantable material, product lot number 347, and field 348 for supplier-assigned unique identification numbers.

For products not assigned a unique identification number by the supplier, the software program will also assign a unique tracking number for the transplantable material product so that it can be identified throughout its custody by the hospital and ultimate implantation in a patient. A donor number 350 identifies the specific donor of the specific piece of transplantable material.

Other important information pertaining to the piece of transplantable material that should be entered into the tissue receipt GUI 338 is quality control information. Check boxes 352, 353, 354, and 355 must be marked by the user in order to prompt him to check whether the temperature was adequately maintained for the transplantable material during shipment, whether the entire product label is legible, whether the packaging for the transplantable material is intact, and whether other required quality checks for the product are satisfied. If the user does not check these boxes, the software does not allow him to proceed. In a preferred embodiment, failure to check a particular box may produce a warning message with an opportunity for an authorized supervisor to override it if the problem (e.g., an illegible product label for known product) is deemed to be acceptable. If, on the other hand, the product should be rejected and returned to the supplier, then a check box 356 is marked. If desired, a verifier can be used to double check this information with the verifier identified in a field. Additional written comments regarding the inspection results can be entered.

The invention encourages the hospital to establish inspection criteria 239 (FIG. 3) for the incoming transplantable material. This process step includes verification upon receipt of the transplantable material product from the tissue bank 14 that package integrity of the tissue is satisfied to avoid infection or spoilage of the tissue. The staff member 202 should also verify that the temperature range for the piece of transplantable material during transport from tissue bank 14 was controlled and acceptable in accordance with FDA regulatory standards or the manufacture's recommendations.

The invention also encourages the medical establishment to create specific policies and procedures regarding how it should handle, store, and transplant the transplantable material 12. This determination 270 (FIG. 3) begins with careful review and maintenance on file of the package inserts for each type of transplantable material used by the establishment. Each supplier of tissue has created different instructions for how their products should be transported, handled, stored reconstituted, and used. These instructions are approved by the FDA. Great care should be taken to ensure that the package integrity is maintained for the products during transportation and handling in order to avoid introduction of contaminants into the product.

Clicking "submit" button 358 enables the received transplantable material product and its identifying data to be saved. A summarizing data entry 360 appears in GUI 338. Field 362 allows the next transplantable material product to be received 220.

The transplantable materials must also be maintained at their proper temperatures during their storage at ambient temperature or in refrigerators and freezers at the hospital. The FDA-approved package insert for each type of tissue product will specify the appropriate temperature or temperature range. The hospital must determine what types of refrigerator or freezer units it will use, along with the associated monitoring and alarm equipment. Appropriate policies and procedures 64 (FIG. 3) need to be established to ensure continuous monitoring of the temperature conditions in the refrigerator and freezer units with a central alarm system or chart recorder. A number of transplantable material products that are stored at ambient temperature do not specify the temperature range that needs to be maintained. The invention encourages that the hospital create an appropriate temperature range. If not specified, the invention suggests careful review of the package inserts for the ambient temperature products used by the hospital. The range is then created by taking the highest low temperature identified in the package inserts and the lowest high temperature designated in these inserts.

Alarms for each storage unit should be set so that the alarm sounds before the temperature within the unit exceeds the predetermined temperature range. In this manner, the ambient storage area, refrigerator or freezer units will maintain a temperature condition that accommodates the transplantable materials stored within.

Schedules for the periodic inspection and maintenance of the refrigerator and freezer storage units must be created. Periodic testing of the alarm systems operatively connected to the storage units and the emergency power source should also be scheduled. It is also important to maintain daily records of the actual storage unit temperature conditions to prove that the transplantable materials, in fact, were stored at their required conditions. Each piece of transplantable material should be identified within the log record by its unique identifier number, date, time and storage or handling location to document its exact condition until final disposition, transplant or discard.

If the surgery unit 20 maintains its own storage units for transplantable materials, then it must establish similar policies and procedures for monitoring the temperature conditions therein, inspecting the valid operating conditions thereof, and documenting the actual temperature conditions of the refrigerator and freezer units. The surgical unit 20, however, must also maintain precise records for each and every piece of transplantable material that it handles and uses in surgical procedures. Such records should identify the specific piece of transplantable material, its condition and all reagents or other supplies introduced to it prior to its transplantation or implantation into the patient.

Figure 16A:
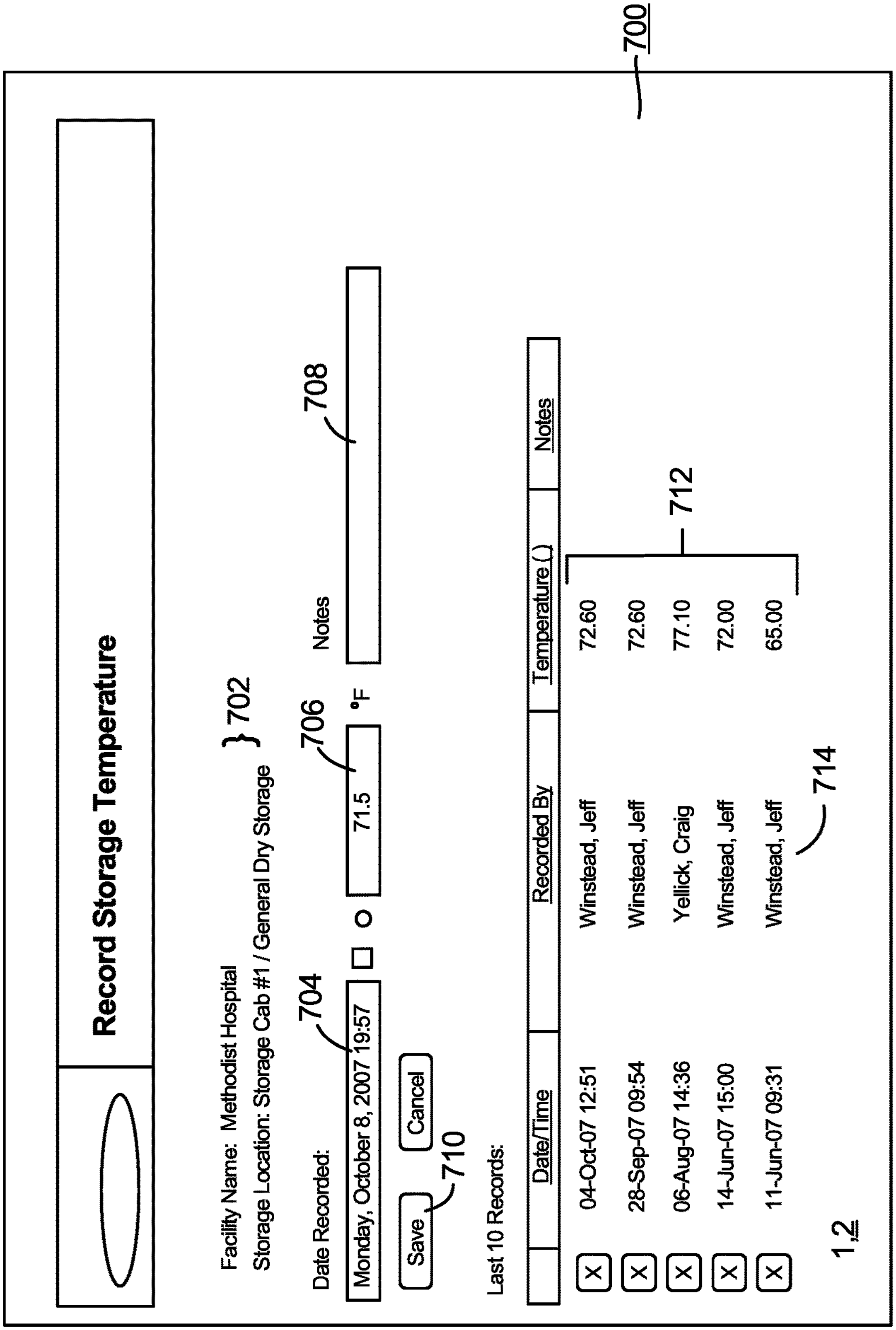
FIG. 16a is an interactive graphic user interface illustrating a record storage temperature screen.

GUI 700 shown in FIG. 16*a* enables the user to record periodic inspections of the temperature of a storage unit identified in field 702. The inspection date and time 704, temperature 706, and any notes 708 are entered into their respective fields. Clicking on "Save" button 710 adds the new data entry to the last-ten record entries summarized in field 712. The staff member who measured the temperature of the storage unit is also identified in field 714.

Another important step carried out by staff within the surgical unit 20 will be the reconstitution of the transplantable material from its storage condition to a condition necessary for its use in surgery. This is determined by the package insert and current good medical practice. This will typically include the immersion of the tissues, like bone, into a sterile saline bath with or without antibiotics. Other human cells, tissues, NBI, and organs are reconstituted with appropriate reagents. The nurse or other qualified/trained staff member designated to conduct such reconstitution step must carefully read and adhere to the specific instructions printed in the package insert for the transplantable material product and make the implanting surgeon aware that they are deviating from the FDA-approved package insert. The surgeon decides based on his medical judgment whether the change from the package insert is merited. At the end of the surgical procedure, the tissue usage identification cards ("TUIC") must be completed for the product implanted into the patient and promptly returned to tissue bank 14.

In some cases, a hospital 16 may actually serve as a supplier of transplantable materials to other medical establishments. This often is the case for "sister" hospitals or large hospitals that internally source transplantable materials and use them in their other surgical procedures. The comprehensive tissue management system 10 requires the hospital 16 to periodically ask itself these questions:

- Does it produce human cells, tissue and cellular and tissue-based products ("HCT/Ps"), including stem cells, reproductive cells, tissue or surgical bone?
- Does it store purchased tissue and ship it to another institution that is not part of its organization? For example, does it supply a VA Medical Center or other hospital within the community?
- Does it store tissue from one patient case on the chance that the surgeon needs it for another patient with the exception of vessels used in organ transplant?
- Does it perform additional processing on incoming tissue? For example, gas sterilization of bone for further use.
- Does its testing lab perform tissue donor testing for communicable diseases?
- Does its lab test specimens for organ donors, and are such results used to determine eligibility for tissue donors?

If the answer to any of these questions during this source facility regulatory compliance step 280 depicted in FIG. 3 is "yes," then the hospital 16 must register itself with the FDA much like a tissue bank 14 does.

A critical component for the comprehensive tissue management method 26 of the present invention is the hospital staff 202. As shown in FIG. 3, a trained staff member must be designated with responsibility for each of the process steps described above. Every effort must be made to ensure that the responsible staff member has the required educational background 205 (FIG. 3) for conducting the process step. Also important is ensuring that such staff members will actually be available at the relevant time to carry out the activity step. For example, if transplantable material is maintained in a surgical unit and the responsible person is unavailable to respond to an alarm sounding on a refrigerator unit, this undermines proper operation of the comprehensive tissue management system 26. All designated staff members should be provided the necessary training 206 to discharge their responsibilities. They should also be provided the necessary policies and procedures 207 by hospital management that allows them to perform their duties without risk to themselves or the patient.

In order to ensure that the above-described process steps are carried out, the comprehensive tissue management system 10 should be embodied with a record-keeping system that requires the completion of individual records 208 attesting to the completion of the individual process steps. The comprehensive tissue management system 10 is preferably embodied within a computer tissue tracking and tracing software system. Individual screen shots for a process step could require completion of the necessary data entry before the computer can progress to the next screen shot.

Finally, a periodic internal audit 209 must be conducted by the hospital 16 for all of the process steps that form the acquisition and storage components 26 of the comprehensive tissue management system 10. Only in this manner can the hospital management be assured that their staff is complying with the necessary policies and procedures, and take corrective action where necessary.

Figure 17:
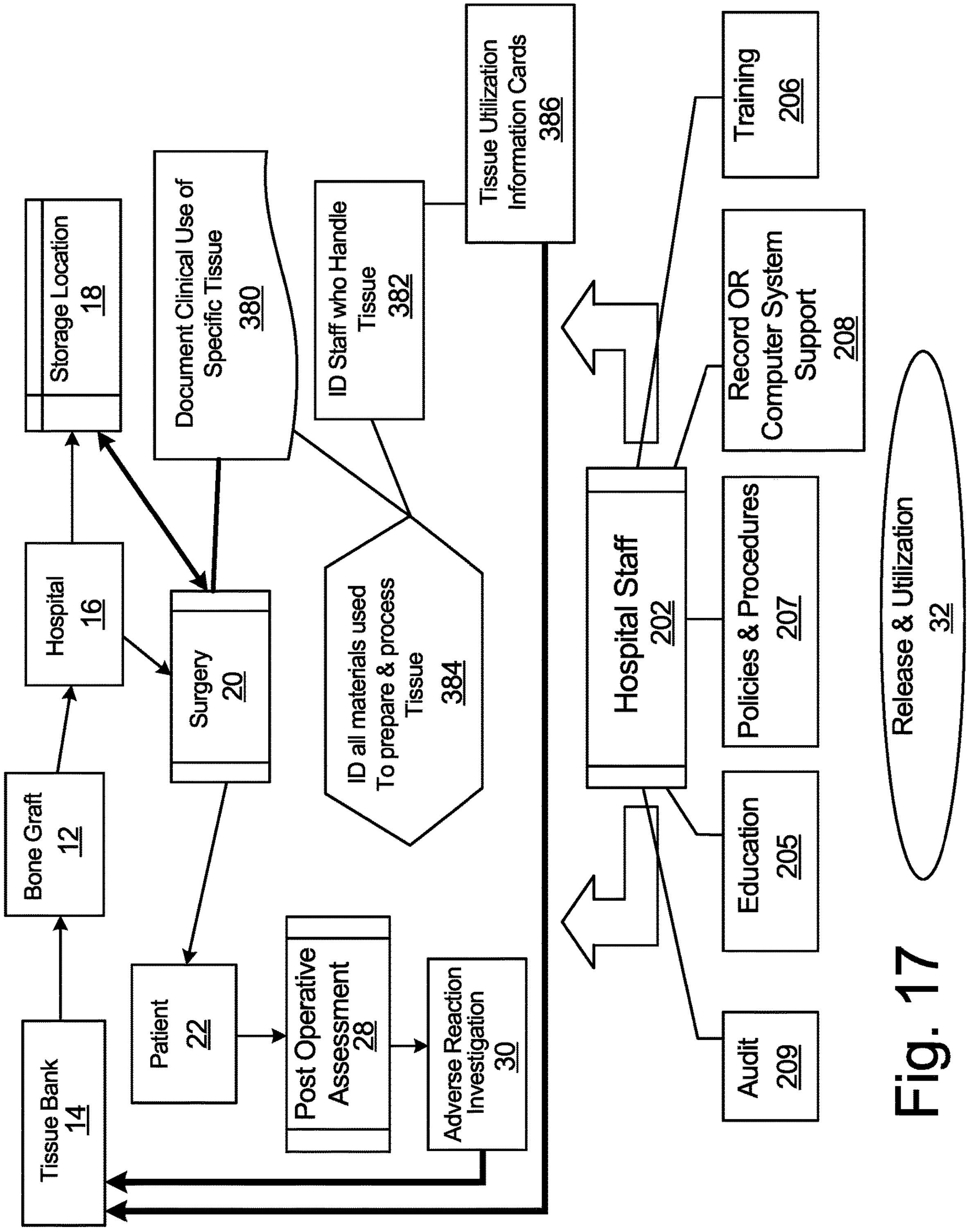
FIG. 17 is a schematic diagram showing the release and utilization portion of a comprehensive tissue management system.

FIG. 17 illustrates the tissue tracing portion 32 of the comprehensive tissue management system 10 in greater detail. The objective of this system is to provide an adequate record of the transplantable material's history in case of an adverse reaction 30 in patient 22 after surgery or, if the tissue bank issues a recall and the patient who receives the transplantable material needs to be identified. For example, if the adverse reaction is an infection and is due to the operative contamination or the management of the bone graft in the hospital, then the problem is localized to the hospital and can be addressed by improving the hospital's practices. If, on the other hand, the infection is determined by investigation 30 to have been caused by the tissue graft, then the tissue needs to be traced back to tissue bank 14, so the supplier can be warned. A recall of similar transplantable material supplied by tissue bank 14 to the hospital 16 and other medical establishments may be necessary. Furthermore, there have been instances in which the FDA has issued recalls of transplantable material as a result of their investigations into poor practices of tissue banks, both accredited and non-accredited by the American Association of Tissue Banks ("AATB"). In some cases, follow-up diagnostic and medical treatment of other patients who were implant recipients of the similar transplantable material may be warranted as well.

To monitor the history of the tissue during its life in the hospital requires documentation of multiple steps starting with its entrance in the hospital and its maintenance in the storage locality 18 (FIG. 3). This will include assigning a unique identification code to the bone graft products, confirming the package integrity and safe condition of the bone graft upon receipt from the tissue bank 14, recording the actual temperature conditions, and identifying all staff members who handle the bone graft and the date and time of any such possession or handling activities from the time of initial login until the bone graft is transported to the surgical unit 20 for use in a surgery. Many of the process steps described above for the acquisition and storage tracking portion 26 of the comprehensive tissue management system can be employed to support the documentation steps.

Figure 17A:
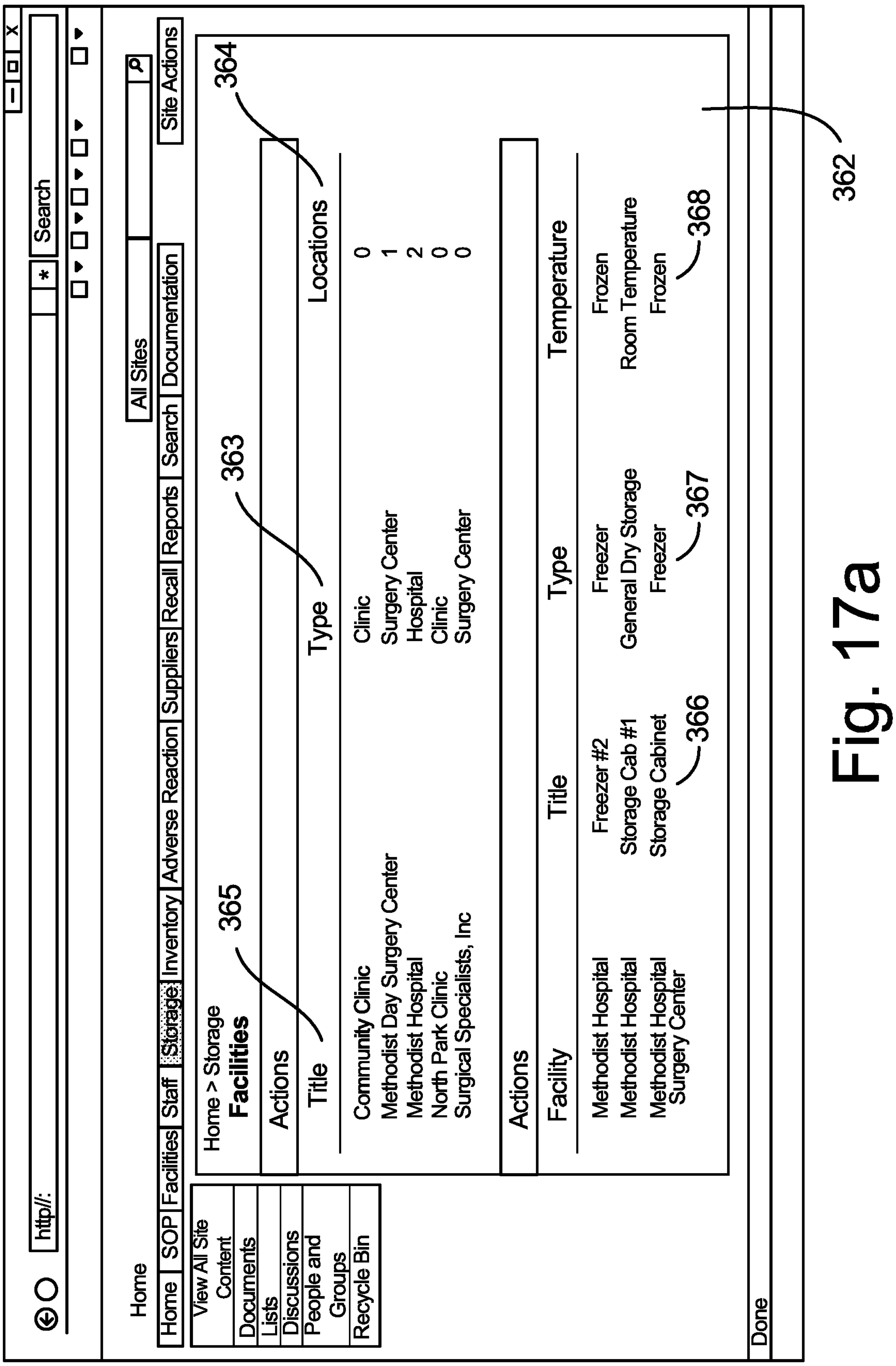
FIG. 17a is an interactive graphic user interface illustrating a tissue storage unit screen.

Once the transplantable material 12 reaches the hospital 16 and is logged in, it will be maintained in any of a number of possible storage locations 18 in the hospital before it is transported to the surgical unit 20 for clinical use in a patient 22. Possible storage locations at the hospital include the blood bank, central storage department and the surgical unit. Clicking tab 70 of the home GUI 60 of FIG. 4 causes the software program to produce GUI 362 shown in FIG. 17*a*. This GUI screen itemizes the type of facility 363 and number 364 of storage unit locations for each facility 365 of the medical establishment. It also defines the title 366, type 367, and proper temperature condition 368 for each such storage unit.

Figure 18:
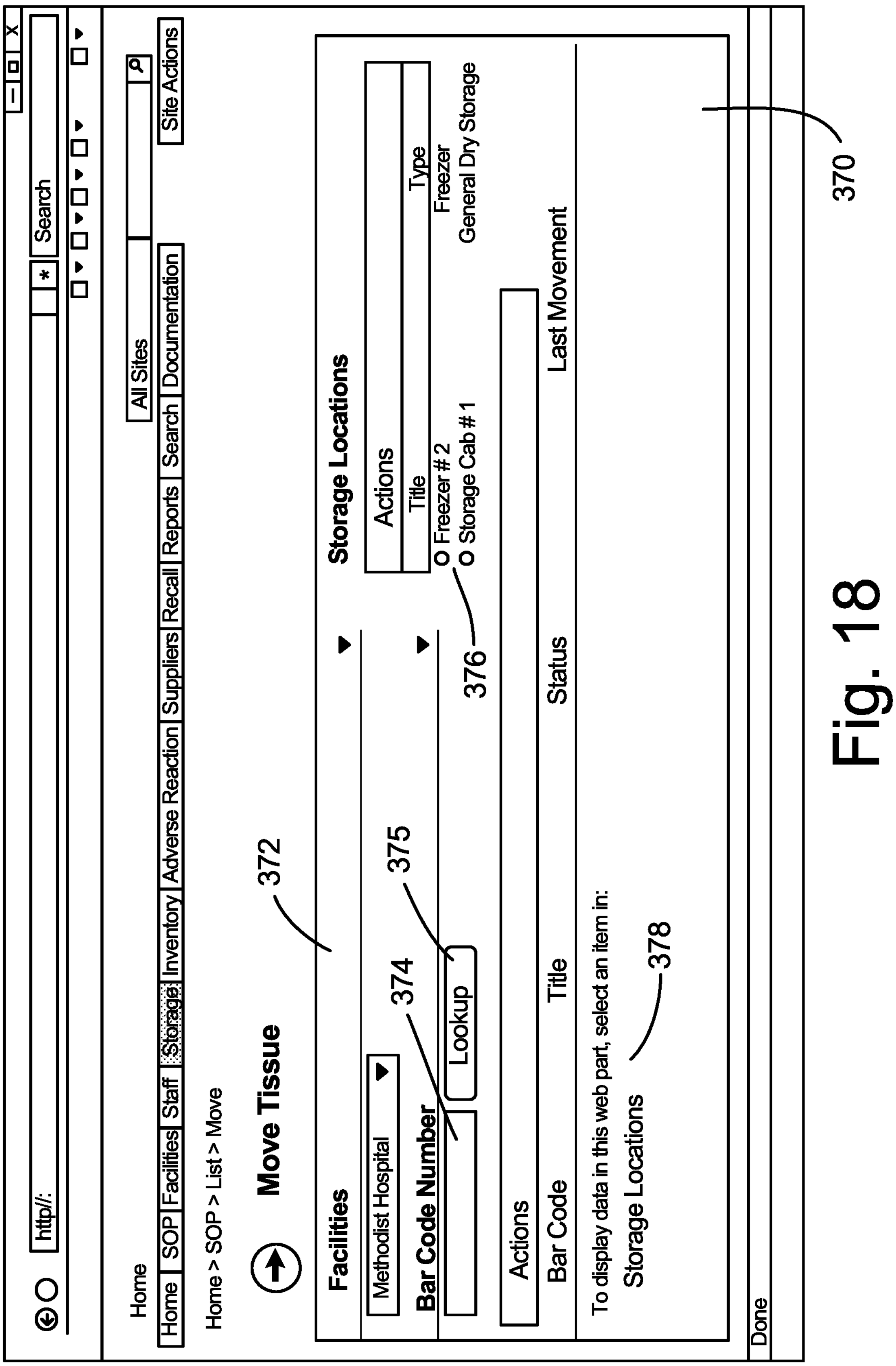
Figure 19:
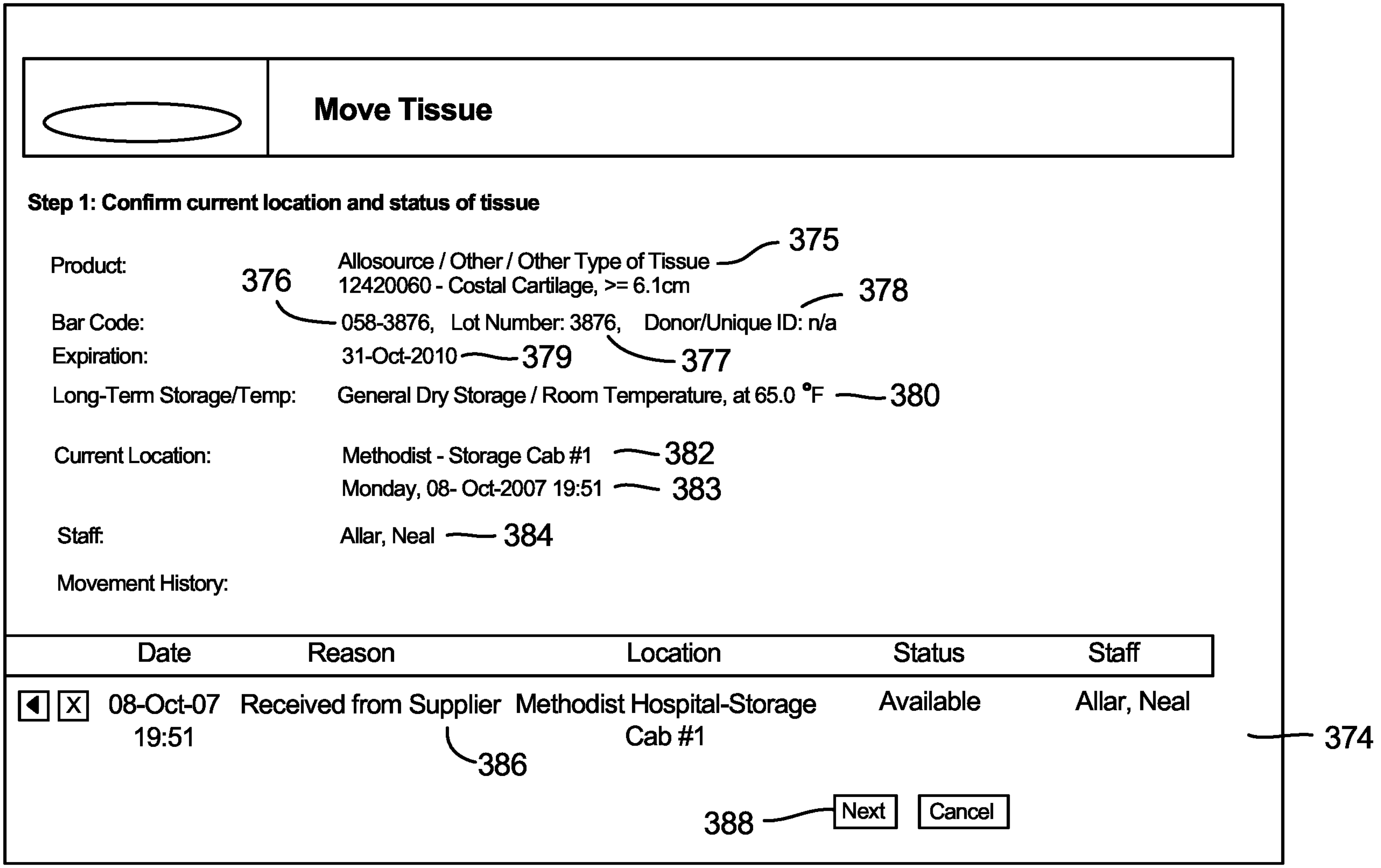

By selecting "Move Tissue" hyperlink 84 in the home GUI 60 of FIG. 4, the move tissue GUI 370 shown in FIG. 18 is called up by the software program. This GUI enables the user to choose a particular medical establishment facility 372, along with a specific piece of transplantable material stored there. This transplantable material may be identified by its bar code number 374 or unique ID number, assisted by selection of a look-up table 375. Alternatively, the user may select the radio button 376 for any of the storage locations within the medical establishment facility to produce an itemized list 378 of all of the recorded transplanted materials stored therein. Selection of a particular transplantable material item will cause the software program 54 to call up GUI 374 shown in FIG. 19.

The data fields for the product 375, bar code number 376, lot number 377, donor/unique ID number 378, expiration date 379, and long-term storage condition and temperature 380 will be automatically populated within their respective fields in GUI 374. Also automatically populated within GUI 374 will be the current storage location 382, date of last movement 383, and staff member responsible for the previous data entry for the piece of transplantable material. An entry 386 summarizing the historical storage data for this transplantable material is also provided.

By clicking "next" button 388, the software program produces GUI 390 shown in FIG. 20 for purposes of documenting the transfer of an item of transplantable material within a medical establishment. The product and its bar code and expiration date will be automatically described within fields 392, 393, and 394, respectively, using data previously entered into prior GUI's. The date and time of the transfer of the transplantable material must be recorded in field 395, along with the identities of the staff member releasing the transplantable material from the present storage location 396, and receiving it at the new location 397; A reason for the transfer should be entered into field 398, which could include its use in a surgical procedure.

The new storage location should be recorded in field 400, along with the necessary type of storage temperature (e.g., room temperature) 402 and actual storage temperature conditions 403. If the transplantable material is being transferred to a different facility, then this fact should be recorded in field 404. Moreover, if the item of transplantable material has been reserved for a particular surgery, then check box 406 should be checked, and the surgery date, patient identification number, physician order number, and doctor recorded in fields 407, 408, 409, and 410, respectively.

Finally, the system requires the user to inspect the transplantable material item once again, guided by the check boxes 412, 413, 414, and 415 for adequate temperature maintenance during storage, product label legibility, intact product packaging, and other required quality checks criteria. Failure to make these inspections and check the corresponding boxes will prevent the user from exiting this GUI screen 390 after clicking the submit button 417.

In this manner, an item of transplantable material will receive separate entries within tissue movement GUIs 374 and 390 for each time that it is transported to a new storage location. This could include return of the tissue item to the supplier in the event, e.g., that the tissue is no longer needed, there is a recall by the supplier, or if the tissue was determined by the hospital's quality control inspection to be defective.

In the vent of a supplier-generated recall, several steps must be taken to insure that the tissue is removed from the hospital or surgical facility inventory and storage and prevent future use. Once the recall notice is received by the hospital from the FDA and/or the manufacturer, the staff charged with processing the recall must enter the identifying information (e.g., unique ID, serial number, lot number) from the transplantable material or NBI into the system.

Once the identifying information from all of the transplantable material or NBI included under the particular recall is entered into the system, the system requires the user to identify the specific type of transplantable material involved in the recall. This feature safeguards against duplicate identifying information from two distinct manufacturers being confused and erroneously included or excluded from the recall process.

At this point, the system pinpoints if the hospital has or has had any of the recalled product in its inventory. If so, the system identifies the product, so that a staff member may remove the product from inventory, using the "Move" standard operating procedure. Additionally, the "Recall" standard operating procedure isolates any recalled product that has been already implanted into a patient. If so, the system identifies the patients and has the capability of generating letters to be sent to the affected patients.

Finally, if the number of products being recalled by the manufacturer is large, the user can place a prospective hold on that manufacturer. By do so, when products from this supplier are being received into the inventory in the future, the system alerts the user, and requires a supervisor to override before the particular product(s) can be accepted into inventory. The goal of this feature is to prevent recalled product from entering the hospital's "clean" inventory.

Another instance of moving transplantable material within a medical establishment facility could include discarding of the tissue after, e.g., its expiration date has passed, or quarantining of the tissue inside the hospital in the event of an adverse reaction investigation where safety of a similar piece of tissue is under review. In this manner, the related tissue will not be used in a surgical procedure until it is cleared. When tissue is used by the hospital in a surgical procedure, this will be recorded in the "issued" field.

Thus, the historical record provided by the comprehensive tissue management system 10 of the present invention enables the hospital's handling of the tissue item to be traced in the event of an adverse reaction investigation or product recall. This is an important feature of the release and utilization portion 32 of the comprehensive tissue management system 10 of the present invention.

In the case of surgeries, an item of transplantable material needs to be selected. By clicking on the inventory tab 68 of the home GUI 60 of FIG. 4, an inventory listing of the transplantable material stored within the medical establishment is provided. An example of such a listing is shown in GUI 420 of FIG. 21. Filter 422 may be applied to select the transplantable material samples using different search criteria like supplier 424, classification 425, tissue type 426, inventory type 427, temperature 428, and surgery type 429. GUI 420 shows these transplantable materials sorted by supplier 424.

The major portion of GUI 420 contains a table exhibiting various characteristics for these transplantable materials. These characteristic data columns include supplier 426, product description 427, purchase order number 428, bar code identification number 429, product expiration date 430, inventory type 431, status 432, facility 433 where the product is stored, specific storage location 434, and temperature type 435. Note that the unique identification number for the product sample could be used instead of the bar code number 429. These data fields are automatically populated by data entered previously during the tissue receipt, moving, and storage functionalities. The inventory type entry 431 will indicate whether a specific transplantable material sample is a general stock item, or whether it is on consignment from the supplier, such as a tissue bank. Meanwhile, the status entry 432 indicates whether the product item is available for assignment to a surgery, or whether it has already been reserved for a patient in another surgery.

The inventory list of GUI 420 also features color-coded entries for particular transplantable material samples. For example, a red-highlighted entry might call attention to samples that are already expired. They need to be removed from inventory and discarded before they are accidentally implanted into a surgery patient. A yellow-highlighted entry, on the other hand, might flag product specimens that are still safe to use, but will expire soon. In this case, they should promptly be selected for a surgery, so that they will not be wasted after they expire.

Once the transplantable material 12 reaches the surgical unit 20, thorough records need to be created concerning the clinical use of this specific bone graft. This includes identification of the staff member who accepts the bone graft, identification of all surgical staff members involved in preparing the bone graft for its use in the surgical procedure, and recording the dates, times and personnel for all such activities.

Figure 22:
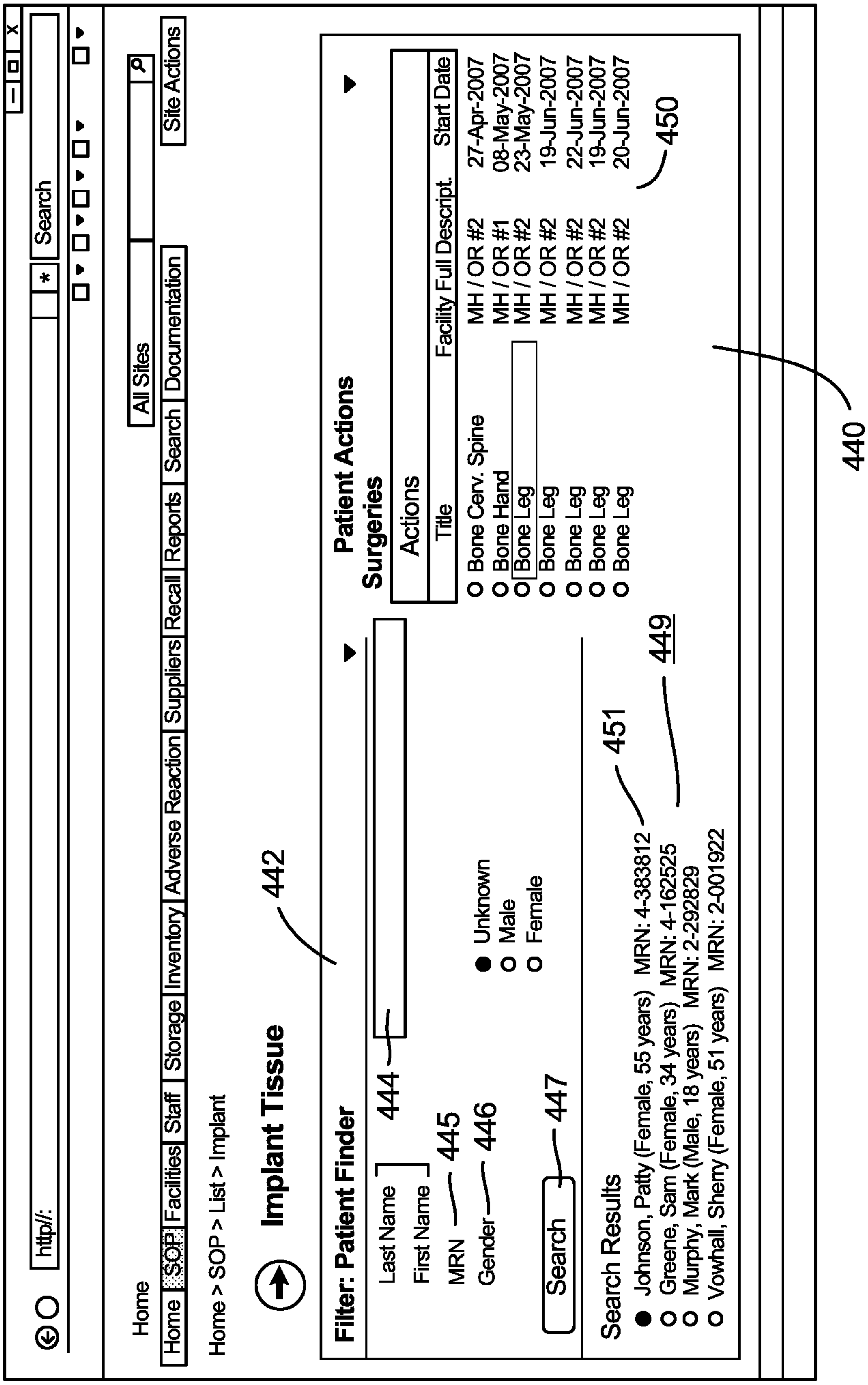

Accessed by means of implant tissue hyperlink 86 of home GUI 60 of FIG. 4, GUI 440 shown in FIG. 22 allows searches to be conducted for patients 22 or surgeries 20. Under patient finder filter 442, the name 444, MRN 445, and gender 446 of a specific patient may be entered, and the search button 447 clicked. A patient search results list 449 is produced thereby. A list of surgeries 450 conducted at the facility is also produced. These are surgeries that have already occurred.

As shown in GUI 454 illustrated in FIG. 23, selection of the Sherry Vowhall patient entry 452 produces a specific list 456 of surgeries performed on her at Methodist Hospital. A further list 458 of transplantable material products implanted in Ms. Vowhall during these surgeries also appears in GUI 454. Selecting radio buttons 457 enables the specific records for the surgeries to be viewed.

Figure 24:
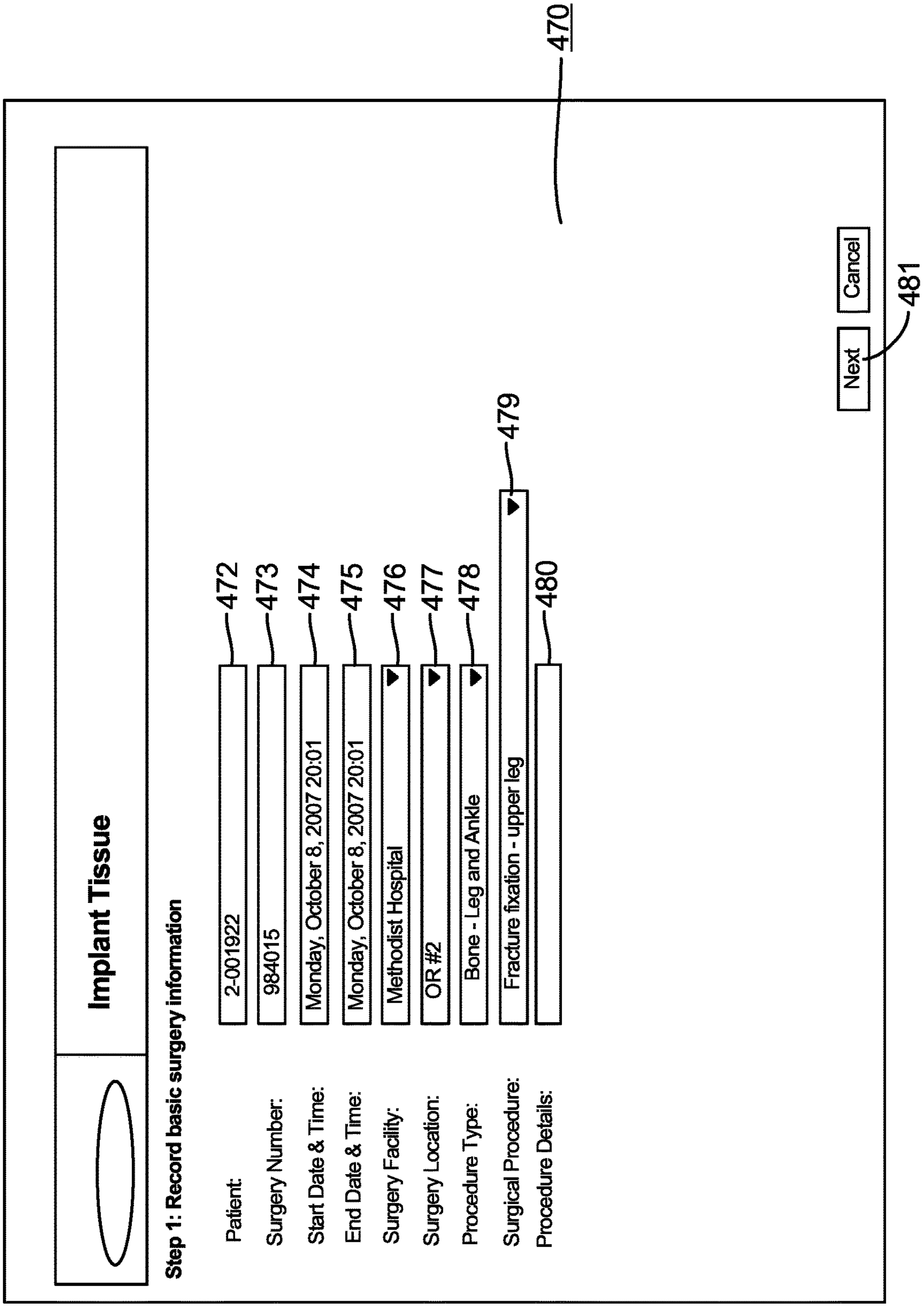

New patient entries may be created by selecting hyperlink 460. A new adverse reaction investigation may be entered into the system by clicking on hyperlink 462. Meanwhile, selection of hyperlink 464 enables the user to create a new surgery record, resulting in calling up GUI 470 shown in FIG. 24.

Figure 25:
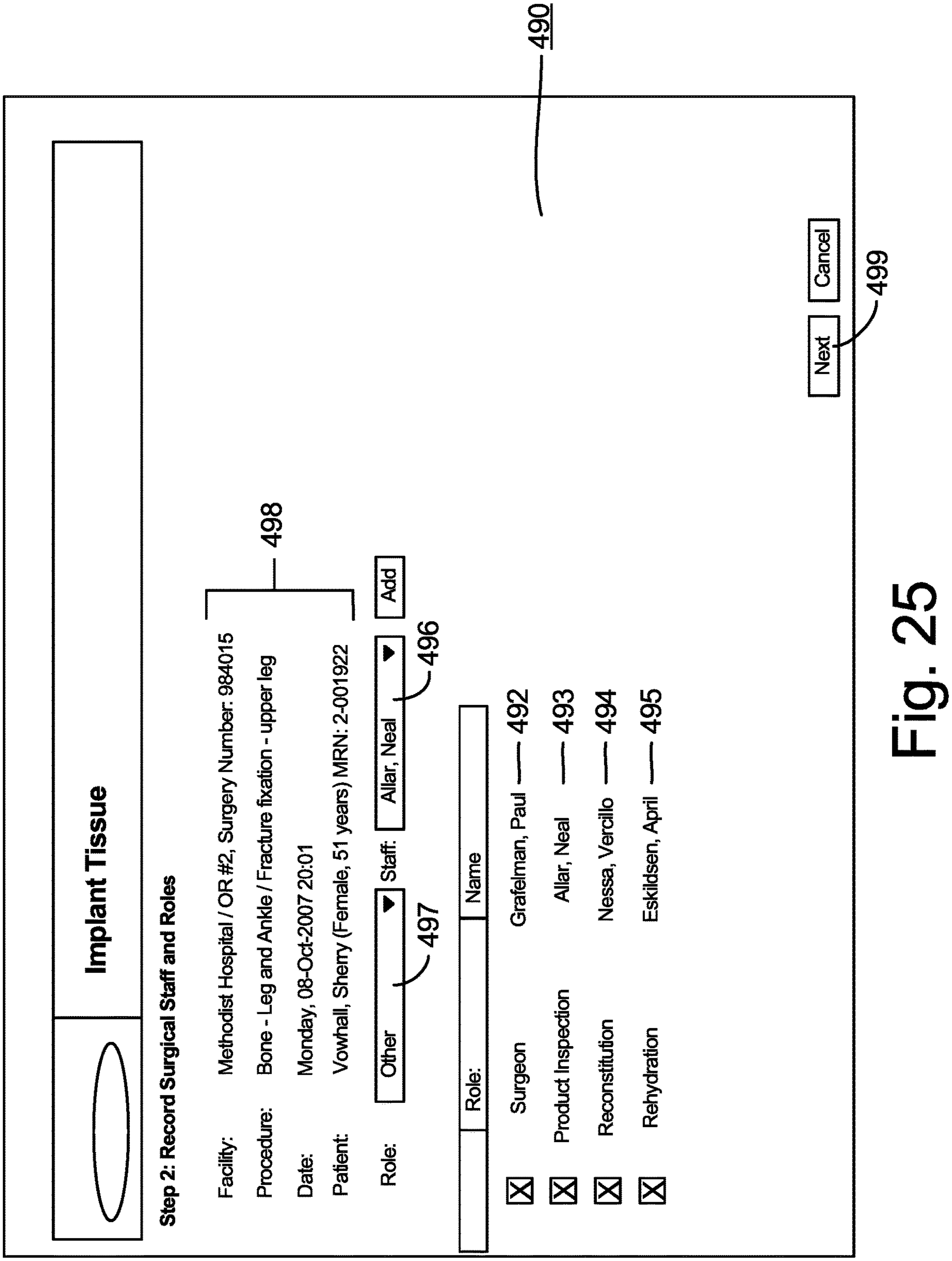

Within this GUI screen 470, basic information for the surgical procedure is entered. This includes the patient's identification number 472, an identification number 473 assigned by the hospital to the surgical procedure, the start and end dates and times 474 and 475 for the surgery, the surgical facility 476, the specific surgical location (e.g., a specific operating room within the medical establishment) 477, the procedure type 478, and surgical procedure 479. Drop down boxes with pre-entered hospital specific information can be provided to help the user with the entry of the data. Other procedural details can be recorded in field 480. Clicking on the "next" button 481 produces GUI 490 depicted in FIG. 25.

GUI 490 accommodates the recordation within the system of all staff members 202 of the medical establishment facility that handle, prepare, and implant the bone graft 12 into the patient. This includes the surgeon 492, internal product quality inspector 493, person who reconstitutes the bone graft 494, and person who rehydrates the product 495. Staff members and their role that they play with respect to the bone graft may conveniently be added via drop down boxes 496 and 497. The information fields regarding the surgical procedure 498 are automatically populated by data inserted elsewhere into the system.

Figure 26:
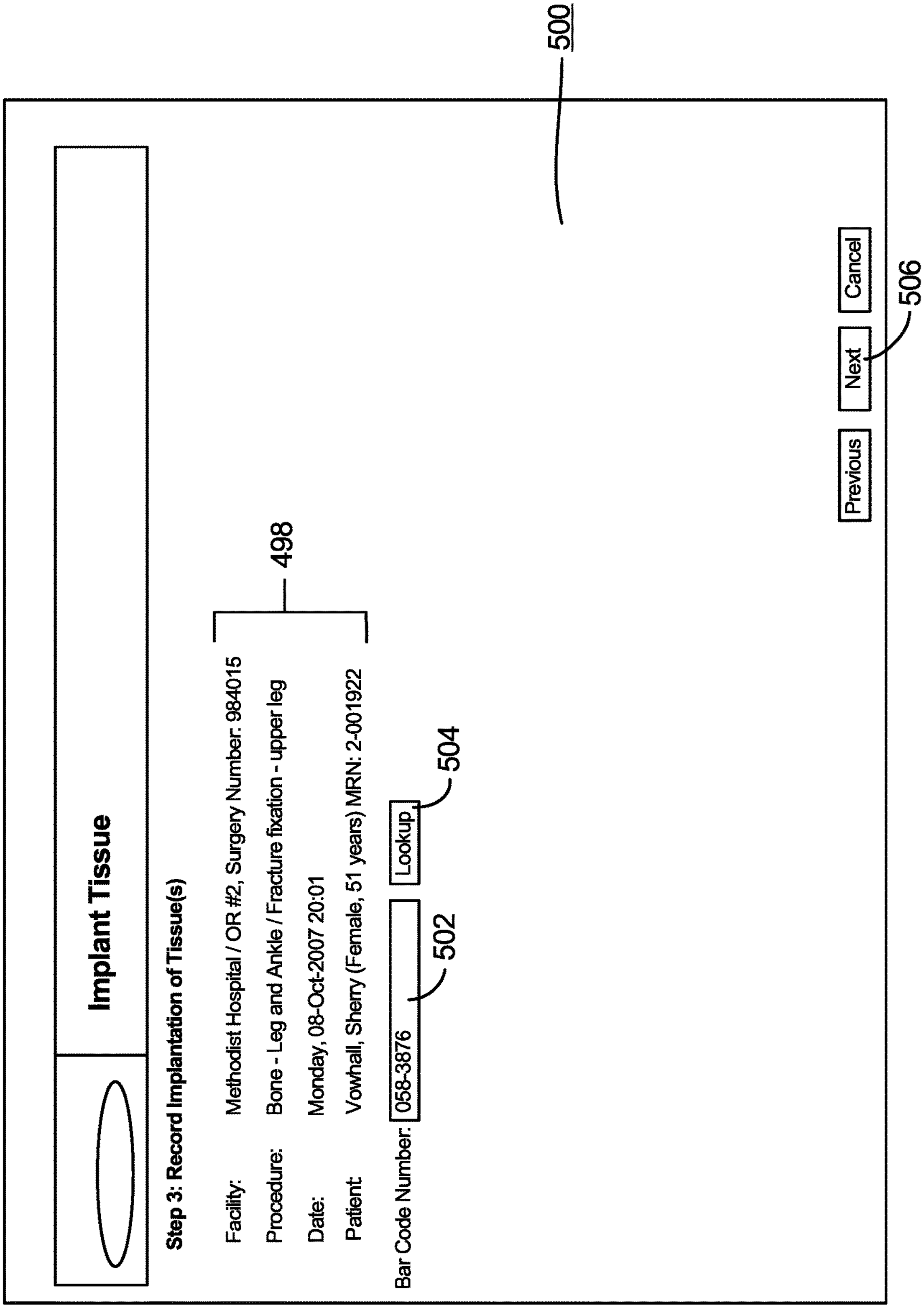

"Next" button 499 produces GUI 500 shown in FIG. 26. The bar code number 502 for the transplantable material is entered, and a lookup button 504 that accesses the facility's inventory is provided by the system to link the product's identifying information with the patient's MRN. Preferably, the bar code number is scanned into the system from the product package. The unique product identification number assigned by the medical establishment facility may be used as a substitute for the supplier's bar code number.

Clicking "next" button 506 transports the user to GUI 510 depicted in FIG. 27. In this GUI, specific information can be recorded regarding the specific use of the transplantable material. Descriptive fields 512 concerning the product and its supplier and expiration date are automatically populated by the system. The user should click the pertinent radio buttons 514 and boxes 516 to indicate whether the tissue product was implanted successfully within the patient, whether the product was used in its entirety or discarded, or whether the product was opened but not used within the surgery, or whether the tissue was explanted. Likewise, any comingling of the tissue with other tissue products should be recorded. The user must also confirm whether the tissue product was reconstituted strictly in accordance with the supplier's instructions 517, or whether any deviations from this procedure were made 518.

An important processing step by the surgical unit is the reconstitution of the bone graft product prior to its implantation in patient 22. As previously described, this should be done strictly in accordance with the instructions on the package insert. Documentation should be produced to indicate what supplies like syringes, heparin, saline or basins were actually used to reconstitute or prepare the bone graft, and confirm that all such supplies were used prior to their indicated expiration dates. The reconstitution products (e.g., saline solution) are recorded in field 520. Any modifications to the tissue should be noted in field 522, and surgical notes may be added in field 524.

At the end of the surgical procedure, the tissue usage information card should be completed and returned to tissue bank 14 to provide additional documentation of the clinical use and disposition of bone graft 12 in patient 22. The information contained within GUI 510 can be sent to the tissue bank to facilitate this reporting step. Specific policies and procedures need to be established to determine who will complete these cards according to the tissue bank requirement, since completion and return of such tissue usage information cards is frequently overlooked within the hospital industry.

Figure 28:
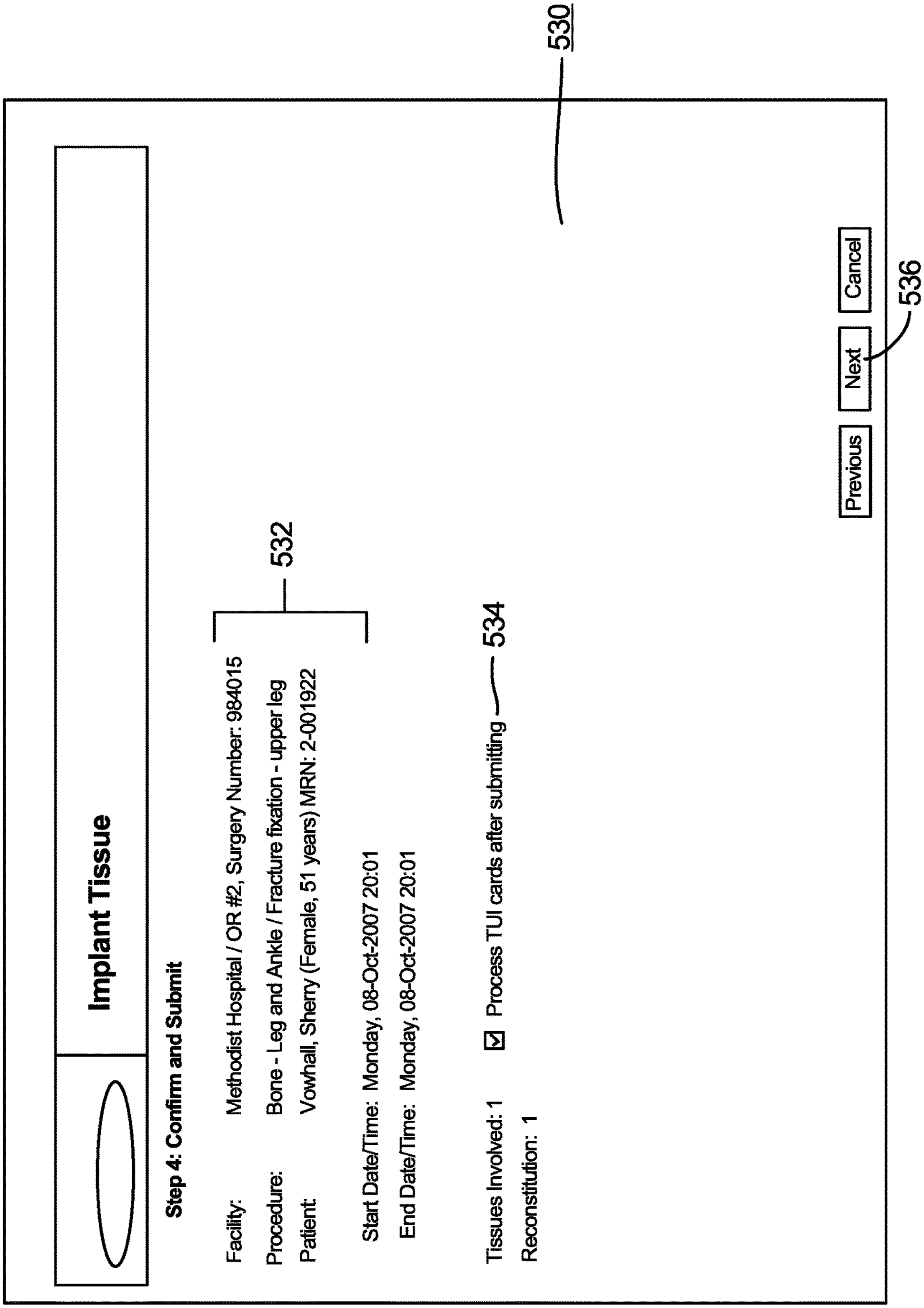

GUI 530 shown in FIG. 28 produces a confirmation summary of the surgical procedure information, and automatically processes the tissue usage information cards, using previously entered data regarding this transplantable material. Submitting the information via button 536 allows it to be printed in batch format on a periodic basis for the medical establishment facility management and/or transplantable material supplier.

The essential element of the release and utilization portion 32 of the comprehensive tissue management system 10 of the present invention is thorough and concurrent record keeping. Failure to document important steps in the acceptance, handling, storage, transportation, processing and clinical use of the tissue and associated reagents will greatly undermine the integrity of the system and put the patient at risk.

The hospital 16 should establish the time period for retention of each record within portion 32 of the comprehensive tissue management system 10. In the case of login sheets and recorded procedures for the transplantable material, such records should be maintained for at least 10 years. Any records related to the transplantable material like tissue usage information cards, preparation materials, central alarm/chart recorders must be kept 10 years after the date of distribution, transplant or expiration date of the material in question, whichever is latest.

A procedure for version control must also be established for all procedures that affect the transplantable material, including a unique name for each procedure, a version number and date when it became effective, and when the previous version no longer applies in order to keep the documentary records and procedure requirements clear.

As described previously for the portion 26 of the comprehensive tissue management system 10, designated hospital staff members 202 that are part of the release and utilization portion 32 of the system need to be assigned responsibility for keeping and maintaining all records and other documents associated with the comprehensive tissue management system. While a requisite degree of education 205 may be helpful, character traits of conscientiousness and thoroughness, as well as available time may be more helpful for any such staff member. All designated staff members should also be provided adequate training 206 in such tasks as how to read temperature charts, inspect refrigeration or freezer storage units, confirm the instructions on transplantable material product insert sheets, etc. These hospital staff members 202 should also be provided understandable policies and procedures 207 to help them do their part to support the integrity and accuracy of the comprehensive tissue management system 10. Periodic internal and external audits 209 should be scheduled by hospital management to confirm that all of the necessary steps pursuant to the comprehensive tissue management system are accomplished.

The comprehensive tissue management system 10 is predicated upon the proposition that hospital management and staff will actively investigate adverse reaction 30 and take corrective action in response to any adverse reaction in a patient 22. To accomplish thorough investigations of adverse reactions the invention has created the concept of "Medical Cladistics." Cladistics is the branch of biology that determines evolutionary and taxonomic relationships between organisms based on derived similarities. Similarly, medical cladistics looks for derived similarities in investigation of clinical problems such as adverse reactions so appropriate risk categories can be created. For example, if a patient develops an infection following surgery in which tissue has been used, and an investigation shows that other patients were operated on in the same operating room ("OR") suite developed similar infections, the "risk clade" is the OR suite, not the transplantable material, or the OR staff and the equipment sterilizer.

If a transplantable material product was associated with an infection, then the risk clade would have to be identified. Some transplantable material products can be more harshly treated than others. For example, tendons do not receive the same sterilizing treatments used by some tissue processors for bone. If an infection due to the transplantable material were bacterial and the transplantable material product implicated was a tendon, than the risk clade would be the other tendons from the same donor, not necessarily the bone products. If the infection were hepatitis, than all products from the donor may be the risk lade.

Investigation of the risk lade involves both the hospital where the transplantable material was transplanted and the transplantable material processor. Therefore, the transplantable material supplier must be notified immediately and a full investigation of the donor and processing quality control methods would be necessary to resolve the case.

The process of identifying a risk lade begins by defining an adverse reaction. This requires thorough evaluation of the actual orthopedic or other clinical and surgical practices employed by the hospital and its physicians. Factors that may influence adverse reactions include:

- Physician preference for certain proprietary transplant material products and supplies. Some products carry greater risks than others.
- How such products are normally prepared within the hospital.
- Pre and post-operative antibiotics that are commonly used by the surgical team.
- Are tissue products soaked in antibiotics prior to their implantation?
- Incidence of infections in the hospital comparing allograft versus metallic devices.
- Does the surgeon perform a gram stain or culture of the tissue product prior to its implantation?
- Determining whether adverse reaction in a patient is based upon cultures, symptoms, or both.

The hospital 16 must establish policies and procedures to reinforce the prompt investigation and reporting of adverse reactions to answer the following questions:

- Who within the hospital's management is responsible for receiving information concerning adverse events revealed during the post-operative assessment 28 (see FIG. 1)?
- How are these events to be documented? (e.g. evaluation, report, log, etc.).
- Who is responsible for determining if the adverse event was secondary to the tissue implant?
- Who notifies the tissue bank and receives their evaluation and report?
- Who is responsible for requesting additional information and testing, and for completing the investigation?
- What other transplant materials received from the tissue bank 14 need to be traced and quarantined within the hospital 16?
- All adverse event records need to be periodically reviewed for completeness.
- Who will report the investigation conclusions to the clinician?

In the event that the tissue bank reports that the transplantable material was the cause of the adverse reaction, or is otherwise contaminated, then the hospital must have in place established policies and procedures for quarantining all impacted transplantable materials stored within the hospital's inventory. Such procedures encompass the ability to trace such transplantable materials, notification of the patient's physician if the transplantable material was already transplanted, maintenance of a report or log that accounts for all such transplantable material products, and an identification of a department and specific staff members responsible for doing so.

Patients who have received a transplant from donors who subsequently are found to have HIV, HTLV-I/II, viral hepatitis, or other infectious agents known to be transmittable by tissue must also be identified and informed of infectious risks. This includes donors who have donated more than one time, such as donors of reproductive tissue, stem cells, and surgical bones. When such a donor is found to have a confirmed positive test for infectious agents, then all previous donations of transplantable materials need to be identified via the release and utilization portion 32 of the comprehensive tissue management system 10, and a determination of which donations could have occurred while the donor was within the window period for this infectious agent must be made. The hospital's procedures in cooperation with the supplier should include:

- Who is responsible for identifying all previous donations?
- Who is responsible for determining which previous donations are at risk?
- How should all subsequent recipients of the infected transplant material from this donor be identified?
- How should all such recipients be notified?
- Who is responsible for counseling the recipients of the infected transplant material?
- Is there a policy for follow-up testing of the recipients?
- Is notification of the state health department or other regulatory agencies required?
- Is there a procedure and log to document all of this information?
- Is the individual who counsels the recipients properly educated and trained?

Figure 29:
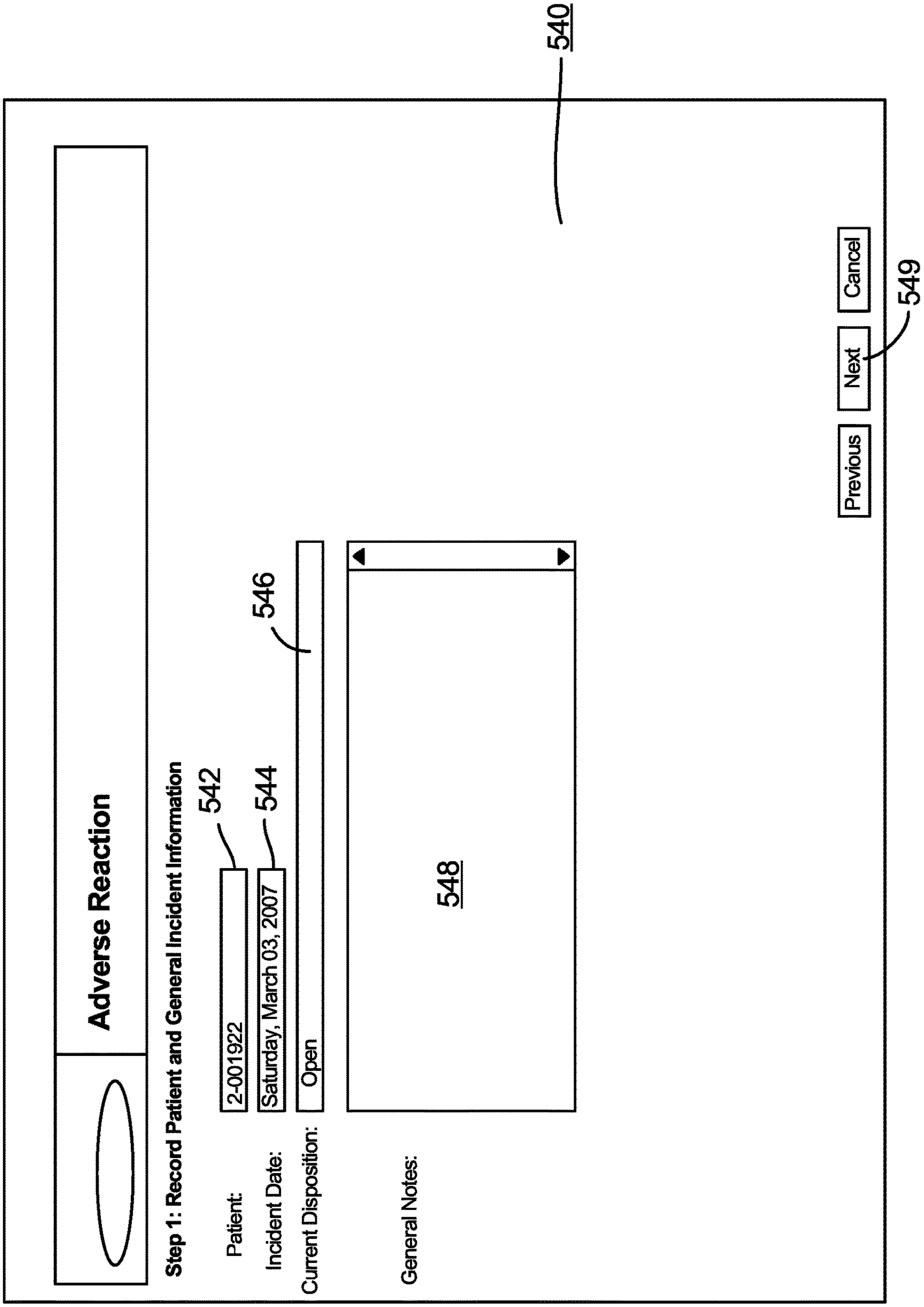

The adverse reaction investigation GUIs of the comprehensive tissue management system 10 are depicted in FIGS. 29-34. GUI 540 shown in FIG. 29 is accessed by means of selecting tab 72 or "record adverse reaction" hyperlink 88 of home GUI 60 shown in FIG. 4. Within this screen, patient identification number 542, the date on which an adverse reaction reported by the patient occurred 544, and the current disposition of the medical establishment's investigation of the reported adverse reaction 546 may be inserted. General notes regarding the investigation may be recorded in field 548.

Figure 30:
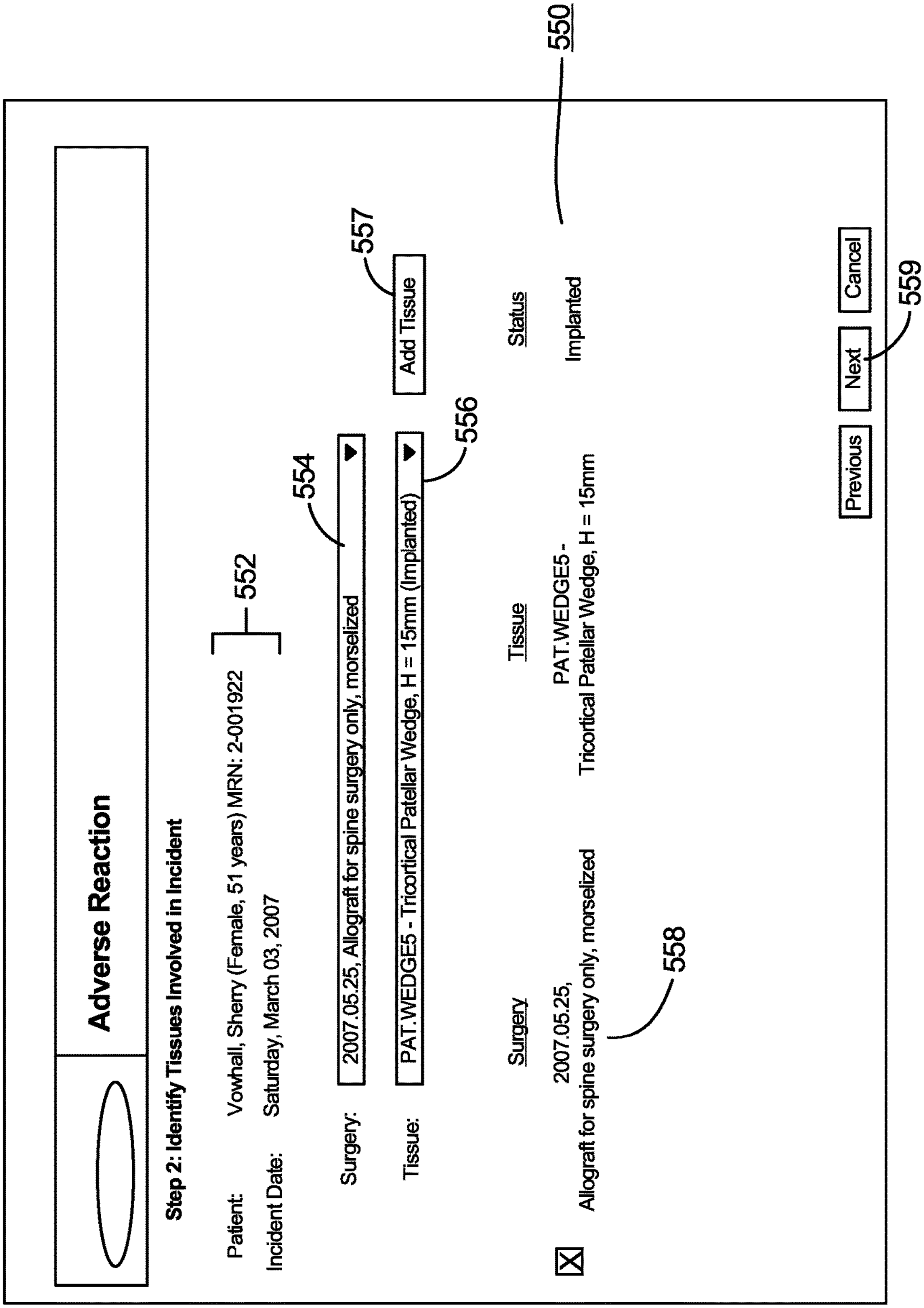

Clicking "next" button 549 transports the user to GUI 550 illustrated by FIG. 30. The patient and incident information from GUI 540 will be automatically populated in field 552. The specific surgery performed upon the patient 554 is identified by means of a drop down box. The tissue products previously recorded in GUI 500 for that surgical procedure are added by means of field 556 and "add tissue" button 557 to summary field 558.

Figure 31:
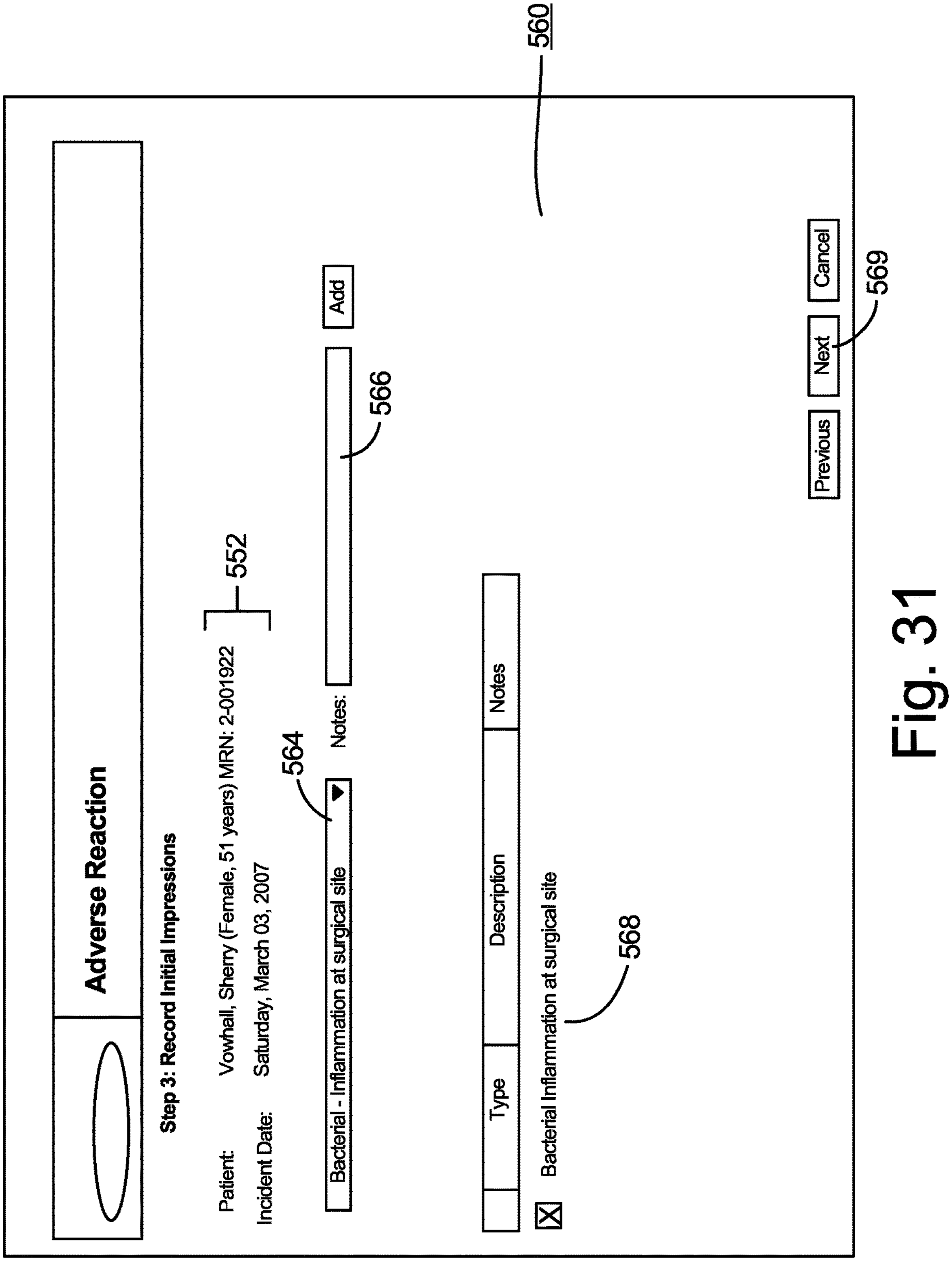

The next screen accessed by means of "next" button 559 is GUI 560 shown in FIG. 31. Using drop down box 564 and notes field 566, the user can record his initial opinion concerning the cause of the patient's adverse reaction. This is summarized in field 568.

Figure 32:
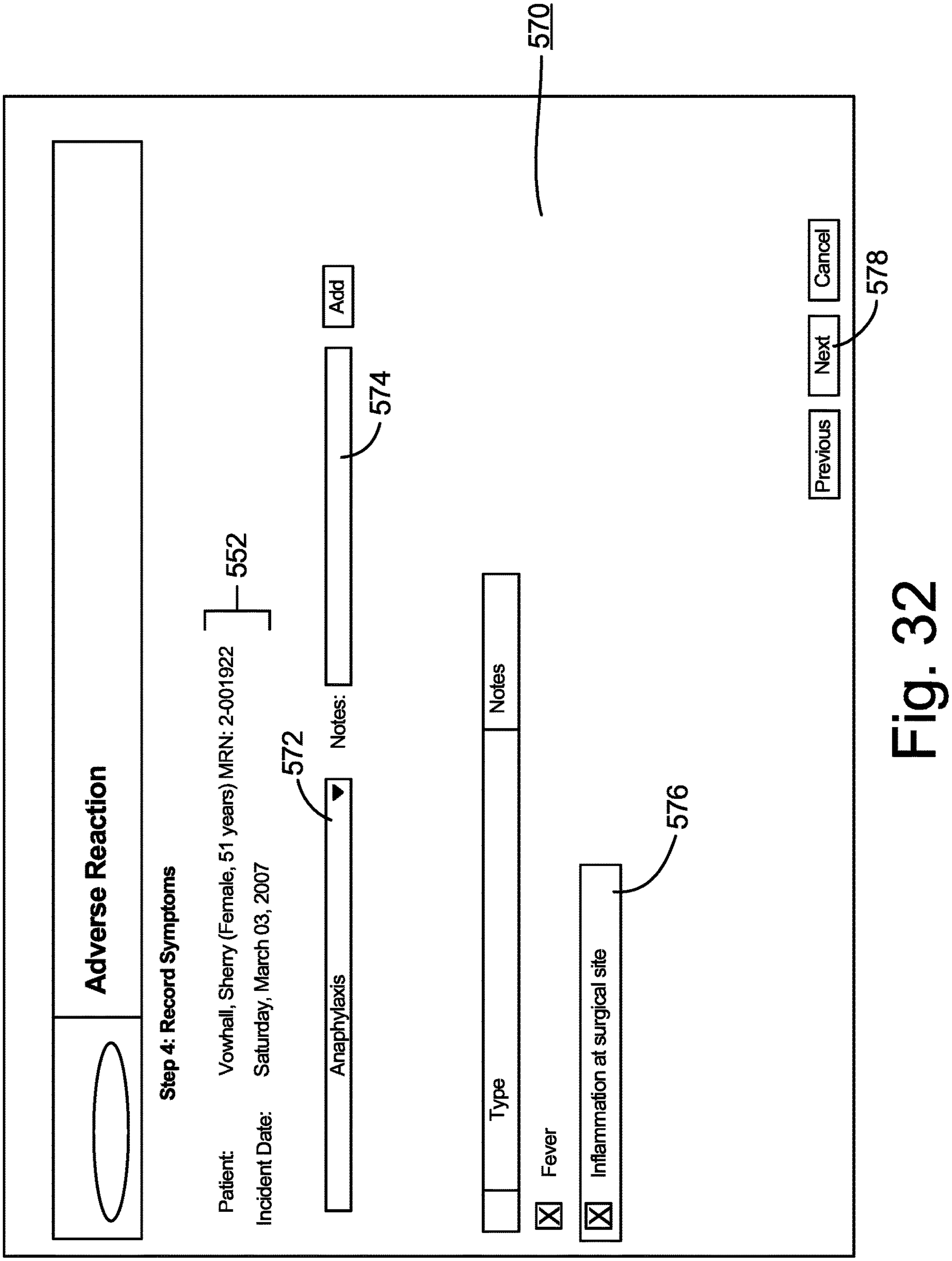

GUI 570 depicted in FIG. 32 is accessed via "next" button 569. Using drop down box 572 and notes field 574, the user can record the symptoms experienced by the patient due to the adverse reaction. These symptoms are cumulatively summarized in field 576.

Figure 33:
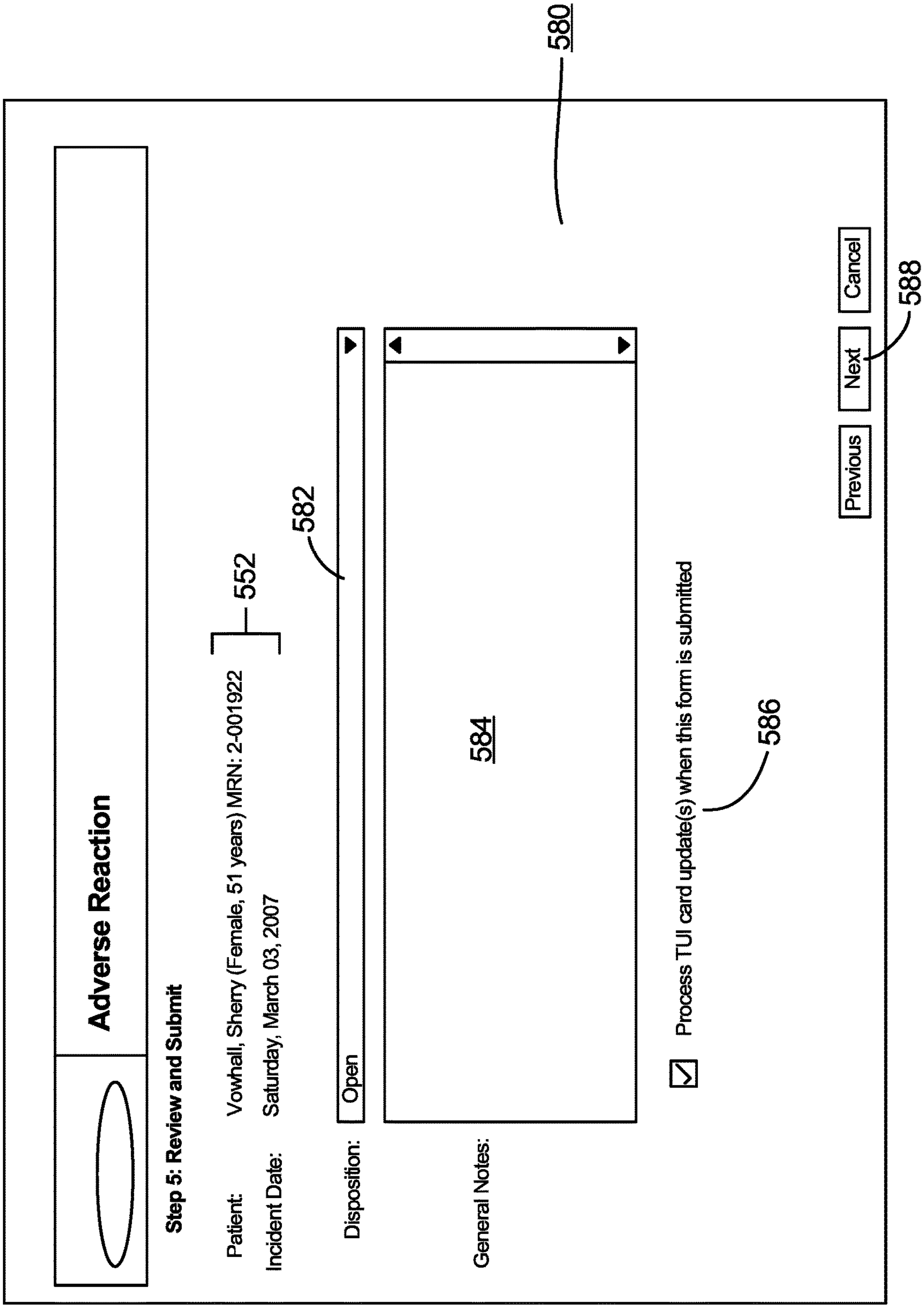

GUI 580 shown in FIG. 33 allows the disposition of the adverse reaction investigation 582 to be recorded, along with additional general notes 584 concerning the investigation. A check box 586 also instructs the software to reprocess the tissue usage information card produced by GUI 510 of the system, and resend this information to the appropriate supplier to inform them of the adverse reaction. By clicking on button 588, the reported information in this adverse reaction module can be submitted to the facility's management and regulatory authorities.

The end result of this submission is GUI 590 shown in FIG. 34. All of the critical information for a selected patient suffering an adverse reaction is automatically populated by the system in field 592, including name, date of birth, age, gender, MRN, last medical procedure, number of transplantable material items implanted, and the disposition of the investigation. The diagnostic tests run on the patient, and results thereof are automatically populated within field 594. Finally, an identification of the various notifications and reports owed to the FDA, patient, and supplier and the status thereof are clearly identified in field 596. In this manner, the comprehensive tissue management system 10 of the present invention creates an accurate record of the adverse reaction investigation 30 that prompts appropriate follow-up by the hospital's staff member 202 with regard to the patient 22, tissue bank 14, and regulatory authorities.

Another important feature of the tracing portion 32 of the comprehensive tissue management system 10 of the present invention is its facilitation of supplier recalls of transplantable materials. Initiated by the supplier or FDA, the medical establishment must ascertain whether the recalled product in question exists in its storage facilities awaiting surgical implant into a patient, or whether it has already been implanted into a patient.

Figure 35:
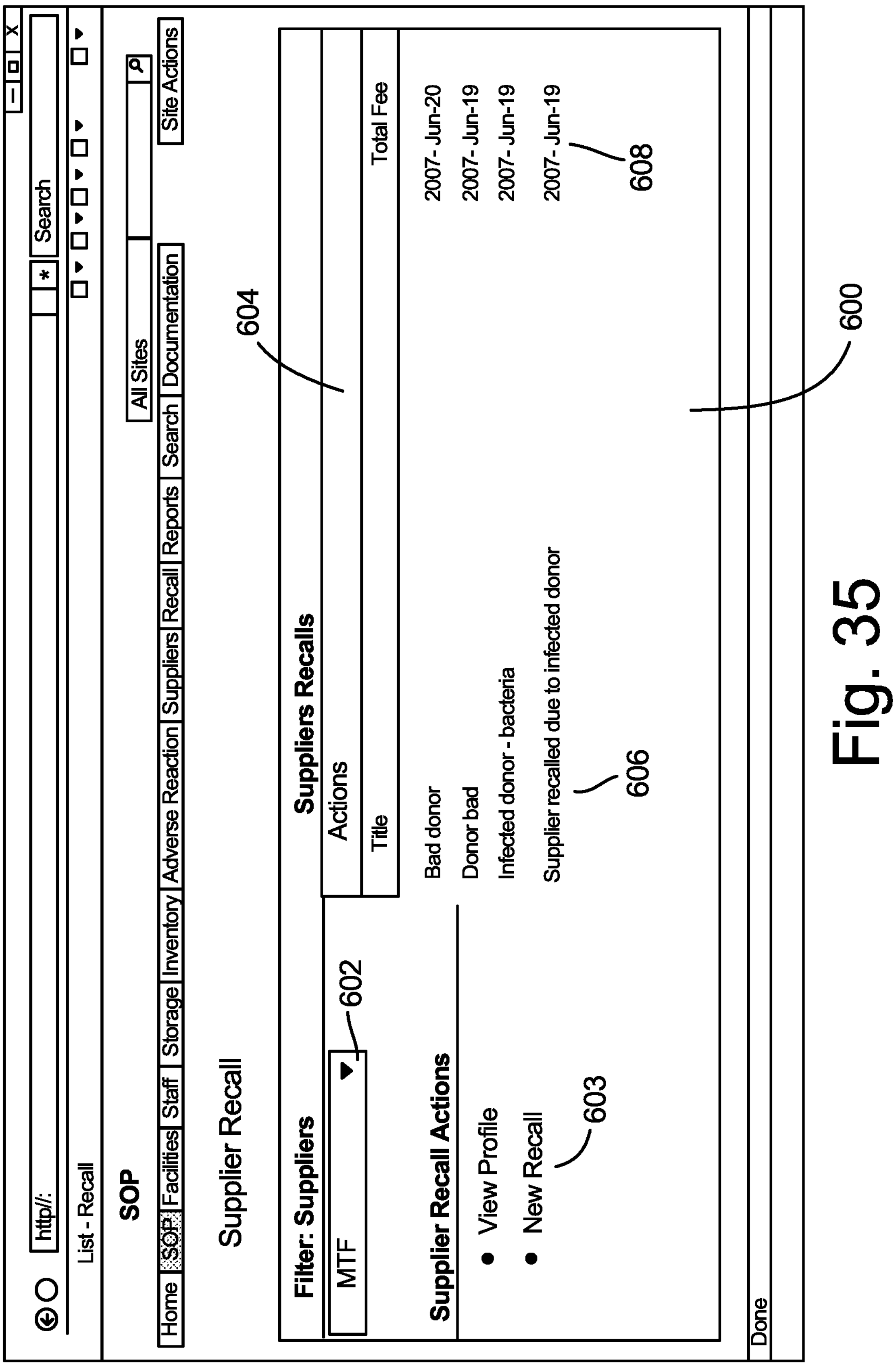
FIGS. 35-39 are interactive graphic user interfaces illustrating supplier tissue recall screens.

GUI 600 shown in FIG. 35 may be readily accessed by means of tab 74 or "process supplier recall" hyperlink 90 of home GUI screen 60 of FIG. 4. By selecting the supplier from drop down box 602, a listing of all of the recalls by or for that supplier is produced in field 604, along with a brief description of the recall 606 and its date 608. "New recall" hyperlink 603 enables the user to institute a new recall recordation for that supplier, adding an entry to field 604. This information is helpful for the staff of the medical establishment.

Figure 36:
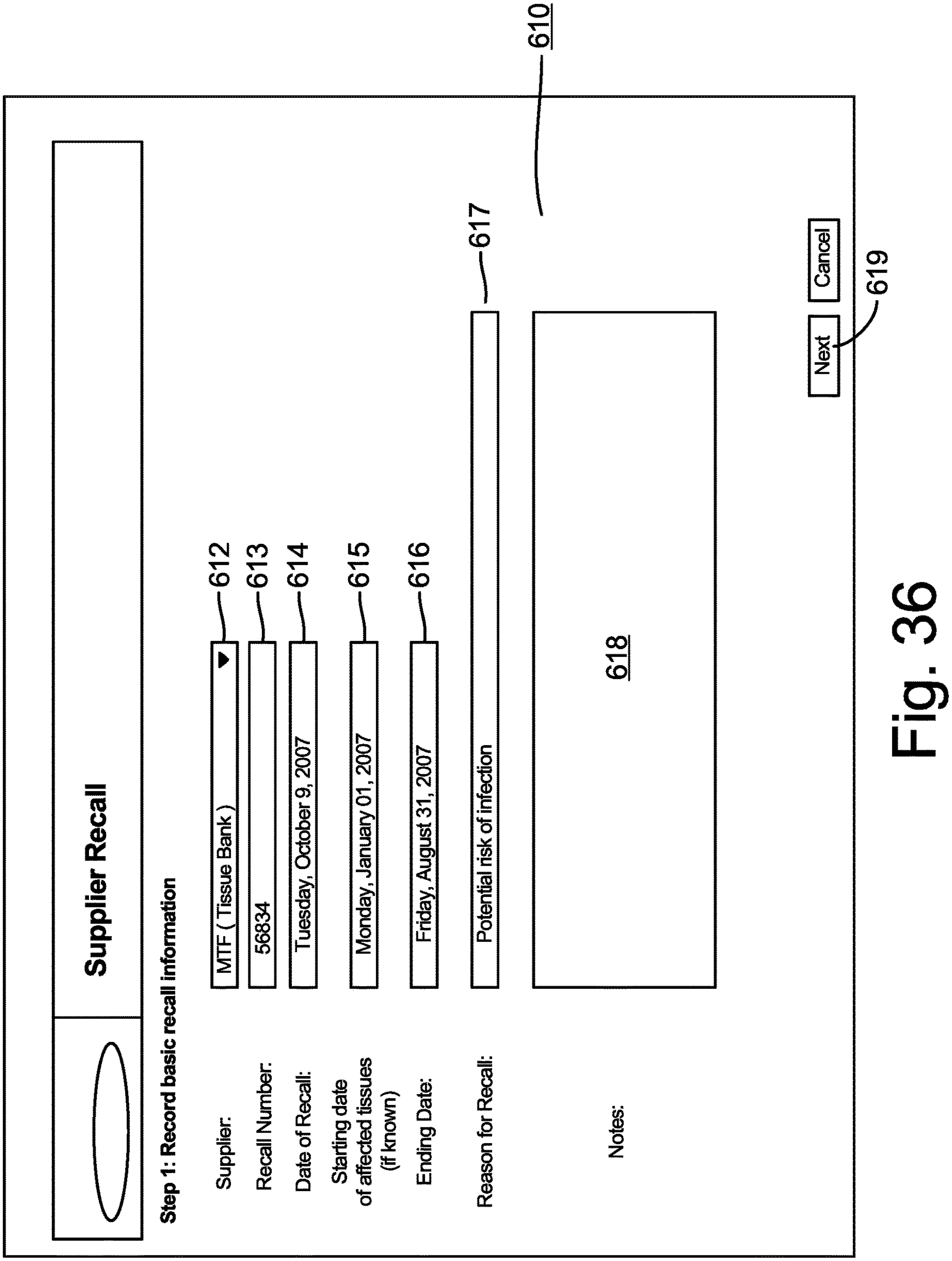

The relevant information for a supplier recall is entered into GUI 610 illustrated by FIG. 36. Such data includes the supplier 612, recall number 613, date of the recall 614, starting and ending dates 615 and 616, respectively, during which the transplantable material was known to be processed, and the reason 617 provided by the supplier or FDA for the recall. Notes may also be added to field 618.

Figure 37:
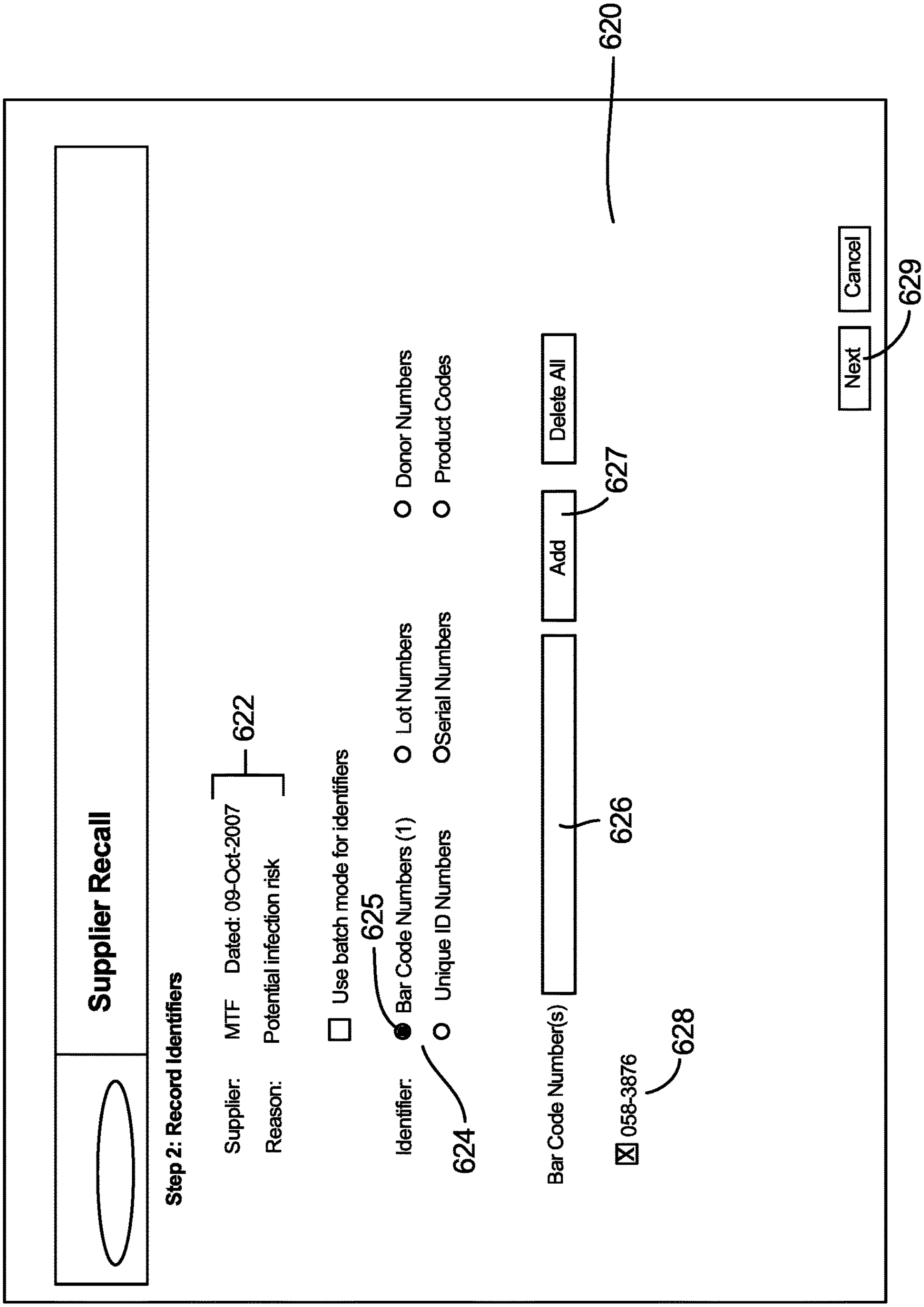

Clicking "next" button 619 takes the user to GUI 620 shown in FIG. 37. Descriptive data concerning the supplier, recall date, and reason for the recall are automatically populated in field 622. The user can then use radio buttons 624 to indicate whether bar code numbers, unique identification numbers, lot numbers, serial numbers, donor numbers, or product codes will be used to identify the transplantable material products. In this case, "bar code numbers" is checked 625. The bar code numbers can be typed or scanned into field 626, with the "add" button 627 clicked to add each bar code number to summary field 628.

Figure 38:
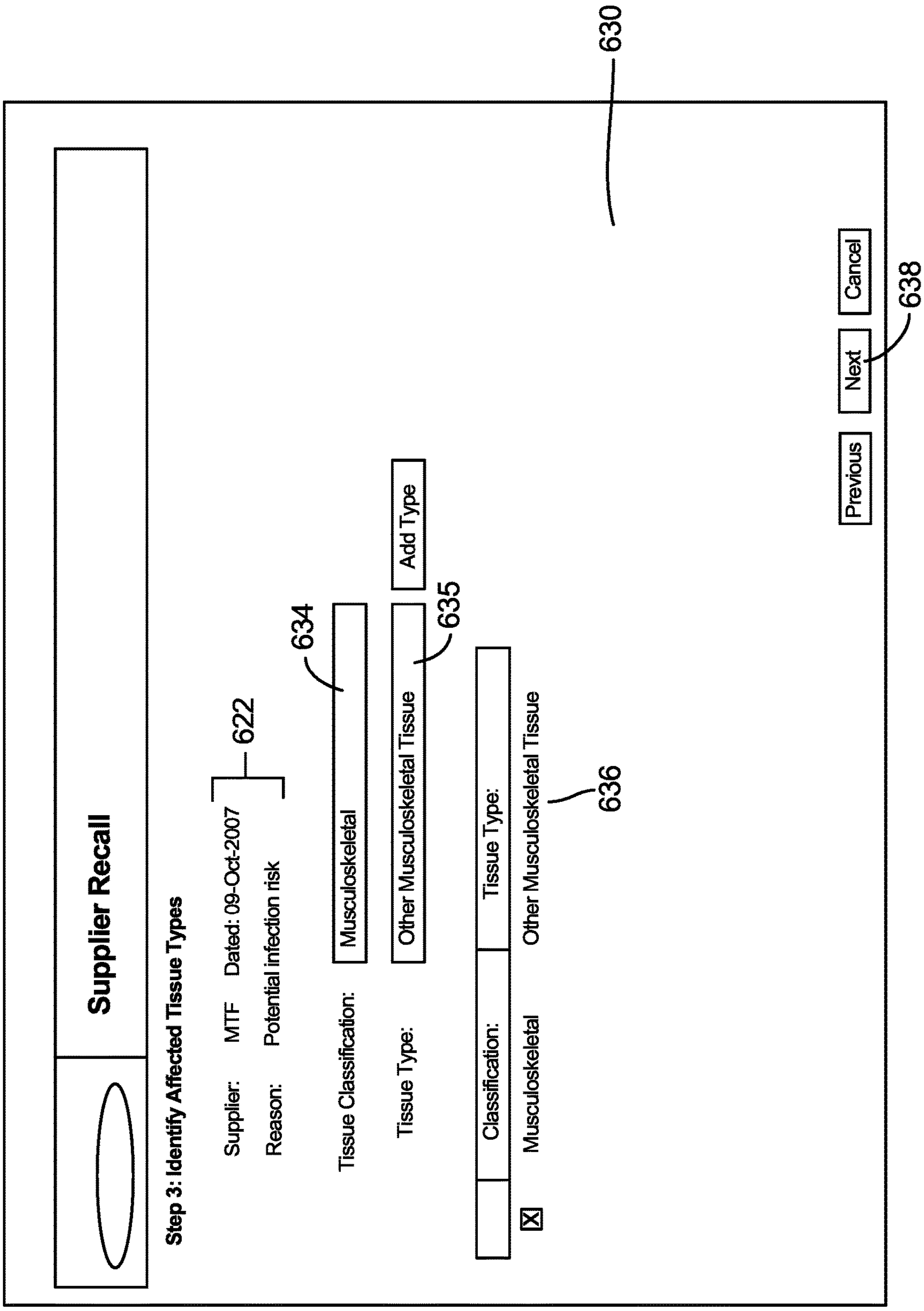

"Next" button 629 is then clicked to transfer the user to GUI screen 630 depicted in FIG. 38. The user enters the tissue classification and tissue type into fields 634 and 635, respectively, via drop down boxes. The information is summarized in field 636. This information provides an extra filter for the internal search conducted by the system for the recalled tissue product. This is important for avoiding duplicate product numbers, which could otherwise cause erroneous contacts of healthy patients who did not receive the recalled product.

Figure 39:
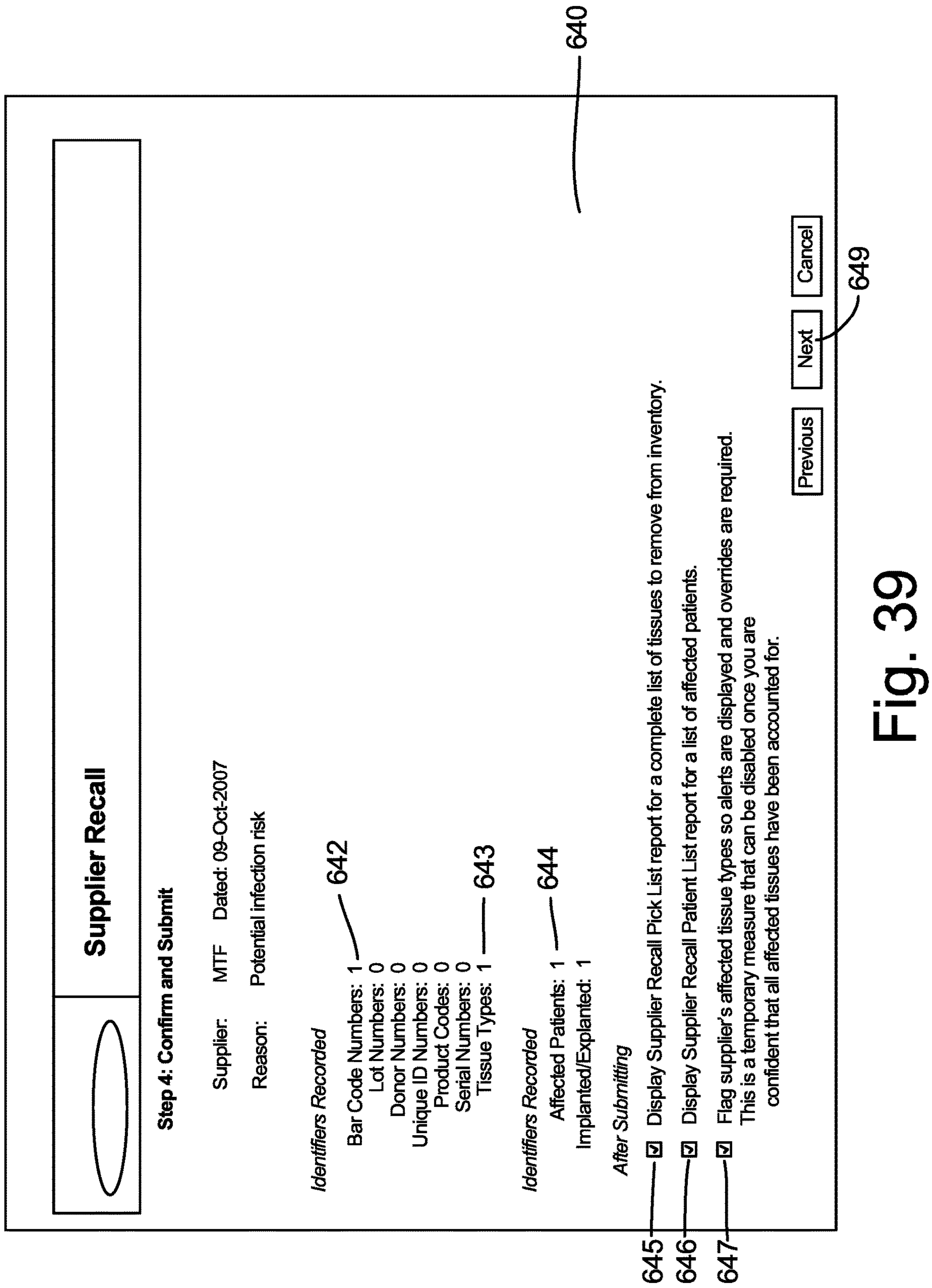

GUI 640 shown in FIG. 39 provides a summary screen of the recall information and transplantable material search results. Based upon the one bar code number 642 and tissue type 643 entered into GUIs 620 and 630, a single patient 644 was found to have received the recalled tissue product.

Clicking box 645 will cause the system to produce a list identifying all of the tissue items that need to be immediately removed from the medical establishment's storage inventory. Clicking box 646 produces a list of all patients into whom recalled tissue products were transplanted, who need to be notified of the tissue product recall, because they could be potentially adversely impacted. Finally, clicking box 647 sets up a warning flag within the system to notify the medical establishment facility in case any of the recalled tissue product should be accidentally delivered to the facility in the future by the recall supplier. The system will require an authorized supervisor to approve any check-in receipt of the material into the storage inventory in case it is safe to use it.

In its simplest embodiment, the comprehensive tissue management system 10 of the present invention may be a paper record keeping system. This may be particularly appropriate for relatively small medical establishments that do not handle and process enough transplantable materials to justify the cost of a computer-based system. The requirements established by the medical establishment for filling out and completing such paper forms and submitting them to appropriate managers may be sufficient for ensuring that the various processing steps for handling, storage, reconstitution, and surgical use of the transplantable material by staff members are being conducted in a manner compliant with prevailing regulations and industry standards, and that a thorough document record is produced therefore. However, it is important to incorporate within such policies and procedures safeguards for ensuring that all of these internal requirements are met by staff members in a compliant and timely manner. This could include a requirement that records be filled out from one processing step before the next processing step for the transplantable material can be conducted by the same or another staff member. Periodic internal and external audits will also be important for assuring compliance.

Figure 40:
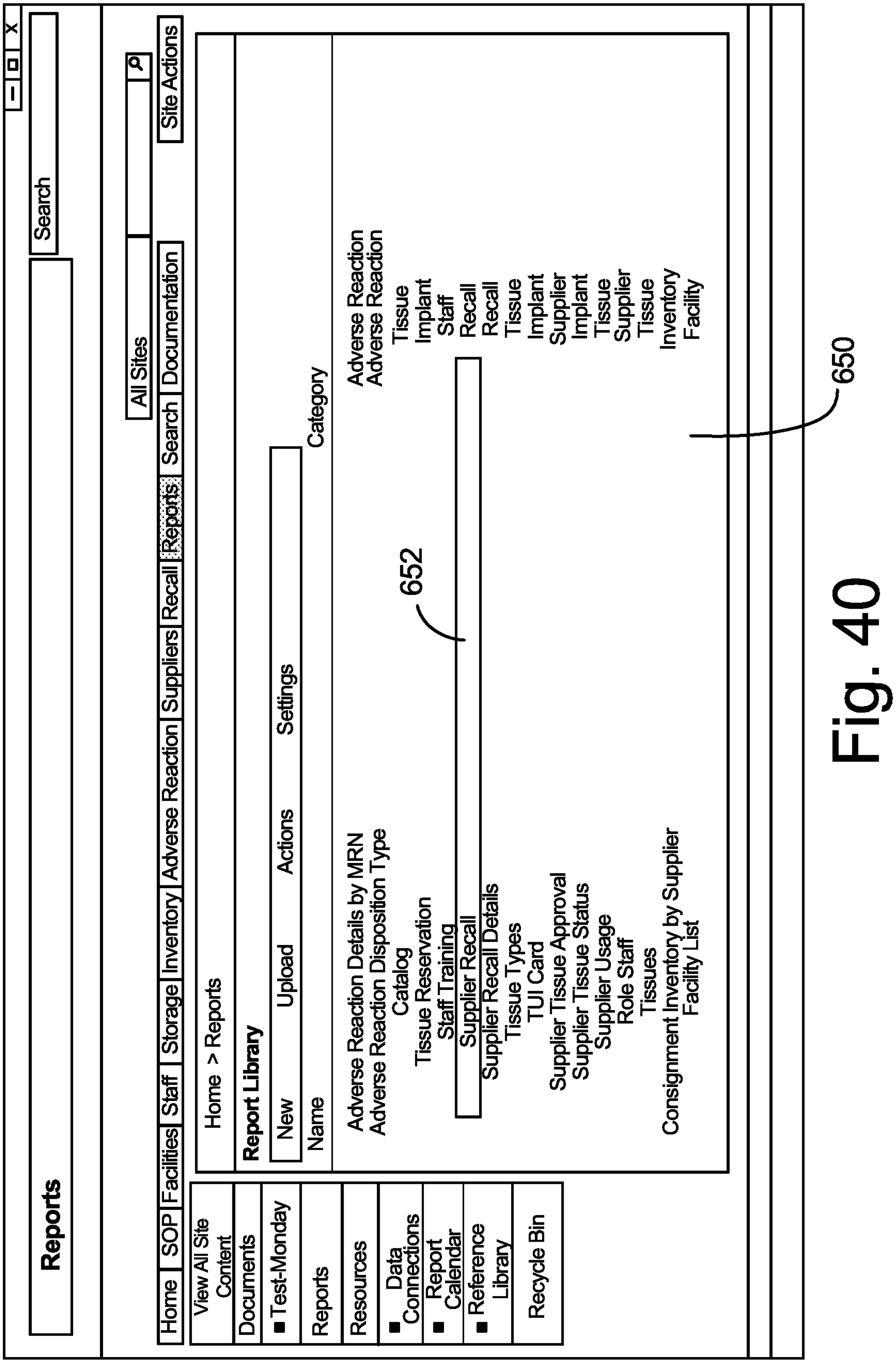
FIG. 40 is an interactive graphic user interface illustrating a reports generation screen.

However, the computer software system disclosed within this application for the comprehensive tissue management system 10 provides the most reliable method for providing a comprehensive information system concerning clinical usages of transplantable materials, and prompting hospital staff members to appropriately handle, store, process, transport, reconstitute, and use the transplantable material. Moreover, such a computer software-based system enables a user easily and quickly to search for desired information. Furthermore, such a computer system can readily compile the information to produce reports that can be used to manage and regulate clinical use of the transplantable materials, as illustrated by GUI 650 shown in FIG. 40. A variety of highly useful reports 652 can be produced by the system using the template library.

The computer system can also notify those monitoring the tissue of any of the steps described above by visual and/or audible means. Continual electronic monitoring of the transplantable material allows the computer system to store and display the entire history of a particular transplantable material sample. The continual monitoring reduces the risks that the transplantable material sample's integrity has been compromised.

Adequate policies and procedures adopted by the medical establishment can help with assuring that staff members are using the computer-based system in a compliant and timely manner. Periodic internal and external audits will also be helpful.

The above specifications and drawings provide a complete description of the structure and operation of the comprehensive tissue management system for acquisition and storage 26 of transplantable material and release and utilization 32 of transplantable material under the present invention. However, the invention is capable of use in various other combinations, modifications, embodiments, and environments without departing from the spirit and scope of the invention. Therefore, the description is not intended to limit the invention to the particular form disclosed, and the invention resides in the claim and hereinafter appended.

We claim:

1. A computer-implemented tissue tracing management system for tracing a piece of transplantable material received by a specific medical establishment from a supplier throughout an internal life of the transplantable material within the medical establishment until it is transplanted or implanted into a patient, such system comprising:

(a) a data base that stores information associated with the patient or transplantable material;

(b) a central processing unit and an internal or external memory unit incorporating a software program containing an expression of an organized set of instructions in coded language coupled to the database;

(c) such software program including a plurality of graphical user interfaces having one or more fields for input of data and one or more check boxes to be selected by a staff member, the software program incorporating a comprehensive set of standard operating procedures adopted by the specific medical establishment for documentation of a present location within the medical establishment of the transplantable material, and a login, handling, process treatment, thawing, rehydration, reconstitution, or use by a staff member of the transplantable material within the medical establishment, and at least one step for a proper login, handling, storage conditions, reconstitution, or surgical use of the transplantable material by staff members of the medical establishment in a manner compliant with prevailing safety regulations and industry mandates, at least one of the data input fields or check boxes being responsive to requirements under the standard operating procedures, the system in combination with the standard operating procedures programmed to:

(i) assign a unique identification code for the transplantable material upon its receipt by the medical establishment from the supplier;

(ii) require through the graphical user interface data entry within the field or selection of a check box by a staff member for the documentation of the completion of each step comprising login, handling, storage conditions, location movement, process treatment, thawing, rehydration, reconstitution, or surgical use applied by a staff member to the transplantable material within the medical establishment in conformity with the standard operating procedures;

(iii) require through the graphical user interface data entry within the field or selection of a check box by a staff member for the documentation of the present location of the transplantable material within the medical establishment;

(iv) require through the graphical user interface data entry within the field or selection of a check box by a staff member for the documentation of each staff member's identity who comes into contact with the transplantable material;

(v) require through the graphical user interface data entry within the field or selection of a check box by a staff member for the documentation of a date and time for each processing step applied by a staff member to the transplantable material;

(vi) require through the graphical user interface data entry within the field or selection of a check box by a staff member for the documentation of all materials used by a staff member to prepare and process the transplantable material;

(vii) require through the graphical user interface data entry within the field or selection of a check box by a staff member for the documentation of the unique identification code of the transplantable material transplanted or implanted into the patient; and (viii) upon a search query executed by a staff member, trace the transplantable material back to the supplier that supplied it to the medical establishment, to the login, handling, storage, process treatment, thawing, rehydration, reconstitution, or surgical use step applied by a staff member of the medical establishment to the transplantable material, or forward to the patient into whom the transplantable material was transplanted or implanted;

(ix) if the staff member has not inputted data into a required field or selected a required check box in the previous graphical user interface, the software program does not allow the staff member to proceed to the next graphical user interface;

(d) wherein the system is programmed to force the staff members in the medical establishment to properly carryout such documentation and tracing steps in accordance with the adopted standard operating procedures incorporated into the system by completing the required data entry fields or selecting the required check box for one graphical user interface before the next graphical user interface can be accessed;

(e) wherein the system is programmed to compare the content of the entered data field or check box against the contents of the adopted standard operating procedures that correspond to that processing step for the login, handling, storage conditions, reconstitution, or surgical use processing step to verify that the staff member properly carried out that processing step in compliance with the standard operating procedure, and:

(i) if compliance exists, then the software program allows the staff member access to the next graphical user interface relating to the next processing step for the login, handling, storage conditions, reconstitution, or surgical use of the transplantable material; and (ii) if compliance does not exist, then the software program does not allow the staff member to access the next graphical user interface relating to the next step for the login, handling, storage conditions, reconstitution, or surgical use of the transplantable material;

(f) wherein the transplantable material is chosen from the group consisting of human cells, tissue, or organs intended for implantation, transplantation, infusion, or transfer to a patient, including, but not limited to: musculoskeletal tissues including bone, tendons, fascia, ligaments, cartilage, and bioengineered bone products; skin; cardiovascular tissues including heart valves, arteries, veins, and pericardium; reproductive cells including sperm, semen, oocytes, fertilized eggs, and embryos; cellular therapies including stem cells, progenitor cells, cord blood, chondrocytes, bone marrow, and neural cells; dura mater; breast milk; eyes; corneas; organs; islet cells; parathyroids; autologous tissue; and synthetic and xenographic tissue used as replacements for human tissue; as well as non-biologic implants, including but not limited to: titanium screws, titanium or carbon-fiber cages or resorbable cages, fixation systems, saline or silicone breast implants, synthetic polymers, prosthetic hips, knees and other joint combinations thereof; as well as surgical instruments, equipment, reagents, and supplies associated with the transplanting or implanting of any transplant material into a patient; and (g) wherein the medical establishment is an organization directed to the storage, research, transplantation, or implantation of transplantable materials chosen from the group consisting of hospitals, medical clinics, surgical centers, fertility clinics, tissue banks, organ donor banks, university and research facilities, diagnostic laboratories, and willed body programs.

2. The computer-implemented tissue tracing management system of claim 1 further comprising means for designating one or more staff members of the medical establishment with specific responsibility for conducting each of the programming elements (ii-viii).

3. The computer-implemented tissue tracing management system of claim 1 further comprising means for sending to the supplier a tissue utilization information card for the transplantable material transplanted or implanted to the patient.

4. The computer-implemented tissue tracing management system of claim 1, wherein the tracing step is conducted in response to an adverse reaction detected in the patient into whom the transplantable material was transplanted or implanted.

5. The computer-implemented tissue tracing management system of claim 4 further comprising means for notifying the supplier that supplied the transplantable material to the medical establishment of the adverse reaction in the patient.

6. The computer-implemented tissue tracing management system of claim 1, wherein the tracing step for element (viii) is conducted in response to a recall received from the supplier that supplied the transplantable material to the medical establishment.

7. The computer-implemented tissue tracing management system of claim 1 further comprising means for ensuring that a staff member of the medical establishment who performs any of the steps documented in response to programming elements (ii-viii) possesses a relevant educational background or receives relevant training for performing such step.

8. The computer-implemented tissue tracing management system of claim 1 further comprising a visual or audible warning provided within the graphical user interface to the staff member if one of the required data input fields has not been completed when the staff member tries to access the next graphical user interface.

9. The computer-implemented tissue tracing management system of claim 1, wherein the information contained within the database comprises data regarding the supplier.

10. The computer-implemented tissue tracing management system of claim 1, wherein the information contained within the database comprises the storage conditions of the transplantable material.

11. The computer-implemented tissue tracing management system of claim 1, wherein the information contained within the database comprises clinical data concerning the patient.

12. The computer-implemented tissue tracing management system of claim 1, wherein the information contained within the database comprises clinical data concerning the transplant or implant surgery.

13. The computer-implemented tissue tracing management system of claim 1 further comprising means for reporting a list of certified suppliers of transplantable material.

14. The computer-implemented tissue tracing management system of claim 1 further comprising means for reporting certification credentials of a particular supplier.

15. The computer-implemented tissue tracing management system of claim 14, wherein the certification credentials are selected from the group consisting of Food & Drug Administration registration, American Association of Blood Banking accreditation, American Association of Tissue Banks ("AATB") accreditation, Eye Bank Association of America ("EBAA") accreditation, and licensure within a relevant geographic region.

16. The computer-implemented tissue tracing management system of claim 1 further comprising functional means for reporting results of an audit conducted by the specific medical establishment upon the supplier.

17. The computer-implemented tissue tracing management system of claim 1 further comprising functional means for reporting an order placed for a purchase of transplantable material.

18. The computer-implemented tissue tracing management system of claim 1 further comprising means for reporting a quality inspection assessment of transplantable material received from the supplier.

19. The computer-implemented tissue tracing management system of claim 1 further comprising means for reporting the present location of transplantable material within the medical establishment.

20. The computer-implemented tissue tracing management system of claim 1 further comprising means for reporting a storage history within the medical establishment of a piece of transplantable material.

21. The computer-implemented tissue tracing management system of claim 1 further comprising means for reporting results of an adverse reaction investigation with regard to a piece of transplanted material.

22. The computer-implemented tissue tracing management system of claim 1 further comprising means for automatic monitoring of an actual temperature condition of a storage unit containing the transplantable material against a temperature condition contained in the standard operating procedures.

23. The computer-implemented tissue tracing management system of claim 1, wherein the comparison of the content of the data field or check box entered by the staff member against the contents of the adopted standard operating procedures that correspond to that processing step for the login, handling, storage conditions, reconstitution, or surgical use processing step to verify that the staff member properly carried out that processing step in compliance with the adopted standard operating procedure is produced by the presence within a GUI screen of one or more check boxes that need to be selected by the staff member corresponding to the adopted standard operating procedure, or a preprogrammed look-up table containing valid content for that data entry made by the staff member.

24. The computer-implemented tissue tracing management system of claim 1 further comprising auto population by the system of one or more data fields within a graphical user interface screen with data entered by the staff member into a previous graphical user interface screen, or data programmed into the system in order to ensure that data entered into system between multiple graphical user interface screens is consistent.

* * * * *